(12) United States Patent
Bhavaraju et al.

(10) Patent No.: US 12,144,612 B2
(45) Date of Patent: Nov. 19, 2024

(54) SYSTEM AND METHOD FOR MODE SWITCHING

(71) Applicant: DexCom, Inc., San Diego, CA (US)

(72) Inventors: Naresh C. Bhavaraju, San Diego, CA (US); Michael A. Bloom, Carlsbad, CA (US); Leif N. Bowman, San Diego, CA (US); Alexandra Lynn Carlton, San Marcos, CA (US); Katherine Yerre Koehler, Solana Beach, CA (US); Hari Hampapuram, Carlsbad, CA (US); Lauren Hruby Jepson, San Diego, CA (US); Jonathan Hughes, Carlsbad, CA (US); Apurv Ullas Kamath, San Diego, CA (US); Anna Leigh Davis, Cardiff, CA (US); Peter C. Simpson, Cardiff, CA (US); Stephen J. Vanslyke, Carlsbad, CA (US)

(73) Assignee: Dexcom, Inc., San Diego, CA (US)

( * ) Notice: Subject to any disclaimer, the term of this patent is extended or adjusted under 35 U.S.C. 154(b) by 545 days.

(21) Appl. No.: 14/975,444

(22) Filed: Dec. 18, 2015

(65) Prior Publication Data

US 2016/0106350 A1   Apr. 21, 2016

Related U.S. Application Data

(63) Continuation of application No. 14/862,079, filed on Sep. 22, 2015.
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0002* (2013.01); *A61B 5/14503* (2013.01);
(Continued)

(58) Field of Classification Search
CPC ............. A61B 5/14532; A61B 5/4839; A61M 2230/201; A61M 5/1723
See application file for complete search history.

(56) References Cited

U.S. PATENT DOCUMENTS 5,267,152 A   11/1993   Yang et al.
7,591,801 B2   9/2009   Brauker et al.
(Continued)

FOREIGN PATENT DOCUMENTS

EP   1718350 B1   5/2013
GB   2488487 A   8/2012
(Continued)

OTHER PUBLICATIONS

International Preliminary Report on Patentability for Application No. PCT/US2015/051548 mailed on Apr. 6, 2017, 7 pages.
(Continued)

*Primary Examiner* — Tse W Chen
*Assistant Examiner* — Michael A Catina

(57) ABSTRACT

Systems and methods described provide dynamic and intelligent ways to change the required level of user interaction during use of a monitoring device. The systems and methods generally relate to real time switching between a first or initial mode of user interaction and a second or new mode of user interaction. In some cases, the switching will be automatic and transparent to the user, and in other cases user notification may occur. The mode switching generally affects the user's interaction with the device, and not just
(Continued)

internal processing. The mode switching may relate to calibration modes, data transmission modes, control modes, or the like.

20 Claims, 32 Drawing Sheets

Related U.S. Application Data

(60) Provisional application No. 62/053,733, filed on Sep. 22, 2014.

(51) Int. Cl.
| | | |
|---|---|---|
| *A61B 5/1455* | (2006.01) | |
| *A61B 5/1486* | (2006.01) | |
| *A61B 5/1495* | (2006.01) | |
| *A61M 5/172* | (2006.01) | |
| *G16H 40/40* | (2018.01) | |
| *G16H 40/63* | (2018.01) | |

(52) U.S. Cl.
CPC ........ *A61B 5/14546* (2013.01); *A61B 5/1455* (2013.01); *A61B 5/1486* (2013.01); *A61B 5/1495* (2013.01); *A61B 5/7221* (2013.01); *A61B 5/7275* (2013.01); *A61B 5/7282* (2013.01); *A61B 5/742* (2013.01); *A61B 5/7435* (2013.01); *A61B 5/746* (2013.01); *A61B 5/7475* (2013.01); *A61M 5/1723* (2013.01); *G16H 40/40* (2018.01); *G16H 40/63* (2018.01); *A61B 5/0004* (2013.01); *A61B 5/6898* (2013.01); *A61B 5/72* (2013.01); *A61B 2560/0223* (2013.01); *A61B 2560/0487* (2013.01); *A61M 2230/005* (2013.01); *A61M 2230/201* (2013.01); *Y02A 90/10* (2018.01)

(56) References Cited

U.S. PATENT DOCUMENTS

| | | |
|---|---|---|
| 7,783,442 B2 | 8/2010 | Mueller et al. |
| 7,885,697 B2 | 2/2011 | Brister et al. |
| 7,946,985 B2 | 5/2011 | Mastrototaro et al. |
| 7,976,492 B2 | 7/2011 | Brauker et al. |
| 8,423,381 B2 | 4/2013 | Gegner et al. |
| 8,442,610 B2 | 5/2013 | Goode et al. |
| 8,460,231 B2 | 6/2013 | Brauker et al. |
| 8,579,879 B2 | 11/2013 | Palerm et al. |
| 8,721,585 B2 | 5/2014 | Brauker et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| 9,050,413 B2 | 6/2015 | Brauker et al. |
| 9,155,843 B2 | 10/2015 | Brauker et al. |
| 9,452,258 B2 | 9/2016 | Dobbles et al. |
| 9,452,259 B2 | 9/2016 | Dobbles et al. |
| 9,457,146 B2 | 10/2016 | Dobbles et al. |
| 9,463,277 B2 | 10/2016 | Dobbles et al. |
| 2003/0100846 A1* | 5/2003 | Custer ................ A61B 5/14514 600/573 |
| 2005/0027180 A1 | 2/2005 | Goode et al. |
| 2005/0043598 A1 | 2/2005 | Goode, Jr. et al. |
| 2006/0020192 A1 | 1/2006 | Brister et al. |
| 2007/0208246 A1 | 9/2007 | Brauker et al. |
| 2007/0258395 A1* | 11/2007 | Jollota ................ A61B 5/14532 370/310 |
| 2008/0161664 A1* | 7/2008 | Mastrototaro ..... A61B 5/14532 600/347 |
| 2008/0228045 A1 | 9/2008 | Gao et al. |
| 2008/0234663 A1 | 9/2008 | Yodfat et al. |
| 2009/0005666 A1 | 1/2009 | Shin et al. |
| 2009/0006034 A1 | 1/2009 | Hayter et al. |
| 2009/0112478 A1* | 4/2009 | Mueller, Jr. ........ A61B 5/14532 600/347 |
| 2009/0178459 A1 | 7/2009 | Li et al. |
| 2009/0192366 A1* | 7/2009 | Mensinger ............ G16H 40/63 706/14 |
| 2010/0057041 A1 | 3/2010 | Hayter |
| 2010/0138197 A1 | 6/2010 | Sher |
| 2010/0174168 A1 | 7/2010 | Goode, Jr. et al. |
| 2010/0249561 A1 | 9/2010 | Patek et al. |
| 2010/0262434 A1 | 10/2010 | Shaya |
| 2010/0332142 A1 | 12/2010 | Shadforth et al. |
| 2011/0015944 A1* | 1/2011 | Gegner ................ A61B 5/083 705/2 |
| 2011/0178820 A1 | 7/2011 | Soni et al. |
| 2011/0191044 A1 | 8/2011 | Stafford |
| 2011/0213559 A1 | 9/2011 | Pollack et al. |
| 2012/0029942 A1 | 2/2012 | Katsuki et al. |
| 2012/0078071 A1 | 3/2012 | Bohm et al. |
| 2012/0083714 A1 | 4/2012 | Yuen |
| 2012/0108935 A1 | 5/2012 | Liang et al. |
| 2012/0125075 A1 | 5/2012 | Gottlieb et al. |
| 2012/0220979 A1 | 8/2012 | Brauker et al. |
| 2012/0265037 A1 | 10/2012 | Böhm et al. |
| 2012/0271557 A1 | 10/2012 | Sekimoto et al. |
| 2013/0218126 A1 | 8/2013 | Hayter et al. |
| 2014/0000338 A1 | 1/2014 | Luo et al. |
| 2014/0005505 A1 | 1/2014 | Peyser et al. |
| 2014/0012510 A1 | 1/2014 | Mensinger et al. |
| 2014/0039383 A1 | 2/2014 | Dobbles et al. |
| 2014/0277286 A1 | 9/2014 | Cinbis |
| 2014/0288494 A1 | 9/2014 | Brister et al. |
| 2015/0164387 A1* | 6/2015 | Varsavsky ............ A61B 5/0537 702/182 |
| 2015/0165117 A1 | 6/2015 | Palerm et al. |
| 2016/0081597 A1 | 3/2016 | Bhavaraju et al. |
| 2016/0113557 A1 | 4/2016 | Bhavaraju et al. |
| 2016/0113558 A1 | 4/2016 | Bhavaraju et al. |
| 2016/0198988 A1 | 7/2016 | Bhavaraju et al. |
| 2019/0328291 A1 | 10/2019 | Bhavaraju et al. |
| 2019/0328292 A1 | 10/2019 | Bhavaraju et al. |

FOREIGN PATENT DOCUMENTS

| | | |
|---|---|---|
| WO | 2004109992 A1 | 12/2004 |
| WO | WO 2008-086541 A9 | 7/2008 |
| WO | WO-2008086541 A2 | 7/2008 |
| WO | WO-2008086541 A3 | 9/2008 |
| WO | 2012178134 A2 | 12/2012 |
| WO | WO 2015-156965 | 10/2015 |
| WO | 2015187366 A1 | 12/2015 |

OTHER PUBLICATIONS

International Search Report and Written Opinion for Application No. PCT/US2015/051548 mailed on Dec. 16, 2015, 9 pages.
Office Action from Australian Patent Application No. 2019202148, dated Jan. 20, 2021, 5 pages.
Notice of Opposition from European application No. 15778109.7, mailed Sep. 21, 2021, 48 pages.
U.S. Appl. No. 62/053,733, inventors Bowman; Leif N. et al., filed on Sep. 22, 2014.
Office Action from Australian Patent Application No. 2019202148, dated Mar. 16, 2021, 3 pages.
Office Action from Canadian Patent Application No. 2,953,577, dated May 3, 2021, 5 pages.
Bothe M.K., et al., "The use of Reinforcement Learning Algorithms to meet the challenges of an Artificial Pancreas", Expert Review Medical Devices, vol. 10(5), 2013, pp. 661-673.
DEXCOM Inc., "Dexcom G4 Platinum Continuous Glucose Monitoring System Quick Start Guide," 2013, 2 pages.
Vaddiraju S., et al., "Technologies for Continuous Glucose Monitoring: Current Problems and Future Promises", Journal of Diabetes Science and Technology, vol. 4(6), Nov. 2010, pp. 1540-1562.

* cited by examiner

SYSTEM AND METHOD FOR MODE SWITCHING

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 14/862,079 filed Sep. 22, 2015, which claims the benefit of U.S. Provisional Application No. 62/053,733, filed Sep. 22, 2014. The aforementioned application is incorporated by reference herein in its entirety, and is hereby expressly made a part of this specification.

TECHNICAL FIELD

The present embodiments relate to continuous analyte monitoring, and, in particular, to control of operation of an analyte monitor upon changes in available data in a continuous analyte monitoring system.

BACKGROUND

Diabetes mellitus is a disorder in which the pancreas cannot create sufficient insulin (Type I or insulin-dependent) and/or in which insulin is not effective (Type II or non-insulin-dependent). In the diabetic state, the patient or user suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. It is not only unlikely that a person with diabetes will become aware of a dangerous condition in time to counteract it, but it is also likely that he or she will not know whether his or her blood glucose concentration value is going up (higher) or down (lower) based on conventional methods. Diabetics thus may be inhibited from making educated insulin therapy decisions.

Another device that some diabetics used to monitor their blood glucose is a continuous analyte sensor, e.g., a continuous glucose monitor (CGM). A CGM typically includes a sensor that is placed invasively, minimally invasively or non-invasively. The sensor measures the concentration of a given analyte within the body, e.g., glucose, and generates a raw signal using electronics associated with the sensor. The raw signal is converted into an output value that is rendered on a display. The output value that results from the conversion of the raw signal is typically expressed in a form that provides the user with meaningful information, and in which form users have become familiar with analyzing, such as blood glucose expressed in mg/dL.

The above discussion assumes the output value is reliable and true, and the same generally requires a significant degree of user interaction to ensure proper calibration. For example, current CGMs rely heavily on user interaction, for example, using blood glucose meter readings to confirm glucose concentration values before dosing insulin. However, additional user action adds a significant source of error in the monitoring and reduces convenience by requiring more action of the user than desired.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles meet the needs of the above in several ways. In particular, the systems and methods provide dynamic and intelligent ways to change the required level of user interaction during use of the monitoring device, e.g., over the course of the sensor session, as dictated by the usability of the device as well as in some cases user choice. The usability of the device is often influenced by the usability of the data received from the sensor. Such changes may increase or decrease the level and type of user interaction, depending on usability of sensor data and also often according to other available data, but generally are intended to dynamically reduce the level of user interaction based on the desired or needed usability of sensor data.

The systems and methods described here generally relate to real time switching between a first or initial mode of user interaction and a second or new mode of user interaction. In some cases, the switching will be automatic and transparent to the user, and in other cases user notification (or request for confirmation) may occur. The mode switching may cause a switch from a first mode to a second mode, followed by a switch to a third mode or back to the first or second modes. In any case, the mode switching will generally affect the user's interaction with the device, and not just cause internal processing changes within the device, although such processing changes will generally accompany the mode switching.

In many cases the decision or trigger to switch between modes relates to the usability of a sensor signal, as compared to a transition criteria, but may also be based on other data, combined (or not) with usability data, such as the value of the sensor signal, external data, and the like.

In one implementation, an analyte monitoring device may transition or switch types of calibration modes, e.g., from a user-dependent calibration to a device self-calibration mode, i.e., a calibration routine using blood glucose concentration values from an external meter to a calibration routine performed by the device itself (i.e., without real time external reference values). In another implementation, an analyte monitoring device may transition or switch types of data transmission modes, e.g., from providing information or data on-demand (e.g., upon user demand) to a mode in which information or data transmission is initiated by the device, e.g., as a regular or irregular periodic communication and/or in response to a trigger such as a large excursion. In some cases, as described below, such is termed a mode switch from scheduled transmissions to unscheduled transmissions. In yet another implementation, an analyte monitoring device may transition or switch from one type of decision-support mode to another, e.g., from a therapeutic use to a non-therapeutic use (e.g., adjunctive use) or more granularly from one mode or phase of control to another, including providing educational information versus providing therapeutic information. More generally, an analyte monitoring device may be configured to switch between modes or phases of control, such as described in greater detail below with respect to FIG. 15A. In all of these implementations, the mode transition or switches may generally be performed in both directions, and in the cases of multiple phases of control, between various phases of control, both sequential and nonsequential.

A number of triggers will be described, and generally the triggers are based on one or more criteria, e.g., where a determined parameter or variable ("determined data") meets, exceeds, matches, or otherwise bears a predetermined relationship with a threshold, i.e., a predetermined transition threshold criterion or criteria, or is determined or predicted to do so in the future. The determined parameter or variable may be data associated with the sensor signal, i.e., the sensor signal value or a scaled representation thereof, data about the sensor signal, e.g., data from signal analysis indicating its noise level or the like, data from an external source, e.g., data from a blood glucose meter, temperature sensor, clock, location sensor, or the like, as well as other data as will be described below.

Systems and methods according to present principles may use one or more of many different triggers, i.e., data and accompanying transition criteria, on which to base mode switching. In some cases, for specific types of mode switching, particular determined parameters or variables will be especially useful. For example, data usability may be especially pertinent when deciding and switching calibration modes or decision-support modes. The signal value itself may be especially pertinent when deciding data or information transmission modes. However, these are purely exemplary and it will be understood that in given implementations other criteria may prove useful.

In one aspect, the embodiments are directed towards a method of operating a continuous glucose monitoring device, the continuous glucose monitoring device coupled to a glucose sensor and operating in an initial mode of operation, including: measuring a signal indicative of glucose concentration data; displaying the glucose concentration data on a user interface of the continuous glucose monitoring device, the user interface in the initial mode of operation having an initial mode of user interaction; determining data indicative of a usability of the continuous glucose monitoring device; comparing the determined data to one or more transition criteria; if the comparing indicates the determined data has met or will meet the transition criteria, causing the continuous glucose monitoring device to transition to a new mode of operation; and displaying the glucose concentration data on the user interface of the continuous glucose monitoring device. The user interface in the new mode of operation has a different mode of user interaction than the initial mode, such that the continuous glucose monitoring device operates in a mode of user interaction according to the device usability.

Implementations of the embodiments may include one or more of the following. The displaying may be based at least in part on the mode of operation. The determining data may include receiving data from the sensor. The receiving data from the sensor may include receiving data from a sensor electronics module coupled to the sensor. The sensor may be configured for in vivo insertion into the patient. A first output of the monitoring device in the initial mode of operation may represent the initial mode of user interaction and a second output of the monitoring device in the new mode of operation may represent the new mode of user interaction, and the first and second outputs may be different. The initial and new modes of user interaction may be configured such that the new mode of user interaction requires less user interaction than the initial mode of user interaction. The initial and new modes of user interaction may be selected from the group consisting of: user-dependent calibration and device self-calibration. The analyte may be glucose and the user-dependent calibration may correspond to entry of a calibration value from an external blood glucose meter. The initial and new modes of user interaction may include levels of confirmation interactions. The analyte may be glucose and the initial and new modes of user interaction may include different levels of decision support selected from the group consisting of: non-therapeutic (adjunctive), therapeutic (non-adjunctive), and phases of control in an artificial pancreas system. The analyte may be glucose and the initial and new modes of user interaction may be data transmission modes selected from the group consisting of on-demand data transmission and device-initiated data transmission. The initial and new modes of user interaction may be selected from the group consisting of: pushed data or pulled data. The determined data may include an analyte concentration value and/or a time rate of change thereof.

The determined data indicative of the usability of the device and the transition criteria may include one or more parameters indicative of the usability of a signal from the sensor, such as one or more parameters selected from the group consisting of accuracy, reliability, stability, confidence, and/or glycemic urgency index. The one or more parameters related to the usability of the signal may correspond to a level of noise or to one or more faults detected in the signal, and the transition criteria may be a threshold level of noise or a predetermined type or level of fault, which may be determined based on a long-term trend of the signal, a short-term trend of the signal, or on a history of a user's previous sensor session. The one or more parameters related to the usability of the signal may correspond to one or more of the group consisting of: signal value, a range of signal values, or a time rate of change thereof; analyte concentration value or range of values; calibration data; a measured error at calibration; data from self-diagnostics or calibration diagnostics; metadata about sensor identity; environmental data corresponding to a sensor; historical pattern data; external data; data about frequency of calibration; biological data about sensor placement; a time duration since sensor implantation; an impedance associated with the signal; a received user response to a prompt displayed on a user interface; a decision support mode; a data transmission mode; data about a selected use of the monitoring device; data about clinical or user goals; or combinations of the above.

For example, the environmental data may correspond to altitude or temperature data about a sensor environment. The calibration data may be selected from the group consisting of: calibration values, confidence in calibration values, uncertainty in calibration values, range of calibration values, rate of change of calibration values, current calibration values compared to historical calibration values, stability in calibration values, whether calibration values match expected or predicted values, confidence in a user's ability to accurately enter calibration values from a meter, whether entered calibration data corresponds to a default or pre-entered value, or combinations of the above. The historical pattern data may include data about rebound variability.

The external data may be from an activity monitor, a sleep monitor, a medicament pump, GPS device, a redundant analyte sensor, a smart pen, or combinations of the above. The biological data about sensor placement may correspond to data about: tissue type, wound response, diffusion distance, or combinations of the above. The diffusion distance may be proportional to one or more selected from the group consisting of: impedance, thickness of membrane over electrode array, oxygen depletion rate, diffusion of specific species between electrodes, or combinations of the above. The decision support mode may be selected from the group consisting of: non-therapeutic (adjunctive), therapeutic (non-adjunctive), and different levels of control of an artificial pancreas system. The data about a selected use of the monitoring device may include data about uses selected from the group consisting of: weight loss monitoring, monitoring exercise or activity impact on glucose, post-meal glucose summary, food selection, effect of the monitored analyte on illness or menstrual cycle or pregnancy, user preference or convenience, or combinations of the above. The data about clinical or user goals may include: data about user knowledge of device, desired accuracy of device, desired convenience of device, use of device for hypoglycemic avoidance, use of device for nighttime control, use of device for postprandial control, qualitative or quantitative desired duration of sensor session, or combinations of the above. The desired convenience of the device may correspond to a number of required external meter calibration values.

The initial mode may be user-dependent calibration, and before the causing step, the method may further include causing the device to periodically and temporarily enter a self-calibration mode, to interrogate the sensor and to examine a transient response, followed by a re-entering of the user-dependent calibration initial mode. The method may further include displaying output data based on the new mode. The method may further include displaying an indication of an expected duration of the new mode. The method may further include displaying an indication of sensor performance.

Certain implementations may particularly apply to calibration mode. For example, the initial mode may be user-dependent calibration and the new mode may be device self-calibration; or the initial mode may be device self-calibration and the new mode may be user-dependent calibration. The determined data may be sensor signal or data usability and the transition criteria may be a threshold level of sensor signal or data usability. The transition criteria may be further dependent on a decision support mode, the decision support mode may be selected from the group consisting of adjunctive (non-therapeutic), therapeutic (non-adjunctive), or a phase or mode of control in an artificial pancreas system. The transition criteria may be further dependent on data entered or received about a user or clinician use of information displayed by the monitoring device.

A decision support mode associated with the initial mode may be therapeutic and a decision support mode associated with the new mode may be adjunctive, and the determined data may be such that the sensor signal usability decreased below the threshold level of sensor signal usability associated with the transition criterion. The method may further include: prompting a user on a periodic basis to enter a calibration value from an external meter for blood glucose; and receiving the calibration value for blood glucose. The periodicity may be less in the new mode than in the initial mode.

A decision support mode associated with the initial mode may be adjunctive and a decision support mode associated with the new mode may be therapeutic, and the determined data may be such that the sensor signal usability increased above the threshold level of sensor signal usability associated with the transition criterion. The method may further include: prompting a user on a periodic basis to enter a calibration value for blood glucose; and receiving the calibration value for blood glucose. The periodicity may be greater in the new mode than in the initial mode.

The method may further include determining an intended mode of the monitoring device. The determining may include detecting whether a medicament delivery device is coupled to the monitoring device, and if so, configuring the monitoring device to a mode that is therapeutic. The determining may include: prompting a user to indicate an intended use of the monitoring device; receiving the indication; and configuring the monitoring device to a mode associated with the received indication. A number of blood glucose calibration readings required of the user may be based on the configured mode. Where the intended use is therapeutic, the method may further include configuring the monitoring device to a user-dependent calibration mode. Where the intended use is adjunctive, the method may further include configuring the monitoring device to a device self-calibration mode.

Where the initial mode is device self-calibration and the new mode is user-dependent calibration, the method may further include: prompting a user to enter a calibration value for blood glucose; receiving the calibration value for blood glucose; and using the received calibration value to inform the device self-calibration. The received calibration value may inform the device self-calibration by modifying the device self-calibration. The initial mode may be device self-calibration and the new mode may be user-dependent calibration, and the determined data and the transition criteria may include one or more parameters related to the usability of a signal from the sensor, where the one or more parameters are selected from the group consisting of: data from diagnostic routines indicating a shift in sensitivity; data entered by a user about a perceived error; data from a connected device; data from historic analyte values; time of day; a day of the week; whether a glucose value is high or low as compared to respective thresholds; a glucose urgency index; data about glucose concentration value variability; data about a level of user responsiveness; sensor signal value trajectory pre- and post-insertion of a new sensor; redundant or overlapping sensor data; user feedback on alerts and alarms; meal or exercise data as compared to predicted signal responses to meal or exercise data; data about a decision support mode configured for the monitoring device; or combinations of the above.

In the above, the data from diagnostic routines may include impedance data detecting shifts in sensitivity. The diagnostic routines may be performed on a periodic basis or upon detection of an error. The data entered by a user about a perceived error may include a blood glucose calibration value entered by a user in the absence of a prompt from the monitoring device, or a detection of a greater-than-average number of blood glucose calibration values entered by a user. The data from a connected device may include data from an external blood glucose meter. The initial mode may be device self-calibration and the new mode may be user-dependent calibration, and the method may further include: if the comparing indicates the determined data has met or will meet the transition criteria, then before the causing step, prompting a user to enter a reason for the determined data;

receiving the reason for the determined data; and based on the received reason, causing the monitoring device to maintain the initial mode of operation. The reason may be a user-perceived outlier, a user-perceived false alarm, or meal or exercise data.

The method may further include comparing the entered meal or exercise data to prior user-entered meal or exercise data, comparing a current signal to a signal associated with the prior user-entered meal or exercise data, and determining if the current signal and entered meal or exercise data are consistent with the prior signal and prior meal or exercise data. The initial mode may be device self-calibration and the new mode may be user-dependent calibration, and the method may further include: determining if a number of blood glucose measurements taken and entered into the monitoring device as calibration values exceed a predetermined threshold over a predetermined period of time, and if so, causing the monitoring device to transition to a user-dependent calibration mode.

The initial mode may be user-dependent and the new mode may be device self-calibration, the transition criteria may correspond to a level of confidence in the device self-calibration, and the method may further include: prompting a user to enter a calibration value for blood glucose, and using the entered value as the determined data; and if the comparing indicates the determined data meets the transition criteria, then performing the causing (a mode transition) step. The initial mode may be user-dependent calibration and the new mode may be device self-calibration, and the determined data and the transition criteria may correspond to the usability of entered blood glucose data, where the usability of entered blood glucose data corresponds to an accuracy, reliability, stability, or confidence in the blood glucose data. The method may further include confirming that entered blood glucose data is within a particular confidence interval or stability criterion, and if it is not, then performing the causing step. The method may further include confirming that entered blood glucose data is within an expected range based on an a priori or internal calibration, and if it is not, then performing the causing step.

The transition criteria may be based at least in part on a decision support mode in which the device is configured. The determined data and the transition criteria may indicate that the device continues to require external reference data for calibration, and the method may further include maintaining the initial mode. The determined data and the transition criteria may indicate that the device no longer requires external reference data for calibration, and the method may further include performing the causing step. The method may further include a package of sensors manufactured from the same lot, and the sensor may be a first of a plurality of sensors in the pack. In this case, the determined data and the transition criteria may indicate that the device no longer requires external reference data for calibration, and the method may further include: performing the causing step of causing the monitoring device to transition to a new mode of operation; and for subsequent sensors in the pack, initializing the device in device self-calibration mode, using one or more calibration settings associated with the first sensor.

The method may further include: initializing the monitoring device in two modes simultaneously, a first mode being user-dependent calibration and a second mode being device self-calibration; receiving and comparing two glucose concentration values, one glucose concentration value from the first mode and another glucose concentration value from the second mode; determining and displaying a glucose concentration value based on the two glucose concentration values; determining a level of confidence in the glucose concentration value from the second mode, using at least the two glucose concentration values; and once the determined level of confidence in the glucose concentration value from the second mode reaches a predetermined threshold, then only displaying the glucose concentration value from the second mode. The determining a level of confidence in the glucose concentration value from the second mode may include comparing at least the glucose concentration value from the second mode to a calibration value from an external meter.

The method may further include detecting a fault, and upon detection of the fault, displaying the glucose concentration value according to the first mode. The comparing may include comparing results of diagnostic tests or internal calibration information. The internal calibration information may be based on an impedance measurement. The predetermined threshold may be based at least in part on a decision support mode in which the device is configured. The comparing may include comparing slope and baseline information for the two modes. The comparing may further include: comparing errors in slope and baseline data for each of the two modes; and once the error in the slope or baseline for the second mode is equivalent to that in the first mode, then only displaying the glucose concentration value from the second mode. The comparing may further include determining slope and baseline information for each of the two modes with respective slope and baseline information for each of the two modes from a prior session. The method may further include displaying an indication of when a calibration value from an external meter is required.

The method may further include: initializing the monitoring device in two parallel modes, a first mode being user-dependent calibration and a second mode being device self-calibration; receiving and comparing two glucose concentration values, one glucose concentration value from the first mode and another glucose concentration value from the second mode; providing a weighting of the two glucose concentration values; and displaying a glucose concentration value according to the weighted glucose concentration values. The weighting may be proportional to the usability of the data determined by each of the modes. Once the weighting for a given mode reaches a predetermined threshold, the glucose concentration value displayed may be determined based on only the given mode.

In some implementations, the modes correspond to a mode of decision support. For example, the determined data may correspond to a sensor signal, and the transition criteria may correspond at least to a usability of the sensor signal. The transition criteria may be at least in part based on the initial mode of operation. The initial mode may be a therapeutic mode, and the new mode may be an adjunctive mode. The displaying in the new mode of operation may further include, while in the adjunctive mode, displaying data to a user in such a way as to indicate its usability adjunctively. The displaying in the new mode of operation may further include indicating the usability of the data by displaying a zone or range of glycemic data instead of a single value. The displaying in the new mode of operation may further include requiring the user to clear a prompt before displaying a subsequent glucose concentration value or a range of glucose concentration values. The usability may be indicated by colors and/or flashing numerals and/or a dot size on a trend graph. The displaying in the new mode of operation may further include restricting displayed data to only a rate of change arrow and not a glucose concentration value. The usability may be indicated by a displayed change in a prediction horizon. The displaying in the new mode of operation may further include, while in the therapeutic mode, displaying data to a user in such a way as to indicate its usability therapeutically. The displaying in the new mode of operation may further include indicating the usability of the data by displaying a determined single value of glucose concentration. The usability may be indicated by a displayed change in a prediction horizon. The usability may be indicated by colors and/or flashing numerals and/or a dot size on a trend graph. The transition criteria may be further at least partially based on time of day or day of week. The usability of the sensor signal may be based on one or more parameters selected from the group consisting of: a user response to a query about a perceived accuracy or perceived user glucose range; data about likelihood of a potential fault or failure mode; data about glucose context; a user response to a query about a glycemic event; a user response to a query about a potential false alarm; a confirmatory meter reading requested of a user via a displayed prompt; a calibration mode; a data transmission mode; a user indication of desired monitoring device responsiveness; or combinations of the above.

The method may further include changing a calibration mode along with the change from the initial to the new mode of operation. The method may further include transmitting a signal to a medicament delivery pump. The new mode may be therapeutic, and the signal may instruct the pump to receive and follow signals from the monitoring device. The new mode may be adjunctive, and the signal may instruct the pump to disregard received signals from the monitoring device. The new mode may be therapeutic, and the signal may instruct the pump to receive and follow signals from the monitoring device to control the user glucose concentration value to a target value. The new mode may be therapeutic, and the signal may instruct the pump to receive and follow signals from the monitoring device to control the user glucose concentration value to a target range of values. The new mode may be therapeutic, and the signal may instruct the pump to receive and follow signals from the monitoring device to control the user glucose concentration value only when the glucose concentration value is below a predetermined value, above a predetermined value, or within a predetermined range of values.

The initial mode may be adjunctive and the new mode may be therapeutic, and in the new mode the monitoring device may be configured to calculate a recommended insulin bolus and the displaying on the user interface may further include displaying the calculated recommended insulin bolus without a calibration meter reading, and in the initial mode the monitoring device may be configured to not calculate and display a recommended insulin bolus without a calibration meter reading. Upon a step of sensor start up, the initial mode may be adjunctive, and the displaying indicating the new mode of operation may further include displaying low-resolution data.

The method may further include determining a level of confidence in the sensor over a period of time, and once the measured level of confidence has reached a predetermined threshold, the method may further include the step of displaying high-resolution data and causing a transition to a therapeutic mode. The determining a level of confidence may include receiving an external blood glucose meter reading. The external blood glucose meter reading may correlate to what the monitoring device estimates the glucose concentration value to be or may be used to calibrate the monitoring device. The method may further include configuring the monitoring device to enter a user-dependent calibration mode of operation. The method may further include receiving an external blood glucose meter reading, developing a level of confidence in the sensor over a period of time, and once the level of confidence has reached a predetermined threshold, causing the monitoring device to enter a user-dependent calibration mode of operation.

The monitoring device may operate in two modes of operation concurrently, one adjunctive and one therapeutic, and the displaying may further include displaying an initial splash screen with data displayed in the adjunctive mode of operation. Upon receiving a selection from a user interface for data requiring a new mode of operation, the method may further include causing a transition to the new mode of operation, receiving one or more data values required by the new mode of operation, and displaying the data using the new mode of operation. The selected data may include a hypoglycemic safety alarm, and the new mode of operation may be user-dependent calibration.

Certain implementations of the embodiments may pertain to transmission modes. For example, the determined data may include data based on a glucose concentration value, and the transition criteria may be selected from the group consisting of: a glycemic state threshold, a GUI threshold, a glucose threshold, a glucose rate of change threshold, a glucose acceleration threshold, a predicted value of glucose or any of its rates of change, an excursion beyond a predetermined threshold, an alert criteria, a criteria for a glycemic danger zone, or a combination of the above.

The transition criteria may be selected from the group consisting of: a duration of time since a user last requested a glucose concentration value, a decision support mode, a user response to a query, a calibration mode of the monitoring device, or a combination of the above. The determining data may include transmitting a signal to cause a sensor to send a glucose concentration value. The determining data may include receiving a signal from a sensor corresponding to a glucose concentration value. The initial mode may be on-demand transmission, the new mode may be device-initiated transmission, the determined data may be a glucose concentration value, and the transition criteria may be the glucose concentration value being in a dangerous range for a period exceeding a first predetermined duration of time.

The method may further include displaying an alert to the user on a user interface of the monitoring device until the user performs an action of responding to the alert. The initial mode may be device-initiated transmission, the new mode may be on-demand transmission, the determined data may be a glucose concentration value, and the transition criteria may be the glucose concentration value being in a dangerous range for a period exceeding a second predetermined duration of time.

In another aspect, the embodiments are directed towards a system for performing any of the above methods. In another aspect, the embodiments are directed towards a device or system or method substantially as shown and/or described in the specification and/or drawings.

In another aspect, the embodiments are directed towards an electronic device for monitoring data associated with a physiological condition, including: a continuous analyte sensor, where the continuous analyte sensor is configured to substantially continuously measure the concentration of analyte (such as glucose) in the host, and to provide continuous sensor data indicative of the analyte concentration in the host; and a processor module configured to perform any one of the described methods.

In another aspect, the embodiments are directed towards an electronic device for delivering a medicament to a host, the device including: a medicament delivery device configured to deliver medicament to the host, where the medicament delivery device is operably connected to a continuous analyte sensor, where the continuous analyte sensor is configured to substantially continuously measure the concentration of analyte (such as glucose) in the host, and to provide continuous sensor data indicative of the analyte concentration in the host; and a processor module configured to perform any one of the described methods.

To ease the understanding of the described features, continuous glucose monitoring is used as part of the explanations that follow. It will be appreciated that the systems and methods described are applicable to other continuous monitoring systems, e.g., for analysis and monitoring of other analytes, as will be noted in greater detail below.

Any of the features of embodiments of the various aspects disclosed is applicable to all aspects and embodiments identified. Moreover, any of the features of an embodiment is independently combinable, partly or wholly with other embodiments described herein, in any way, e.g., one, two, or three or more embodiments may be combinable in whole or in part. Further, any of the features of an embodiment of the various aspects may be made optional to other aspects or embodiments. Any aspect or embodiment of a method can be performed by a system or apparatus of another aspect or embodiment, and any aspect or embodiment of the system can be configured to perform a method of another aspect or embodiment.

Advantages may include, in certain embodiments, one or more of the following. Continuous analyte monitoring may be made more adaptable to a given situation, requiring less user interaction or input when such is not required, enhancing usability and user friendliness of a monitoring device. Other advantages will be understood from the description that follows, including the figures and claims.

Any of the features of embodiments of the various aspects disclosed is applicable to all aspects and embodiments identified. Moreover, any of the features of an embodiment is independently combinable, partly or wholly with other embodiments described herein, in any way, e.g., one, two, or three or more embodiments may be combinable in whole or in part. Further, any of the features of an embodiment of the various aspects may be made optional to other aspects or embodiments. Any aspect or embodiment of a method can be performed by a system or apparatus of another aspect or embodiment, and any aspect or embodiment of the system can be configured to perform a method of another aspect or embodiment.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The present embodiments now will be discussed in detail with an emphasis on highlighting the advantageous features. These embodiments depict the novel and non-obvious mode switching systems and methods according to present principles, for use in analyte monitoring and other purposes, shown in the accompanying drawings, which are for illustrative purposes only. These drawings include the following figures, in which like numerals indicate like parts.

Like reference numerals refer to like elements throughout. Elements are not to scale unless otherwise noted.

DETAILED DESCRIPTION

Definitions

Figure 1:
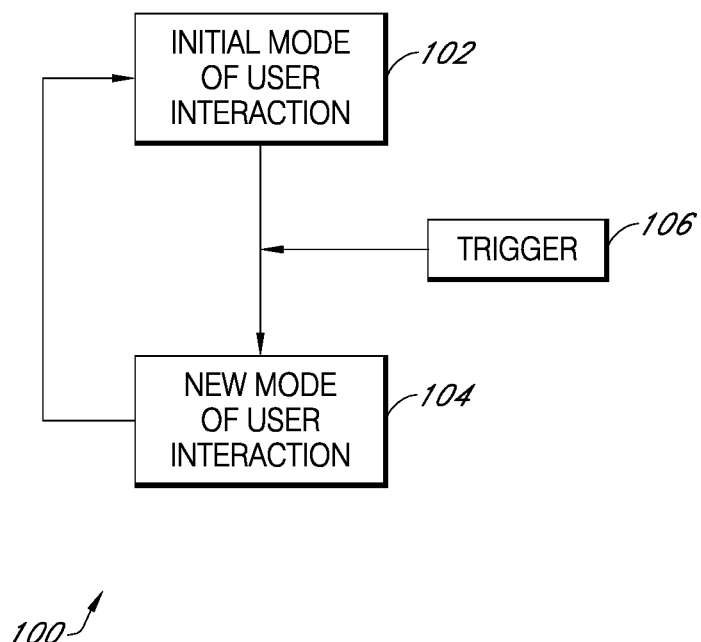
FIG. 1 is a flowchart according to present principles showing one implementation of a general method of mode switching.

In order to facilitate an understanding of the preferred embodiments, a number of terms are defined below.

The term "analyte" as used herein generally relates to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sisomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, rickettsia (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "calibration" as used herein generally relates to the process of determining the relationship between the sensor data and the corresponding reference data, which can be used to convert sensor data into meaningful values substantially equivalent to the reference data, with or without utilizing reference data in real time. In some embodiments, namely, in continuous analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein generally relate to data that has been transformed from its raw state (e.g., digital or analog) to another state using a function, for example a conversion function, to provide a meaningful value to a user.

The term "algorithm" as used herein generally relates to a computational process (for example, programs) involved in transforming information from one state to another, for example, by using computer processing.

The term "counts" as used herein generally relates to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein generally relates to the component or region of a device by which an analyte can be quantified.

The terms "glucose sensor" and "member for determining the amount of glucose in a biological sample" as used herein generally relate to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

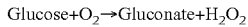

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein generally relate to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The terms "in vivo portion" as used herein generally relates to the portion of the device (for example, a sensor) adapted for insertion into and/or existence within a living body of a host.

The terms "reference analyte monitor," "reference analyte meter," and "reference analyte sensor" as used herein generally relate to a device that measures a concentration of an analyte and can be used as a reference for the continuous analyte sensor, for example a self-monitoring blood glucose meter (SHBG) can be used as a reference for a continuous glucose sensor for comparison, calibration, and the like.

The term "system noise" as used herein generally relates to unwanted electronic or diffusion-related noise which can include Gaussian, motion-related, flicker, kinetic, or other white noise, for example.

The terms "noise," "noise event(s)," "noise episode(s)," "signal artifact(s)," "signal artifact event(s)," and "signal artifact episode(s)" as used herein generally relate to signal noise that is caused by substantially non-glucose related, such as interfering species, macro- or micro-motion, ischemia, pH changes, temperature changes, pressure, stress, or even unknown sources of mechanical, electrical and/or biochemical noise for example. In some embodiments, signal artifacts are transient and characterized by a higher amplitude than system noise, and described as "transient non-glucose related signal artifact(s) that have a higher amplitude than system noise." In some embodiments, noise is caused by rate-limiting (or rate-increasing) phenomena. In some circumstances, the source of the noise is unknown.

The terms "constant noise" and "constant background" as used herein generally relate to the component of the noise signal that remains relatively constant over time. In some embodiments, constant noise may be referred to as "background" or "baseline." For example, certain electroactive compounds found in the human body are relatively constant factors (e.g., baseline of the host's physiology). In some circumstances, constant background noise can slowly drift over time (e.g., increase or decrease), however this drift need not adversely affect the accuracy of a sensor, for example, because a sensor can be calibrated and re-calibrated and/or the drift measured and compensated for.

The terms "non-constant noise," "non-constant background," "noise event(s)," "noise episode(s)," "signal artifact(s)," "signal artifact event(s)," and "signal artifact episode(s)" as used herein generally relate to a component of the background signal that is relatively non-constant, for example, transient and/or intermittent. For example, certain electroactive compounds, are relatively non-constant due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The terms "low noise" as used herein generally relates to noise that substantially decreases signal amplitude.

The terms "high noise" and "high spikes" as used herein generally relate to noise that substantially increases signal amplitude.

The term "variation" as used herein generally relates to a divergence or amount of change from a point, line, or set of data. In one embodiment, estimated analyte values can have a variation including a range of values outside of the estimated analyte values that represent a range of possibilities based on known physiological patterns, for example.

The terms "physiological parameters" and "physiological boundaries" as used herein generally relate to the parameters obtained from continuous studies of physiological data in humans and/or animals. For example, a maximal sustained rate of change of glucose in humans of about 4 to 5 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (for example, about 20 to 30 minutes) is a straight line, which can be used to set physiological limits. These terms are broad enough to include physiological parameters for any analyte.

The term "measured analyte values" as used herein generally relates to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein generally relates to an analyte value or set of analyte values, which have been algorithmically extrapolated from measured analyte values.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

The phrase "continuous glucose sensor" as used herein generally relates to a device that continuously or continually measures the glucose concentration of a bodily fluid (e.g., blood, plasma, interstitial fluid and the like), for example, at time intervals ranging from fractions of a second up to, for example, 1, 2, or 5 minutes, or longer.

The phrases "continuous glucose sensing" or "continuous glucose monitoring" as used herein generally relate to the period in which monitoring of the glucose concentration of a host's bodily fluid (e.g., blood, serum, plasma, extracellular fluid, tears etc.) is continuously or continually performed, for example, at time intervals ranging from fractions of a second up to, for example, 1, 2, or 5 minutes, or longer. In one exemplary embodiment, the glucose concentration of a host's extracellular fluid is measured every 1, 2, 5, 10, 20, 30, 40, 50 or 60 seconds.

The term "substantially" as used herein generally relates to being largely but not necessarily wholly that which is specified, which may include an amount greater than 50 percent, an amount greater than 60 percent, an amount greater than 70 percent, an amount greater than 80 percent, an amount greater than 90 percent, or more.

The terms "processor" and "processor module," as used herein generally relate to a computer system, state machine, processor, or the like, designed to perform arithmetic or logic operations using logic circuitry that responds to and processes the basic instructions that drive a computer. In some embodiments, the terms can include ROM and/or RAM associated therewith.

The terms "usability", "data usability", and "signal usability", as used herein generally relate to accuracy, reliability, and/or confidence in sensor data. In some cases such terms may also relate to stability of the sensor data.

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor capable of measuring the concentration of glucose in a host, the systems and methods of embodiments can be applied to any measurable analyte. Some exemplary embodiments described below utilize an implantable glucose sensor. However, it should be understood that the devices and methods described herein can be applied to any device capable of detecting a concentration of analyte and providing an output signal that represents the concentration of the analyte.

In some embodiments, the analyte sensor is an implantable glucose sensor, such as described with reference to U.S. Pat. Nos. 6,001,067 and 8,828,201. In some embodiments, the analyte sensor is a transcutaneous glucose sensor, such as described with reference to U.S. Pat. No. 7,497,827. In yet other embodiments, the analyte sensor is a dual electrode analyte sensor, such as described with reference to U.S. Pat. No. 8,478,377. In still other embodiments, the sensor is configured to be implanted in a host vessel or extracorporeally, such as is described in U.S. Pat. No. 7,460,898. These patents and publications are incorporated herein by reference in their entirety.

The following description and examples describe the present embodiments with reference to the drawings. In the drawings, reference numbers label elements of the present embodiments. These reference numbers are reproduced below in connection with the discussion of the corresponding drawing features.

In general, systems and methods according to present principles relate to real time switching between a first or initial mode of user interaction and a second or new mode of user interaction. In some cases, users may confirm such switching before it occurs, or may be notified about the same. In many cases, however, the switching will be automatic and transparent to the user. The mode switching may cause a switch from an initial mode to a new mode, followed by a switch to a subsequent mode or back to the initial mode. In any case, the mode switching will generally affect the user's interaction with the device, and not just cause internal processing changes within the device, although such processing changes will generally accompany the mode switching. Such user interaction with the device may generally affect how the user calibrates the monitoring device, views and uses the data, or the like. The mode switching may generally have a significant effect on the user interaction as embodied in the user interface, including aspects from both the input and the output. B In many cases the decision or trigger to switch between modes relates to a usability of the monitoring device which is in many cases (but not always) related to the usability of a sensor signal, as compared to a transition criteria, but may also be based on other data.

For example, referring to the flowchart 100 of FIG. 1, a monitoring device may start in a first, original, or initial mode of operation or user interaction 102. Upon the occurrence of a trigger 106, the monitoring device may switch to a second or new mode of operation or interaction 104. The trigger 106 generally comes about when one or more trigger criteria are met, e.g., when one or more values of determined data meets, or is predicted to meet, one or more respective predetermined threshold transition criteria. One type of criterion used in some implementations is data or signal usability, but other data and accompanying criteria are also often used.

As one example, an analyte monitoring device may transition or switch from a user-dependent calibration mode to a device self-calibration mode, i.e., from a calibration routine using blood glucose concentration values from an external meter to a calibration routine performed by the device it without requiring a user to provide a glucose value from, e.g., a self-monitoring blood glucose meter. Device self-calibration generally requires one or more of stringent manufacturing controls, internal measurements, entry of calibration codes from the manufacturer (which themselves constitute a priori information) and/or associated algorithms that enable calibration of the device without external measurement obtained during sensor wear.

Additional details of systems and methods for device self-calibration are disclosed in U.S. patent application Ser. No. 13/827,119; and US Patent Publication No. 2012/0265035-A1, both of which are owned by the assignee of the present application and herein incorporated by reference in their entireties.

The converse transition or switch may also be performed. As another example, an analyte monitoring device may transition or switch from providing information or data on-demand to a user to a mode in which information or data is provided as initiated by the device, e.g., as a regular or irregular periodic communication. The converse transition or switch may also be performed. As yet another example, an analyte monitoring device may transition or switch from providing information or data in one decision-support mode to another, e.g., from a therapeutic (or non-adjunctive) use to an adjunctive (or non-therapeutic) use or from one phase of control to another. Again, the converse transition or switch may also be performed, as well as transitions or switches to other modes.

A number of triggers will be described, and generally the triggers are such that one or more criteria are met or satisfied. In one common type of criteria, a determined parameter or variable meets or exceeds a predetermined threshold, or is determined to do so in the future. The determined parameter or variable may be data associated with the sensor signal, i.e., the sensor signal value or a scaled representative thereof, data about the sensor signal, e.g., data indicating its noise level or the like, data from an external source, e.g., data from a blood glucose meter, temperature sensor, clock, location sensor, or the like, as well as other data as will be described below.

Systems and methods according to present principles may use one or many triggers, i.e., transition criteria, on which to base mode switching for a given implementation. In some cases, for specific types of mode switching, particular determined parameters or variables will be especially useful. For example, signal usability may be especially pertinent when deciding and switching calibration modes or decision-support modes. The signal value itself may be especially pertinent when deciding data transmission modes, e.g., whether a large excursion has occurred. However, these are purely exemplary and it will be understood that in given implementations other criteria will prove useful. It will further be understood that in any given implementation any number or type of transition criteria may be employed, including in some cases a single criterion.

Figure 2:
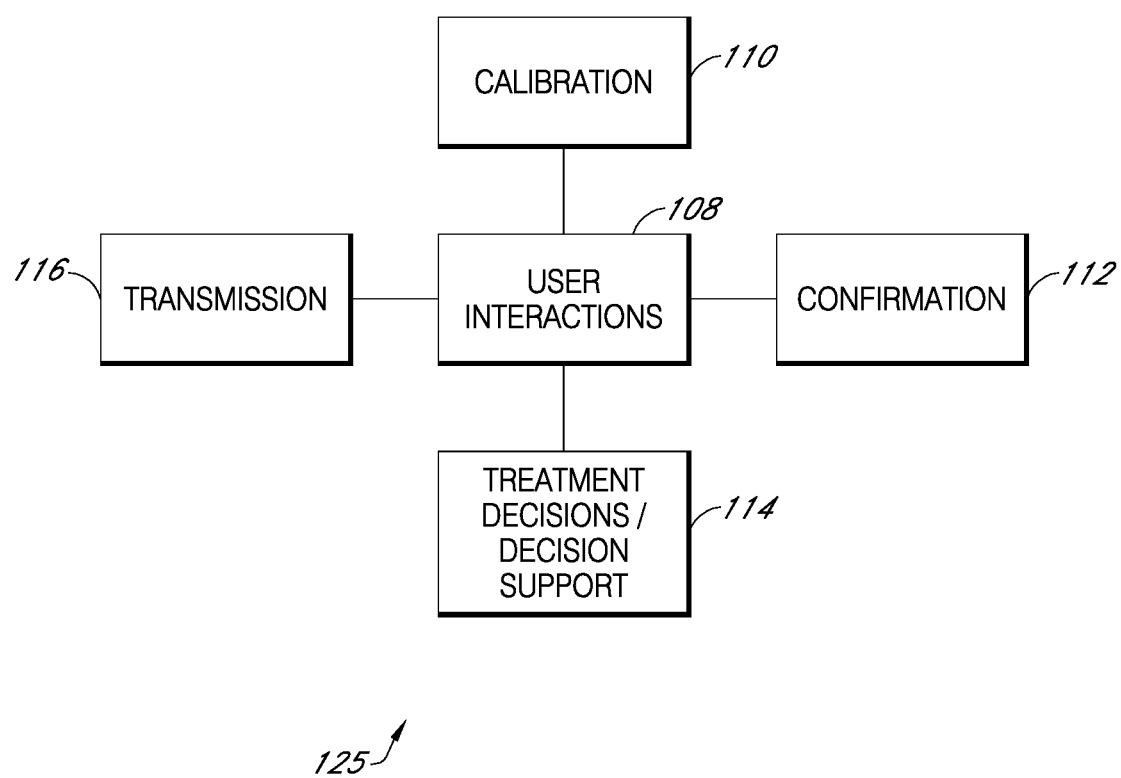
FIG. 2 is a diagram according to present principles showing types of user interactions.

FIG. 2 shows a diagram 125 illustrating a number of types of user interactions 108, which may be identified with modes of user interaction. For example, and as noted above, one variety of user interactions 108 which may be subject to mode switching involves a calibration mode 110. Calibration modes may include user-dependent calibration, device self-calibration, and so on. The calibration mode may be in part dependent on data usability, as well as on other data.

Another type of user interaction 108 involves the use to which the user will put the data, such as the use of the data in a decision-support mode 114. Exemplary uses include therapeutic, where the monitoring device is used in the calculation and/or to direct delivery of insulin, or adjunctive, where the monitoring device is used for information but where insulin dosing is based on external user calculations and/or a confirmatory external meter value, e.g., from a blood glucose meter. If the use is directly related to patient health, e.g., therapeutic, then the requirements of the signal will generally be higher than if not. Thus, lower signal usabilities (less reliable data) may result in transitions from therapeutic to adjunctive modes. Some decision-support modes include modes used only for information or augmentation of education, e.g., tracking and trending, as well as (on the other extreme) "closed-loop" modes in which data from the monitoring device is directly used to drive a medicament delivery pump.

In the context of Type I diabetes, the terms "non-therapeutic" and "adjunctive" may be used interchangeably or as synonyms, similarly the terms "therapeutic" and "non-adjunctive" may also be used interchangeably or as synonyms. The terms therapeutic (non-adjunctive) and adjunctive (non-therapeutic) are used in a relative sense, and it should be noted that the terms may have different connotations for other health indication that may be dependent upon populations and/or technology. For example, for a type I user, a therapeutic or non-adjunctive mode may mean one in which the user receives dosing recommendations, while an adjunctive or non-therapeutic mode may refer to one in which recommendations are given but the same do not relate to insulin dosing. The descriptions herein may be primarily directed towards a usage of the terms "therapeutic" and "adjunctive" as pertaining to delivery of therapy such as insulin dosing for type I diabetics. However, the same terms or similar may be employed for other populations. For example, for type II users or for those interested in health or fitness optimization, a therapeutic use may be one in which a meal or exercise is suggested, while an adjunctive use is one in which information is delivered without a specific recommendation associated therewith.

In health indications other than Type I diabetes, the terms "non-therapeutic" and "adjunctive" have meanings that are overlapping, but not necessarily identical; similarly, the terms "therapeutic" and "non-adjunctive" have meanings that are overlapping, but not necessarily identical. In the example of a type II user, or a user with a general interest in food or exercise optimization, a therapeutic mode may mean one in which the user receives food and exercise recommendations, while an non-therapeutic mode may refer to one in which information is provided to the user, without any specific recommendations. For example, such a user may include those with interests in optimizing sports or fitness routines or eating habits, users interested in losing weight or otherwise increasing their health, or indeed any other user interested in bettering their health or learning more about how their habits and actions affect their health. For these users, therapeutic recommendations may include suggested meals, foods, or recipes, based on data known by the system including glucose value, glucose rate of change, activity level, sleeping patterns, and the like. For users particularly interested in fitness optimization, data may be employed such as activity data, such as may be received from an accelerometer or GPS device. Such optimization routines may also include data gained from CGM including glucose, glucose rate of change, and the like. Informational or adjunctive data may be provided, e.g., total calories burned that day, and so on.

Additional details about type II user recommendations may be found in co-pending U.S. Provisional Patent Application Ser. No. 62/158,463, owned by the assignee of the present application and herein incorporated by reference in its entirety.

Figure 15A:
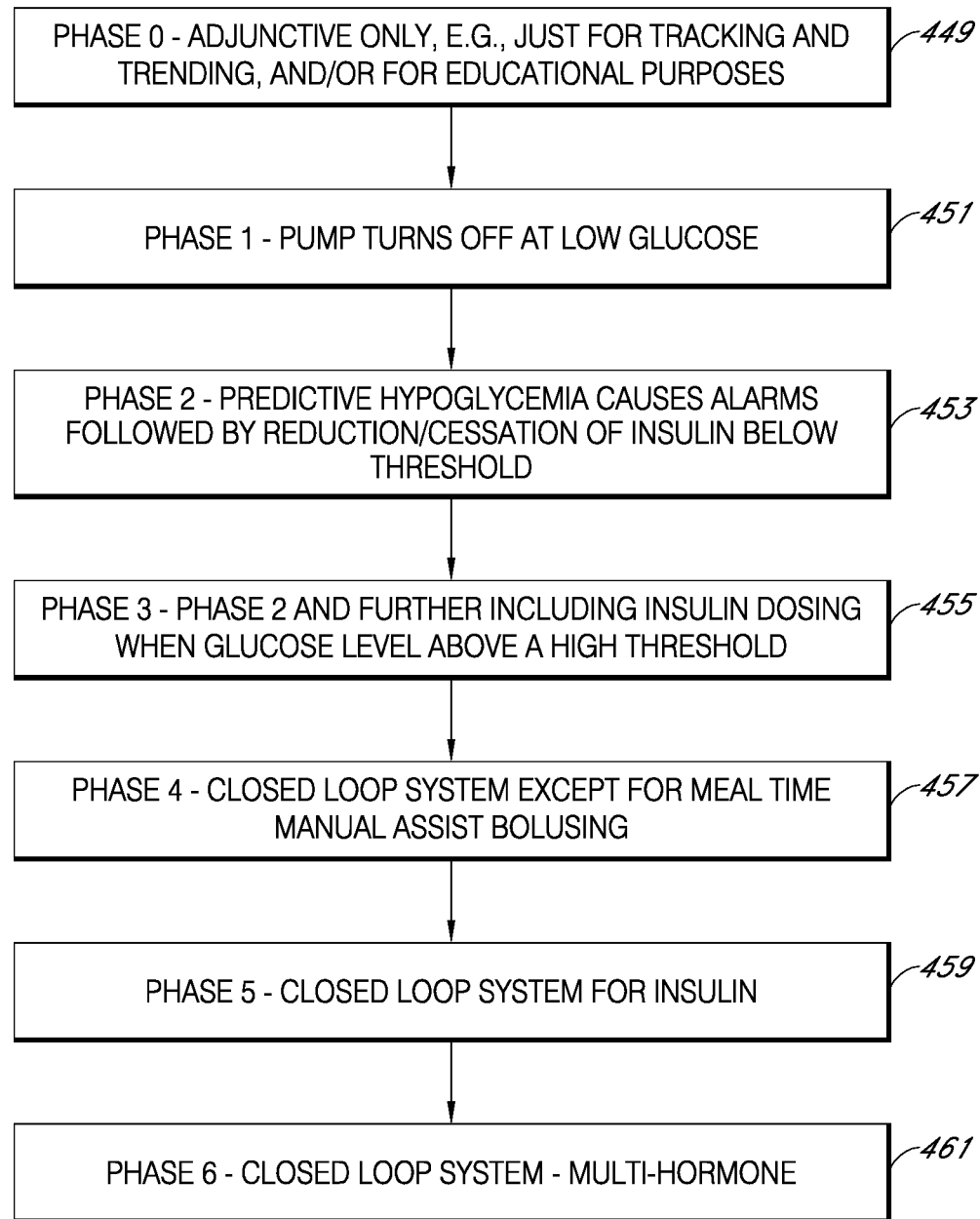
FIG. 15A illustrates a progressive sequence of modes, phases, or stages, detailing levels or phases of control within an artificial pancreas system.

More generally, an analyte monitoring device may be configured to switch between different modes or phases of an artificial pancreas system as illustrated in FIG. 15A.

Yet another type of user interaction involves the mode 110 in which transmission of the data from the sensor electronics to the monitoring device occurs. If data is pulled on-demand by the monitoring device from the sensor or accompanying sensor electronics, then such is termed an on-demand mode, while if the data is pushed periodically or upon occurrence of an event, such is termed a device self-initiated mode.

Yet another type of user interaction mode is a confirmation mode 112. This mode may be considered separately from the modes above, but often plays a role in the implementation of one of the other modes. In this mode, a user is prompted by a confirmatory prompt or query prior to a mode switch or in some cases prior to a change within a particular mode. For example, prior to switching from device self-calibration mode to user-dependent calibration mode, the user may be prompted to confirm that they understand that finger sticks will now be required.

Figure 3A:
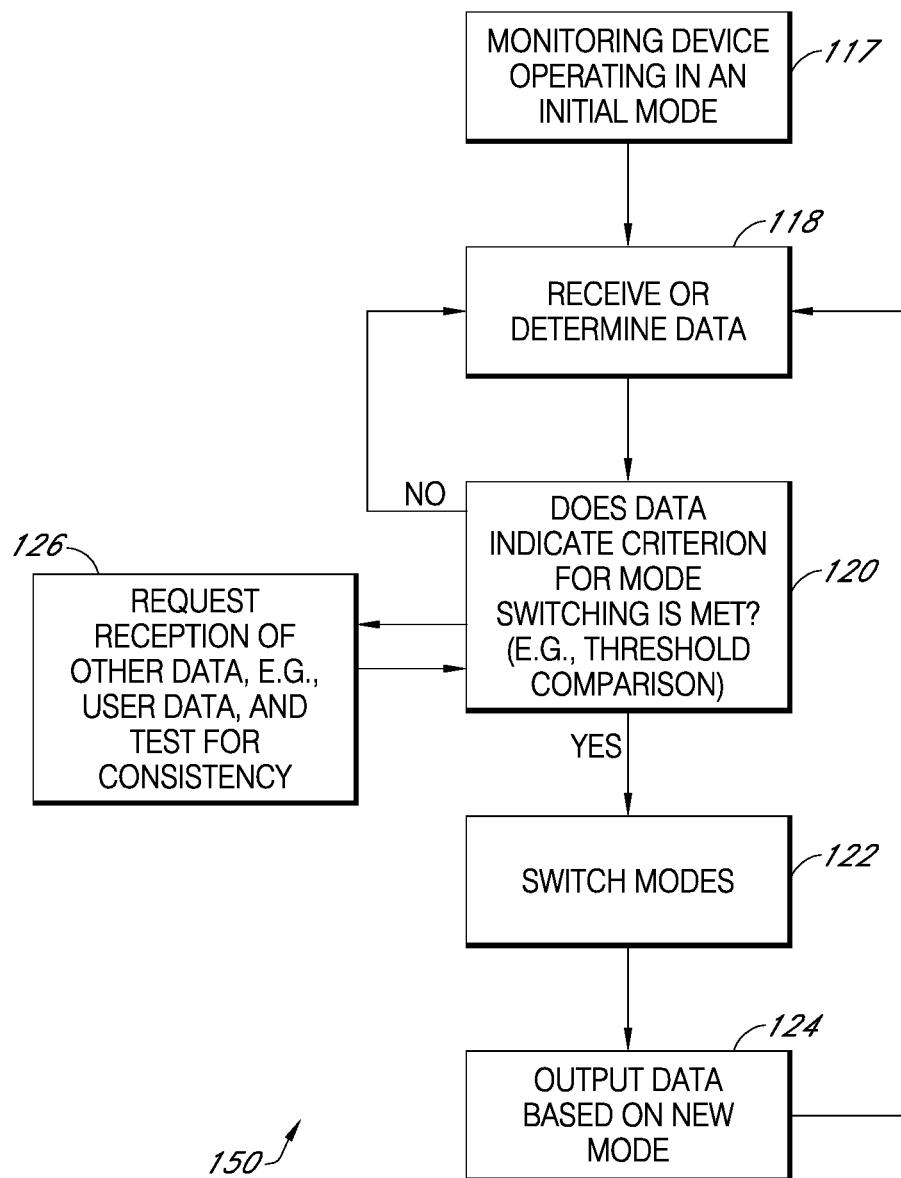
FIG. 3A-3C are flowcharts according to present principles showing other implementations of general methods of mode switching.

The flowchart 150 of FIG. 3A indicates a general method for mode switching. In a first step, the monitoring device is operating in an initial mode (step 117). The monitoring device may have started following power up in the initial mode, or may have switched to the mode using systems and methods similar to those disclosed here. A next step is that data is received or otherwise determined (step 118). The data that is received or otherwise determined as discussed in greater detail below, but generally relates to a data signal from the sensor, a data quality parameter associated with the data signal from the sensor using signal analysis, external data, or the like. A next step is to check if the data received or determined is such that that a criterion for mode switching is met (step 120). In other words, the received or determined data is checked to see if the same should cause a switch of modes, e.g., whether it meets, matches, or satisfies certain criteria, e.g., meets or exceeds a threshold for a transition criteria.

Of course, it will be understood that different transition criteria may be satisfied or met by different determined data in any given situation, and the satisfaction of a criteria for one type of transition may be accompanied by other concurrent or overlapping mode switching steps.

Figure 3B:
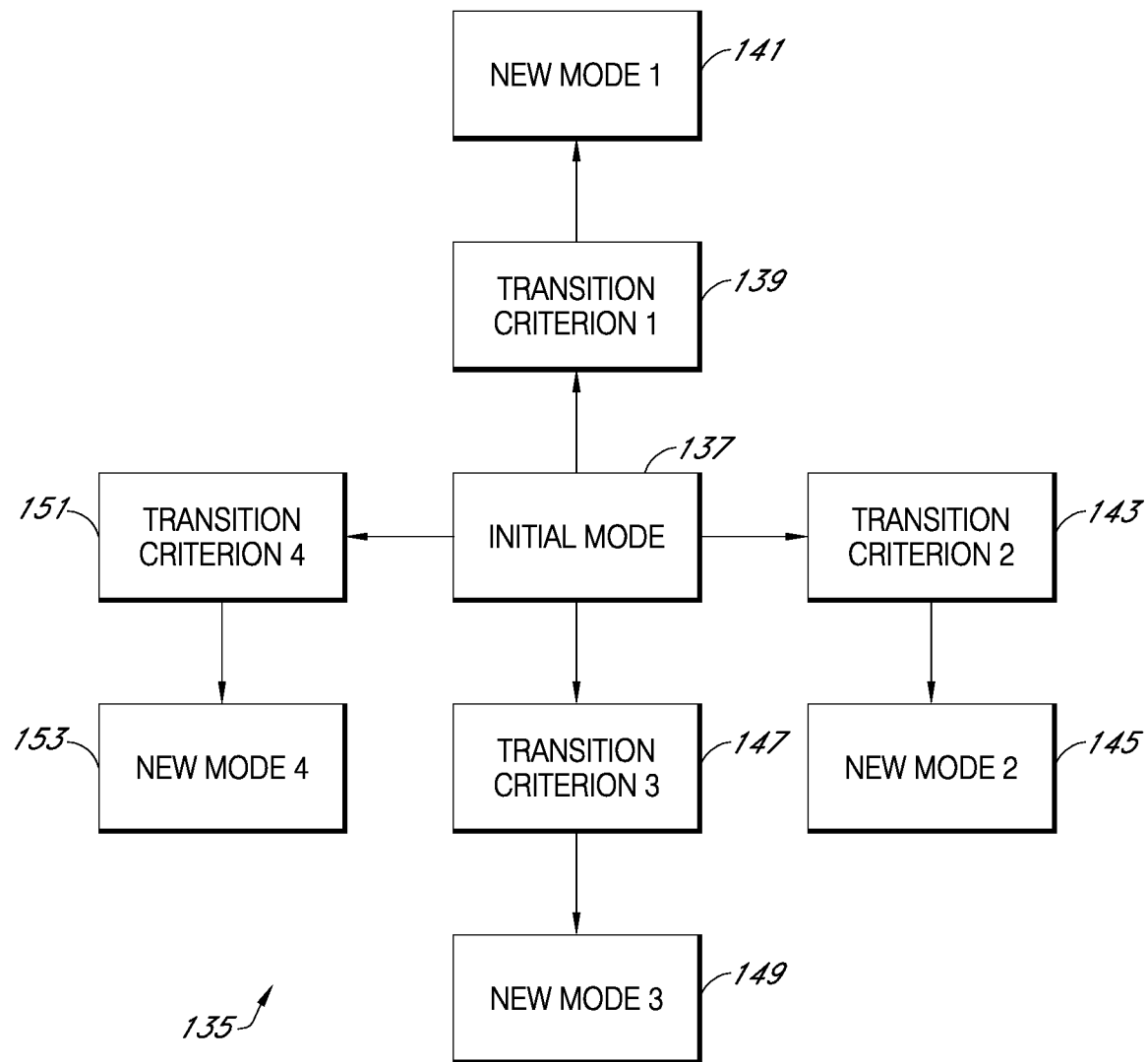

This situation is illustrated in FIG. 3B, in which an initial mode 137 may be caused to transition to a first new mode 141 if a first transition criterion 139 is met by a determined parameter or variable, and in the same way the initial mode 137 may be caused to transition to a second new mode 145 if a second transition criterion 143 is met, and so on for transitions to modes 149 and 153 caused by the meeting of transition criteria 147 and 151, respectively. For example, a device may switch to a user dependent calibration mode and may simultaneously (or not) transition to a therapeutic mode. Exemplary such multimodal transitions are described in greater detail below.

Figure 3C:
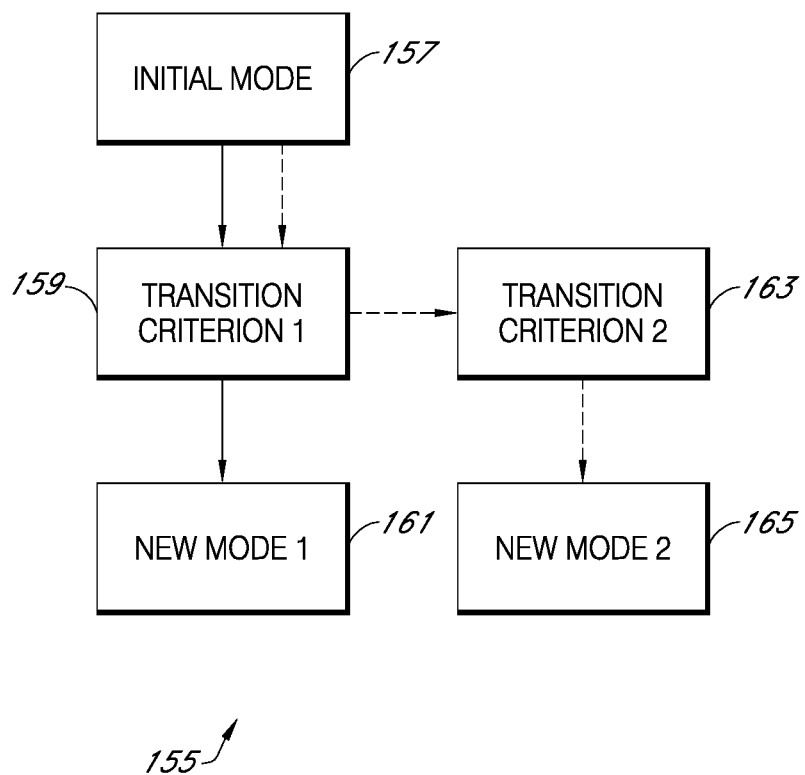

The meeting of multiple transition criteria may result in a different mode being transitioned to as compared to the case where just one transition criterion is met. This situation is illustrated in the flowchart 155 of FIG. 3C. An initial mode 157 can transition to a new mode 161 upon the meeting of a first transition criterion 159 (solid lines). However, an initial mode 157 can also transition to a second new mode 165 upon the meeting of both a first transition criterion 159 and a second transition criterion 163 (dotted lines).

Figure 4:
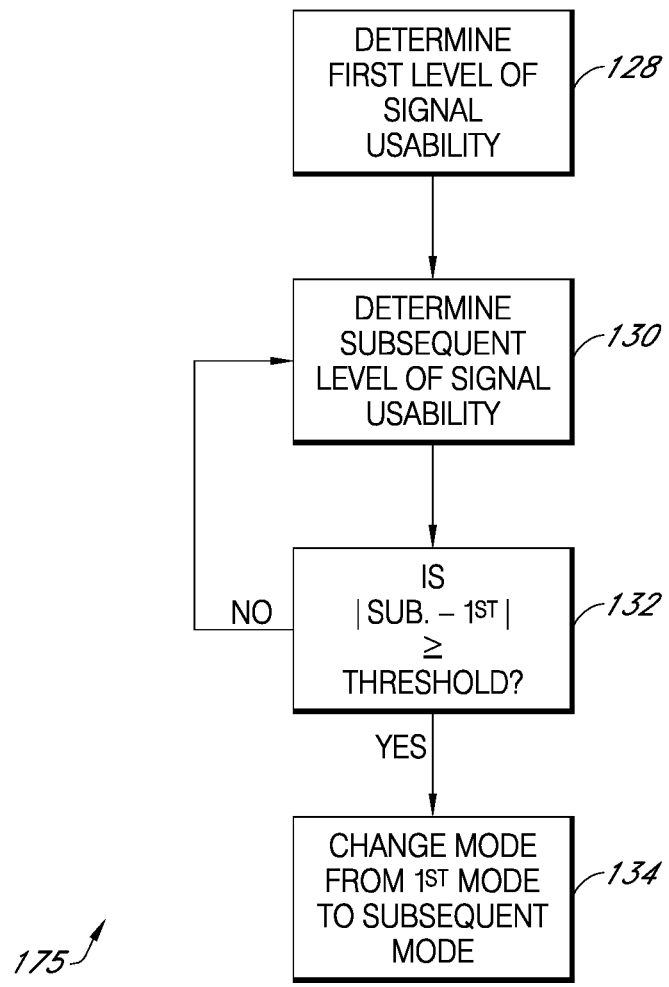
FIG. 4 is a flowchart according to present principles showing another implementation of a method of mode switching, based on comparing signal or data usability to one or more criteria such as a threshold.

As noted above, in many cases a "determined data" that is compared to a transition criterion will relate to data or signal usability. In a specific method using such, as illustrated by the flowchart 175 of FIG. 4, in a first step, a first level of signal usability is determined (step 128). It is assumed that the first level of signal usability does not result in a switch or transition of modes. A subsequent determination is made of a level of signal usability (step 130), and if the subsequent level of signal usability is sufficiently different from the first level (step 132), i.e., satisfies a transition criteria, e.g., is greater than or equal to a threshold level of difference, then the mode may be changed from the initial mode to a subsequent mode (step 134). That is, the mode may switch depending on whether the evaluation determined that the criteria (or criterion) for mode switching was met.

If the subsequent level of signal usability is not sufficiently different, then the cycle may begin again. In a related implementation, the signal usability need not be measured against a prior measured level, but may simply be compared to a criterion based on an absolute standard. If the signal usability varies from the absolute standard by greater than a predetermined threshold amount, the transition to the new mode may again occur.

In any case, data is output on a user interface based on the mode determined, e.g., either the initial mode or the new mode. In some implementations it may be useful to indicate to the user how long a new mode is expected to last, e.g., whether the same is transient or long-term. As an example, if a decision-support mode switches from therapeutic to adjunctive, due to a sensor fault that is transient, e.g., a dip and recover fault, the user may be informed that the adjunctive use is temporary and should last for less than about one day. As another example, in calibration modes, if there is full confidence in the device self-calibration, then the device may indicate that no additional blood glucose meter values may be required for the remainder of the sensor session. Similarly, in addition to selectively outputting based on the mode, and providing an indication of the mode, the UI may display a performance indicator for how well the sensor is performing.

Specific triggering or transition criteria are now described, and it is noted that such may be applied to certain or all embodiments noted herein. The criteria may be used individually, as part of a single-mode or single-variable transition, or multiple criteria and data may be monitored and compared simultaneously or at nearly the same time, enabling multimodal transitions, e.g., causing a change in calibration type and a change in decision support mode. The embodiments described herein in which the below criteria may be employed include, e.g., the general transitions noted in FIGS. 1, 3A, 3B, 3C, and 10, the transitions noted in FIGS. 2, 9, 11-17, 20 and 21A, the specific use of criteria related to data usability in FIG. 4, including the use of thresholds, and the criteria may be applied to the specific types of data described in FIGS. 5-8, with results as displayed in FIGS. 18A-18D and 24.

Figure 5:
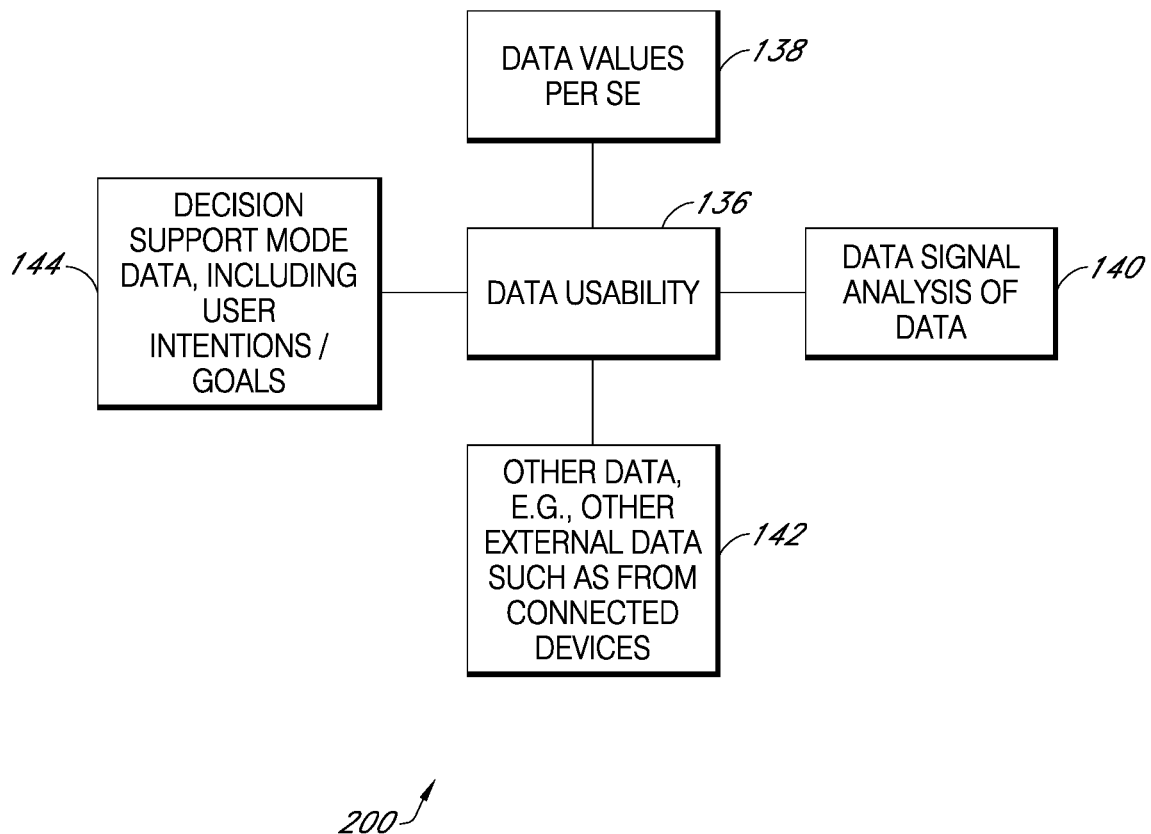
FIG. 5 is a diagram according to present principles showing aspects of data usability.

Referring to the diagram 200 of FIG. 5, a parameter or variable 136 relating to the data usability may be considered to occupy one or more of a number of categories. The parameter or variable 136 may also be based on a combination of contributions from these categories, e.g., a linear or nonlinear combination, and in some implementations with weightings applied.

One category of data on which the data usability 136 may be based is on the data values per se 138. This category generally relates to sensor signal values as well as scaled or normalized representations of these values, e.g., where the first is measured in an analog or digital value (e.g., counts) and the second is often measured by a concentration such as mg/dL. It may also relate to data based on such values, e.g., time rates of change, determined patterns, historical values, excursions, and the like. In some cases fault data may be used in the calculation of data usability as the same may be based on data values per se.

Another category of data on which the data usability 136 may be based is on data signal analysis 140. The data signal analysis 140 pertains to data about the received signal, e.g., noise levels, variability, in some cases discriminated faults, frequency analysis, and other inputs such as those related to data quality.

Another category of data on which the data usability 136 may be based is on a decision-support mode 144. As noted above, such modes relate to uses to which users and/or clinicians put the data, and may include modes such as therapeutic, adjunctive, or different phases of control of an artificial pancreas system as illustrated in FIG. 15A, and the like.

A further category of data on which the data usability 136 may be based is on other external data 142. This category includes data from sources other than the sensor or the decision-support mode. Such data may include user-entered data, e.g., about how the user is feeling, meals ingested, exercise performed, and the like, as well as data from other external devices, e.g., blood glucose monitors, temperature sensors, and the like. Certain of these external devices may be signally coupled or connected to the monitoring device, and others may be employed by having the user enter data from the external device into the monitoring device.

It will be understood that certain factors may be considered to occupy more than one of these categories. It will be further understood that other categories of data may also be employed. Finally, it is noted that a particular mode transition may be, and often is, based on multiple sources of data from multiple respective categories. Each of these factors and categories of data is described further below with respect to subsequent diagrams.

Data Signal Analysis

Figure 6:
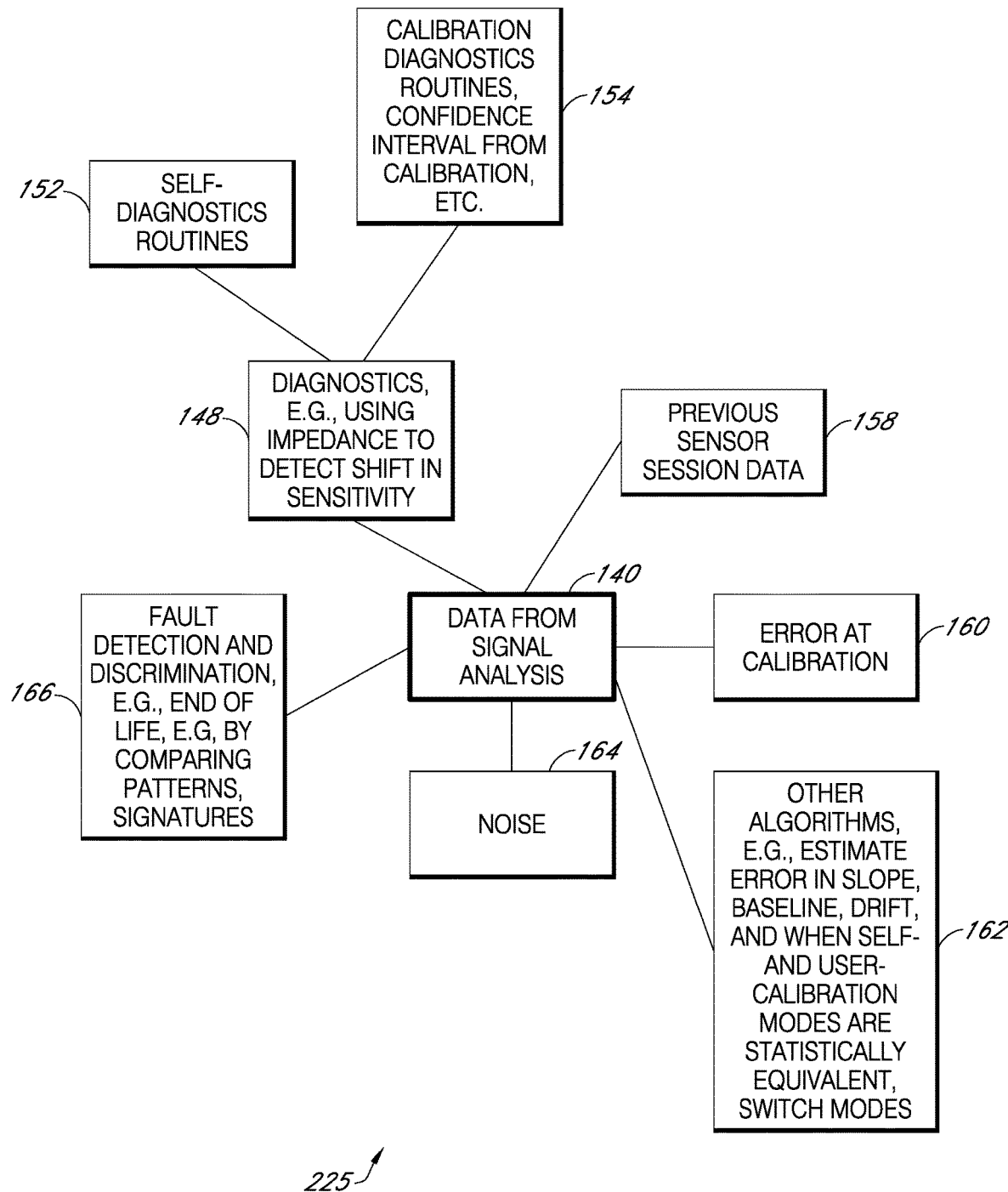
FIG. 6 is a diagram according to present principles showing aspects of data from signal analysis.

FIG. 6 is a diagram 225 illustrating exemplary types of data 140 from signal analysis. In most of these types, sensor signal data is analyzed resulting in data 140 that indicates in some way the usability of the sensor signal data, e.g., its reliability, accuracy, stability, confidence, or other aspects as described or understood. In certain other cases, data 140 does not relate to usability, but may still be employed in the determination of mode switching.

In one specific example, the signal analysis data 140 may include data 164 about noise in the signal. That is, if the signal has a noise level which satisfies a criteria, e.g., is above a predetermined threshold, the usability of the signal or resulting data may be deemed, calculated, or determined to be lower than if the noise level were below the predetermined threshold. Accordingly, in high noise situations, certain modes, such as a therapeutic decision-support mode, may be caused to transition to an adjunctive mode, as the therapeutic reliability of the signal is in question. Alternatively, where the therapeutic level of control is enumerated by phases, the same may be caused to transition to a lower phase. Noise level determination may also be made over the short term or the long term, and in some cases can be determined by analysis of the signal value itself over the long-term or short-term. For example, a long-term drift in a signal baseline value may be indicative of certain types of faults as described in the applications incorporated by reference below.

The signal analysis data 140 may also be based on data 166 about faults detected or discriminated in the signal. Such faults include, e.g., end of life faults, compression faults, dip and recover faults, water spike faults, and the like. In many cases the analysis of such faults includes comparing signal patterns or certain criteria known to be associated with such faults. In this sense the data 140 may be considered to depend to a certain extent on signal values per se. In some cases, where a significant such fault is discriminated, a transition may be caused from, e.g., a device self-calibration mode to a user-dependent calibration mode.

Additional details of systems and methods for noise and fault detection and discrimination are disclosed in U.S. Pat. No. 8,010,174; US Patent Publication No. 2009/0192366-A1, or U.S. Pat. No. 8,290,559; and U.S. Patent Application No. 62/009,065, which are owned by the assignee of the present application and herein incorporated by reference in their entireties.

The signal analysis data 140 may also be based on data 158 about a patient's previous sensor session. For example, in some cases a particular patient may consistently experience a long startup time for their sensor sessions. In these cases, it may be expected that modes relying on external data may be determined to be more reliable during such times. Accordingly, those modes may be switched to from other modes. As a specific example, user-dependent calibration may be relied on more than device self-calibration during these times.

The signal analysis data 140 may also be based on data 160 about errors determined at calibration. Such errors at calibration are related to a systematic bias between a sensor signal value and a reference external meter value. For example, if a significant error at calibration is determined, a mode may be caused to switch from a therapeutic one to an adjunctive one, because of a lessened reliability or usability of the signal. Additional details of systems and methods for determination of such errors at calibration are disclosed in US Patent Publication No. 2014/0182350-A1, which is owned by the assignee of the present application and herein incorporated by reference in its entirety.

The signal analysis data 140 may also be based on data 148 about or from various diagnostic routines, including self-diagnostics routines 152 and calibration-diagnostics routines 154. The former may include periodic diagnostic routines run by the monitoring device and/or sensor electronics to detect errors introduced during routine operation.

The latter relate to routines involved with device self-calibration. The results of calibration diagnostics may include the determination and usage, e.g., in transition criteria, of a confidence interval in displayed readings based on the determined calibration and, in particular, its quality. For example, if calibration-diagnostics routines indicate that the device is not well-calibrated by a device self-calibration routine (e.g., low confidence level), the mode may be caused to switch to user-dependent calibration. In some cases, the monitoring device may periodically enter a self-diagnostics mode to, e.g., cause an interrogation of the sensor, as well as to cause an examination of the resulting transient response. If the response is expected or consistent, mode switching may be contraindicated. If the response is unusual or indicates a problem with the sensor, then mode switching may be indicated, e.g., a switch to a more conservative, safer, or user-protective mode, even if the same results in lessened user convenience.

Additional details of systems and methods for determination of data from diagnostic routines are disclosed in US Patent Publication No. 2012/0265035-A1, which is owned by the assignee of the present application and herein incorporated by reference in its entirety.

The signal analysis data 140 may also be based on data 162 from other algorithms, e.g., which estimate errors in determined slopes and/or baselines corresponding to rate of change data. In some cases, where these are statistically equivalent between modes, such may be an indicator that a mode switch is possible. Additional details of such aspects are described below with respect to FIG. 13 and elsewhere Other types and aspects of signal analysis data are disclosed in U.S. Pat. No. 8,010,174; US Patent Publication No. 2009/0192366-A1; or U.S. Pat. No. 8,290,559; US Patent Publication No. 2012/0265035-A1; U.S. patent application Ser. No. 13/827,119; US Patent Publication No. 2014/0182350-A1; U.S. Patent Application No. 61/978,151; and U.S. patent application Ser. No. 009,065, which are owned by the assignee of the present application and herein incorporated by reference in their entireties.

Data Values Per Se

Figure 7:
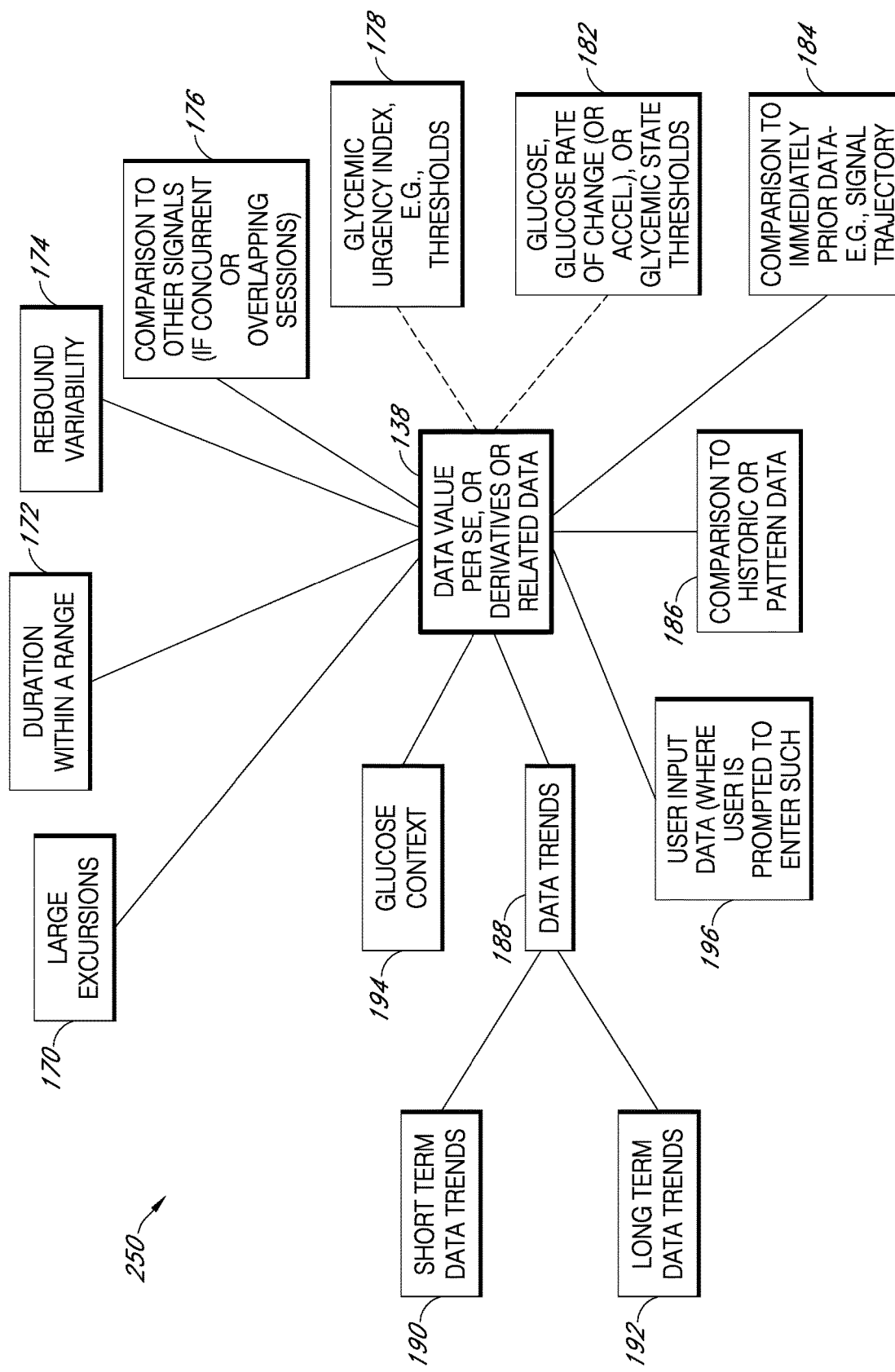
FIG. 7 is a diagram according to present principles showing aspects of data values per se, or data based on such data values.

FIG. 7 is a diagram 250 illustrating exemplary types of analysis 138 pertaining to data values per se.

The analysis of data value 138 may be based on data 182 directly related to the glucose concentration value itself, or related to values uniquely determined by the glucose concentration value, e.g., a glucose rate of change, including slope and/or acceleration, or glycemic state, e.g., hypoglycemia, hyperglycemia, or euglycemia. A particular example of the use of such data is given by analysis of large excursions 170, in which if a large excursions from a desired value or range is encountered, the mode is caused to switch so as to provide additional safety for a user. For example, if a large excursion is seen (e.g., glucose value drop from 150 to 50 within an hour), and the monitoring device is in a device self-calibration mode, the same may be switched to a user-dependent calibration in order to obtain additional and external data, outside of the context of the monitoring device itself. Such data 178 may further be based on a glucose or glycemic zone, e.g., a range of glucose concentration values. For example, a mode may be caused to switch in a hypoglycemic zone but not in a hyperglycemic one.

In a similar way, the data 138 may also be based on data 172 of duration within a range or zone of glucose concentration values, or even within a range or zone of a particular rate of change or acceleration. For example, mode switching, which in a given implementation is partially based on a glycemic range, may be limited to situations in which the glycemic range is maintained for greater than a predetermined threshold period of time. In this way, mode switching is avoided where a glycemic range is simply passed through or only briefly encountered.

The data 138 may also be based on data 178 of a glycemic urgency index, which is a quantity determined by analysis of various parameters or variables, and which relates to not just a glycemic value but more generally to an indication of a patient or user's risk state. For example, a glycemic urgency index may be employed to determine not just if a patient is hyperglycemic, but to further quantify a measure of risk due to a patient's hyperglycemia. As applied to mode switching, if a patient has a high glycemic urgency index, the mode may switch to a more conservative or protective one, to ensure patient safety during the time of the high value.

Additional details of systems and methods for determining in using a glycemic urgency index are disclosed in U.S. Patent Application No. 61/978,151, which is owned by the assignee of the present application and herein incorporated by reference in its entirety.

The data 138 may include data 186 based on comparisons to historical glucose signals and patterns which may be determined or identified therefrom. In these comparisons, current sensor values and patterns may be compared to prior or historic values and patterns, and similarities and deviations determined. As a specific example, if glucose patterns diverge from a normal glucose patterns for a particular host by a particular amount, then adjunctive mode may be triggered.

The data 138 may also be based on data 188 about data trends, which may include short-term data trends 190 and long-term data trends 192. Certain aspects of trend data are discussed above in context with data signal analysis, but here it is noted that overall trends in data may be noted and taken account of in calculations or determinations for mode switching. For example, if an overall trend is seen for a signal reduction in amplitude, e.g., due to the sensor saturation or sensor lack of sensitivity, then such may be noted and in some cases used as the basis for causing mode switching. Of course, in some cases, the sensitivity may be reduced so much that the usability of the signal is no longer appropriate for a particular mode, and thus the mode must be switched to one in which the signal usability is appropriate and within a specified confidence level.

The data 138 may also be based on data 174 based on rebound variability. Rebounding is a phenomenon that occurs when a high blood glucose level occurs directly after and in response to a low blood glucose level. Rebounding may occur when a user ingests a significant amount of carbohydrates to address a hypoglycemia situation. As rebounding is a known phenomenon, its occurrence, when consistent, may not necessarily result in a mode switch or transition. However, when rebounding occurs variably and not consistently, then the usability of the data may be placed into question. In such cases, mode switching may be an appropriate response. For example, a therapeutic mode may transition from one phase to another of control or to an adjunctive mode, a device self-calibration mode may transition to a user-dependent calibration mode, and the like.

The data 138 may also be based on data 194 about glucose context, e.g., whether the data concerns nighttime hypoglycemia. Additional details of systems and methods for determination of glucose context are disclosed in U.S. Patent Application No. 61/978,151, incorporated by reference above, and applications incorporated by reference therein.

The data 138 may also be based on data 196 entered by a user, e.g., where a user is prompted to enter such or where the user enters such on their own. For example, a user may be prompted to enter whether they believe data to be unusually high or low, whether an inaccuracy is perceived, potential causes, or the like. Such user-entered data is further described below with respect to FIGS. 8, 10, 11, 12, and 15.

The data 138 may also be based on data 176 received from other sensors, particularly where there are concurrent or overlapping sessions, i.e., with two sensors simultaneously installed in a patient. In such systems, the data may be compared or shared. A related type of data is comparison data or difference data, which is a difference value or other comparison indicator between the data 176 and that from a subject or main sensor signal.

The data 138 may also be based on data 184 which represents a historical data value from a previously-installed sensor. For example, a last set of data values from and immediately—prior sensor may be compared with the first set of data values from a newly—installed sensor to determine if, e.g., the sensor signal trajectory is consistent. If not, and if the historical data values had a high confidence level, then the usability of the signal from the new sensor may be lowered.

Other Data Including External Data

Figure 8:
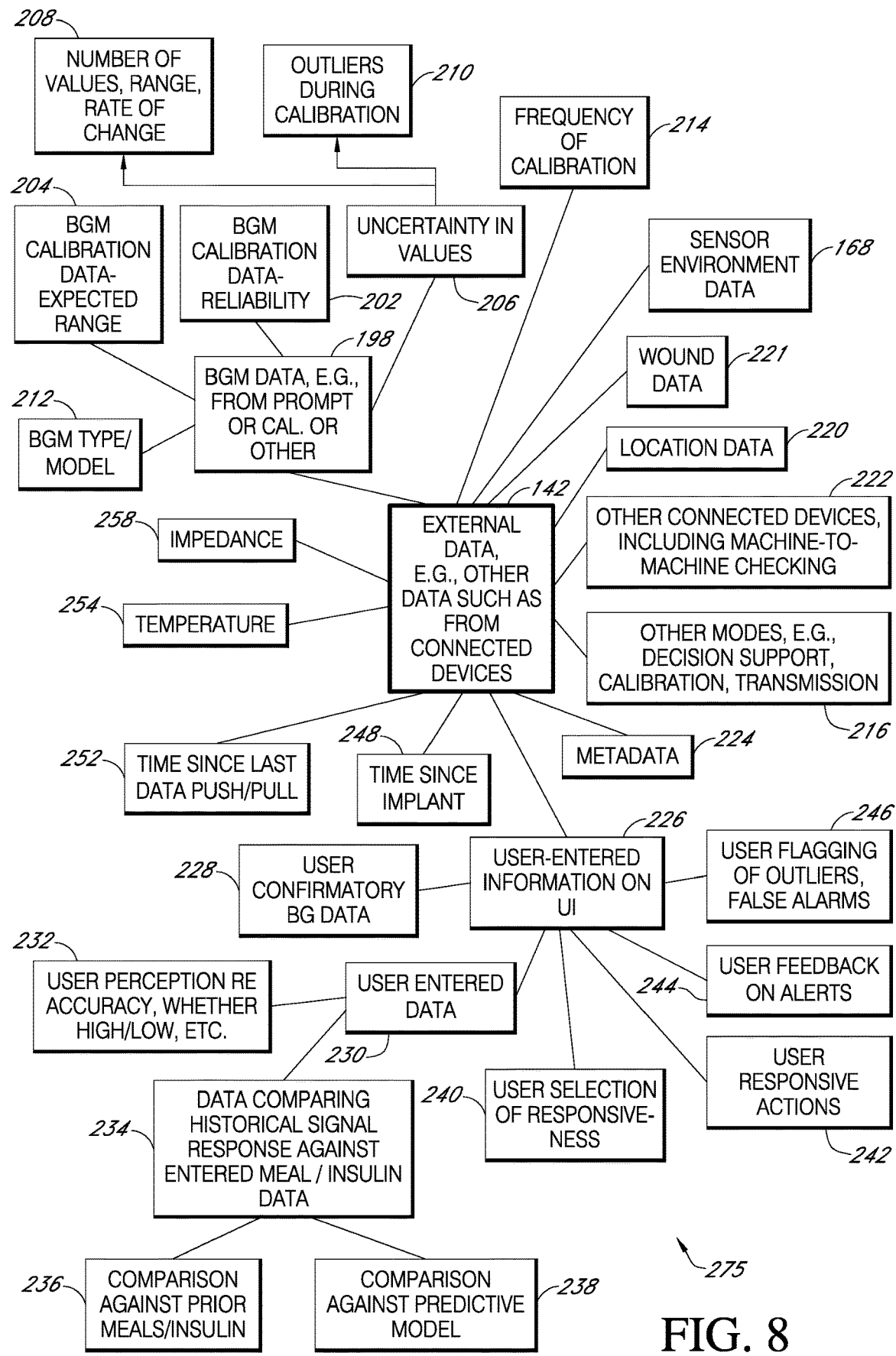
FIG. 8 is a diagram according to present principles showing aspects of other data which may be employed in the determination of data usability, including data from other, e.g., external, devices.

FIG. 8 is a diagram 275 illustrating exemplary types of external data 142 corresponding to non-sensor signal data, including data such as from connected (or not connected) devices.

As a first example, the external data 142 may be metadata 224. For example, metadata may include information about a particular lot from which a group of sensors is drawn. Such information is employed on occasion for purposes of identifying products for various reasons. Metadata analysis may be employed in the determination of transition criteria using such data because metadata may be used to identify like sensors which behave and operate identically or similarly to other sensors. For example, if given certain conditions a given sensor transitions from one mode to another, it may be expected that under similar conditions a sensor from the same lot (as identified by metadata) may act similarly. In other words, historical data based on prior sensors may be extrapolated for use in later sensors, either for an individual, for a group, or for a manufactured lot. Where data is compared across a group of users or a lot, cloud or other network technology may be employed to transmit such metadata or other information.

The external data 142 may also include sensor environment data 168. It is noted that sensor environment data may also be to some extent identified and quantified by data 140 from signal analysis or data 138 pertaining to data values per se. The sensor environment data 168 may include such information as temperature or altitude, as sensors may act differently in different environments. For example, a mode which may be switched to on the basis of comparing a determined data value to a criterion may not cause a transition in another situation, e.g., because the change in value of the data may be determined to be based on altitude rather than a change in a user physiological parameter. The reception of such external data may be via a user input on a user interface of the monitoring device, by automatic detection via a connected device, or by other means. For example, a temperature sensor may be disposed along with the analyte sensor to determine temperature (data 254) and to transmit the same to the monitoring device. As another example, in the determination and use of altitude in a calculation, an altimeter or GPS device may be employed, the latter being available in many mobile devices. Data transmission may occur via wired or wireless, e.g., Bluetooth®, NFC, or other like techniques.

More generally, the external data 142 may be based on data 222 from other connected devices. Other connected devices may include, e.g., activity monitors, sleep monitors, insulin or other medicament delivery pumps, insulin pens, e.g., smart pens, or the like. Other connected devices may also include devices not specific to medical purposes, e.g., GPS devices or mobile devices running GPS location applications, and so on. Other connected devices may further include data from other types of sensors disposed locally with a main analyte sensor. For example, impedance readings may be determined from the sensor data or along with the sensor data, and such may bear on the usability of a signal as such may be employed in the determination of sensor sensitivity. Auxiliary or redundant sensors may also be so used.

For example, an activity monitor or a sleep monitor may be employed to determine a status of a user. In a specific implementation and situation, a CGM device may detect hypoglycemia in a user. If CGM device is operating in an on-demand data transmission mode, and if data from an activity monitor or sleep monitor indicates that the patient is sleeping, then the mode may switch to a "pushed" mode of data transmission to pro-actively alert the user of a potential "overnight low", which is generally a very dangerous condition.

The external data 142 may be as noted based on data 220 about location from, e.g., GPS or other location data sources. For example, a user may desire that a CGM is in a first mode at home and a second mode at work or school. In a specific implementation, a user may desire that data transmission may be on-demand at work or school and in a periodic or device-initiated transmission mode at home. Other variations will also be understood.

The external data 142 may further be based on data from other (e.g., glucose) sensors, which can serve as a check on the reliability of a subject monitoring device. For example, if other devices show a glucose concentration value that greatly differs from the subject monitoring device, such may call into question the main sensor or the usability of the data from the subject monitoring device. Conversely, if other devices show an analyte concentration value consistent with the subject monitoring device, such may increase the confidence level of the glucose concentration value from the subject monitoring device.

The external data 142 may also be based on data 214 about a frequency of calibration. Such frequency of calibration data may be determined by the monitoring device, based on the number of entries provided by the user as calibration measurements. In an example, the entering of more calibration entries than usual may indicate that the user fails to trust the CGM device, for one reason or another. This increase in frequency of calibration may be particularly evident of a low signal usability when the difference between the CGM value and the blood glucose concentration value differ significantly, e.g., more than about 20 mg/dL or 20%. On the other hand, in some cases, an increase in frequency is associated with greater usability as additional data values are received.

The external data 142 may also include data 221 about the tissue in which the sensor is located, and other tissue/sensor interface data. Such data may include characterization of tissue type, wound response, diffusion distance, temperature as determined independently or by temperature data 254, oxygen depletion rate, as well as related sensor data such as thickness of membrane over electrode array, a type of membrane, diffusion of specific species between the electrodes, and the like. In some cases certain of these parameters may be determined by impedance data 258, which may be determined by data signal analysis as well. The above data may be entered by the user or identified by metadata analysis, or obtained via other means.

The external data 142 may also be based on data 248 of the time since implant. In particular, data about the time since implantation of the sensor may bear strongly on the determination and discrimination of certain faults such as those associated with "dip and recover" or end-of-life phenomena. By analyzing the time since implant, systems and methods according to present principles may discriminate such faults, or determine such faults to have not occurred, with greater confidence. In use, within a system and method according to present principles, data based on analysis 248 may, e.g., determine that a "dip and recover" fault is likely, and as a consequence cause a transition from a therapeutic mode to an adjunctive mode. Confidence in the discrimination of such a fault may be even further enhanced by data signal analysis and/or data value analysis.

Additional details of systems and methods for determining and discriminating faults and failure modes are disclosed in U.S. Patent Application No. 62/009,065, which is owned by the assignee of the present application and herein incorporated by reference in its entirety.

The external data 142 may also be based on data 226 of user-supplied information, e.g., user responses to queries or prompts on the user interface of the monitoring device. For example, a user may be questioned as to whether an adhesive on the sensor electronics/transmitter appears to be peeling. If the user responds in the affirmative, the result may be less confidence in the sensor reading and thus reduced sensor signal usability. The data 226 can also relate to user selection of responsiveness 240, e.g., whether a user prefers smooth data with a time lag or noisy data that is more responsive to actual glucose changes. Such a selection may be entered on a user interface that, e.g., appears as a slider switch on the user interface where the user slides their "responsiveness" preference.

The data 226 may further include data 246 where a user flags outlier data, e.g., where the patient flags data that is unusually high or low, or that represents false alarms, e.g., where the patient identifies where the CGM is showing highs or lows incorrectly, as well as user feedback 244 about alerts or alarms. Data 242 about responsive actions may also be included in data 226. For example, if the user takes no actions or responses to alerts or alarms, then it may be inferred that the user is not a reliable source of data. These aspects are described in greater detail below in the context of specific mode transitions.

The data 226 of user-entered or user-supplied information may further include information in the form of user-entered data 230. The data 230 can include data 232 about user perceptions, e.g., whether CGM data appears accurate, or whether it appears high or low. Such data can also include user perceptions about glycemic ranges, e.g., whether the user feels like they have low or high blood sugar. The data 230 can also include data based on user input, but which itself is different from the actual data input by the user. For example, a user-perceived error in the monitoring device may be deduced by the user providing external meter values with or without prompts, or if the user provides external meter values at a greater frequency or number than usual for that patient, or at a greater frequency or number than requested by the monitoring device itself.

The data 230 can also include information about meals ingested, insulin taken, exercise performed, or the like, and in this case when data 230 is entered, an optional step may be to determine data 234 which represents whether the entered data, e.g., a meal response or a distribution of the same, is consistent with prior signal values seen when similar meals were ingested or exercise performed. In particular, the comparison may be against prior entered meal/insulin/exercise information 236 known, or the same may be compared with predictive models 238. If meal or insulin responses change for a patient for the same entered meal or carbohydrate count, as compared to previously declared meal or carbohydrate counts of the same amount, then an error may be suspected and the usability of the data for therapeutic decision making may be in question (e.g., resulting in lower confidence level). The comparison may be with respect to the signal response to carbohydrates, a rate of change, a duration of the meal response, or the like. Prompts or queries may also be employed where the same are not necessarily compared against prior meals, insulin, or exercise, but where the prompts attempt to confirm notable readings. For example, if the glucose concentration value sharply rises, the query could prompt the user to enter if they just ate a large meal. The responses to such queries or prompts can determine if the signal is acting in an expected or consistent way, or if the signal is acting in erroneous fashion affecting the usability of the data and potentially causing a mode switch.

Another type of external or other data 142 includes a time duration 252 since the last data push or pull. In other words, if a significant time period has elapsed since the last time data was received by the monitoring device, such may be employed as a criterion in a mode transition. As a specific example, if a long period of time has elapsed since the device last received data, a pushed or automatic data transmission mode may be entered, so as to alert the user to their current glycemic state.

Another type of external or other data 142 includes data from an external meter 198, e.g., an external blood glucose meter. Such data may be received on the basis of a prompt, for confirmation or calibration purposes, or based on other initiators. Such data 198 is not limited to only meter reading values, but may also be based on data 212 about an external meter type or model. The data 198 may further include calibration data 204 about an expected range of signal values (given the current measurement) or calibration data 202 related to reliability, e.g., noise values or other signal characteristics values. The external meter data 198 may further include data 206 about an uncertainty in measured values, including data 208 about a number of data points, their range, their rate of change, or the like, as well as data 210 about outlier values.

Another type of external or other data 142 which may be employed, particularly to modify triggers or alter criteria, e.g., thresholds for transitions, is data 216 about other parallel or concurrent modes in which the monitoring device is operating, which may include calibration modes, decision-support modes, transmission modes, or any other such operating mode. In this implementation it is data about a different parallel mode that is being employed as an input in the determination of whether to switch a subject mode. The other different parallel mode has already been presumably determined, e.g., whether by user or device selection or by another of the mode switching examples.

Figure 9:
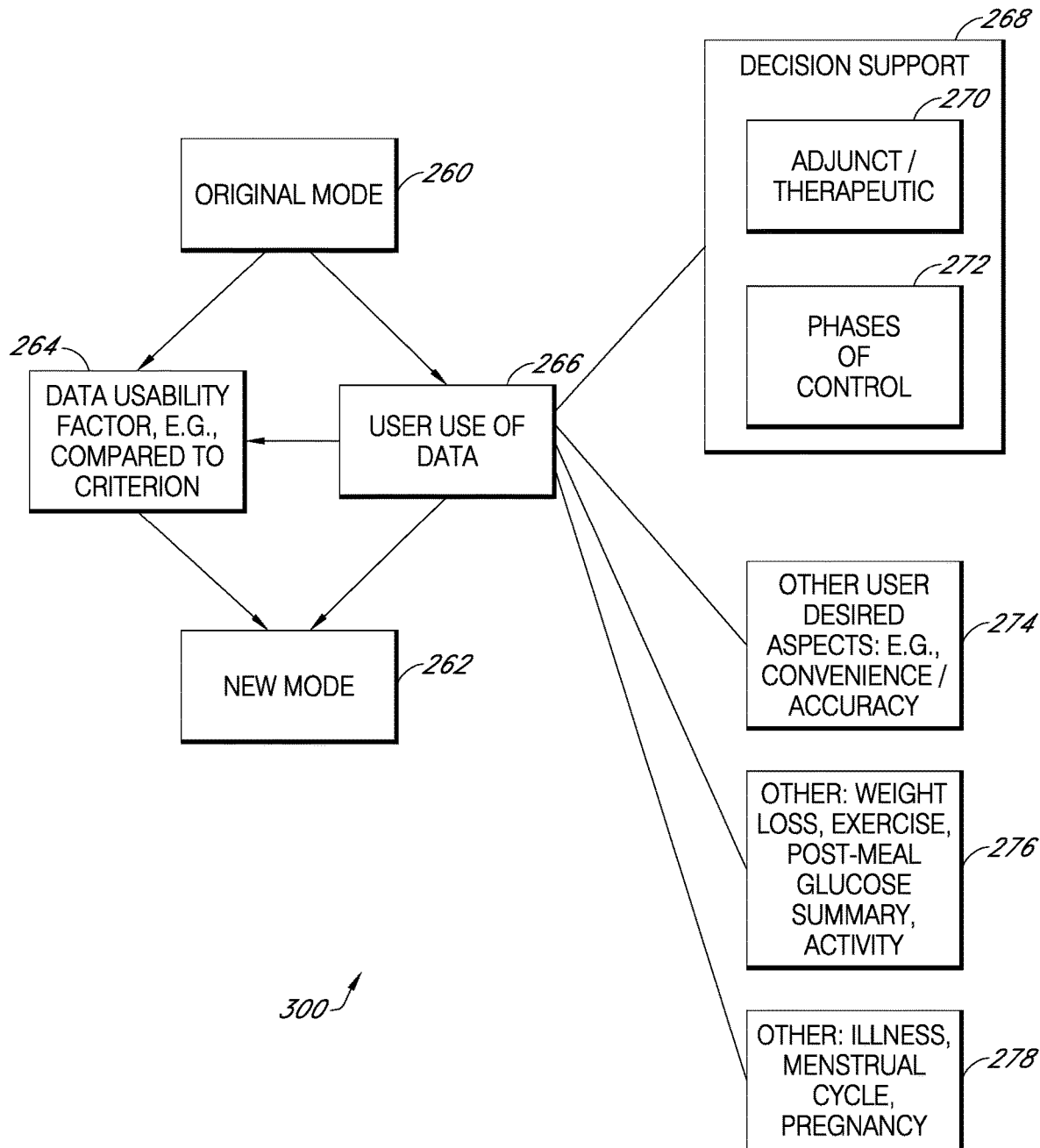
FIG. 9 is a flowchart according to present principles showing another implementation of a method of mode switching, in particular depicting decision-support aspects such as an intended use of CGM data.

One such parallel mode is the decision-support mode 144 (see FIG. 5). In particular, any of the "usability" criteria described in FIGS. 6-8 could be modified by the system in real time based on a decision support mode of the device. Put another way, the criteria determinative for mode switching, above, may depend on how the user would like to use the data from the device. FIG. 9 is a flowchart 300 illustrating how data about other operating modes may be employed as criteria for mode switching of a subject mode.

In more detail, CGM may have many different uses or indications. Some users may prefer CGM for general educational and behavioral modification, e.g., Type II diabetics on oral medications, while others may use CGM to dose insulin throughout the day (e.g., Type I or insulin-dependent Type II patients), or even as a data feed into a closed-loop artificial pancreas system. The criteria for usability/reliability of data for insulin dosing should be more stringent than the criteria for usability/reliability for education purposes. While multiple different CGM sensor designs could be deployed for each specific indication or use, it would be simpler to provide one solution for CGM and allow that system to adapt to that solution. Accordingly, in some implementations the monitoring device may request or require the user to provide information regarding that patient and/or how the patient intends to use the data.

Accordingly, in the first step of flowchart 300, the monitoring device is operating in an original or initial mode 260. The decision or determination by the monitoring device to switch to a new mode 262 may still be based on a factor related to data usability 264 (as determined by a criterion), but the same may also be based on other data 266, e.g., about the intended use of the monitoring device (such data is indicated in FIG. 8 as data 230). Such data 266 may include data 268 about a decision-support type, e.g., data 270 about whether the use is adjunctive or therapeutic, data 272 about a phase in which the device or devices are operating, the phase representing a level of control, or the like. It will be understood that data 270 and data 272 may overlap, and that combinations of such data may be employed.

Data 276 about other uses of the device which could affect decision-support may also be indicated by the user and included as data 266. These may include data 276 about user intentions, or desired use information relating to weight loss, exercise impact, post-meal glucose summary, a desire to select more nutritious foods versus junk food, or the like. The data 266 may also be drawn from patient current health data 278 including data about whether the user is ill, whether the user is experiencing pregnancy or their menstrual cycle, level of activity, type of activity, and the like. The data 266 may further be drawn from specific patient goals such as hypoglycemic avoidance, nighttime control, postprandial control, longer duration of the sensor session, and the like.

The data 266 may further include data 274 about user preference for convenience versus accuracy. In other words, the user can indicate a preference for accuracy over convenience, and the criteria can adjust for that. For example, the system can call for additional blood glucose external meter calibration values, and such would increase accuracy at the expense of user convenience. Alternatively, the user can indicate that they prefer convenience over accuracy, and the criteria can adjust for that. In this case, the system may perform more device self-calibration and less user-dependent calibration. The system can in some cases tighten other controls to attempt to make up for the loss in accuracy. For example, thresholds for hypoglycemic and hyperglycemic ranges may be loosened, so that while accuracy is lessened, a user may be alerted earlier to the entry into such glycemic states. User preference may also be employed to determine which mode to start on. Specific user goals may be employed in this mode determination, e.g., a new user may have more simple or less complex goals, and such can be reflected in the determined mode. Whatever the user goal, the user interface may be provided with an indicator to clearly indicate the transition, as well as (in many cases) an indicator of the new mode of operation and accompanying new mode of user interaction in which the device is operating. The indicator may in some cases expressly indicate the transition, e.g., textually or verbally, or may indicate the same in other ways, e.g., by the user of color, shapes, pictures, or the like. In some cases the indication is not to a person but to a system, e.g., a pump, and in this case the transition will also be clearly indicated by, e.g., a flag or other data indicator. The pump or other downstream device may then treat received data according to the new mode, which may in some cases be different from how data was treated under the old mode, although such is not necessarily required.

Figure 10:
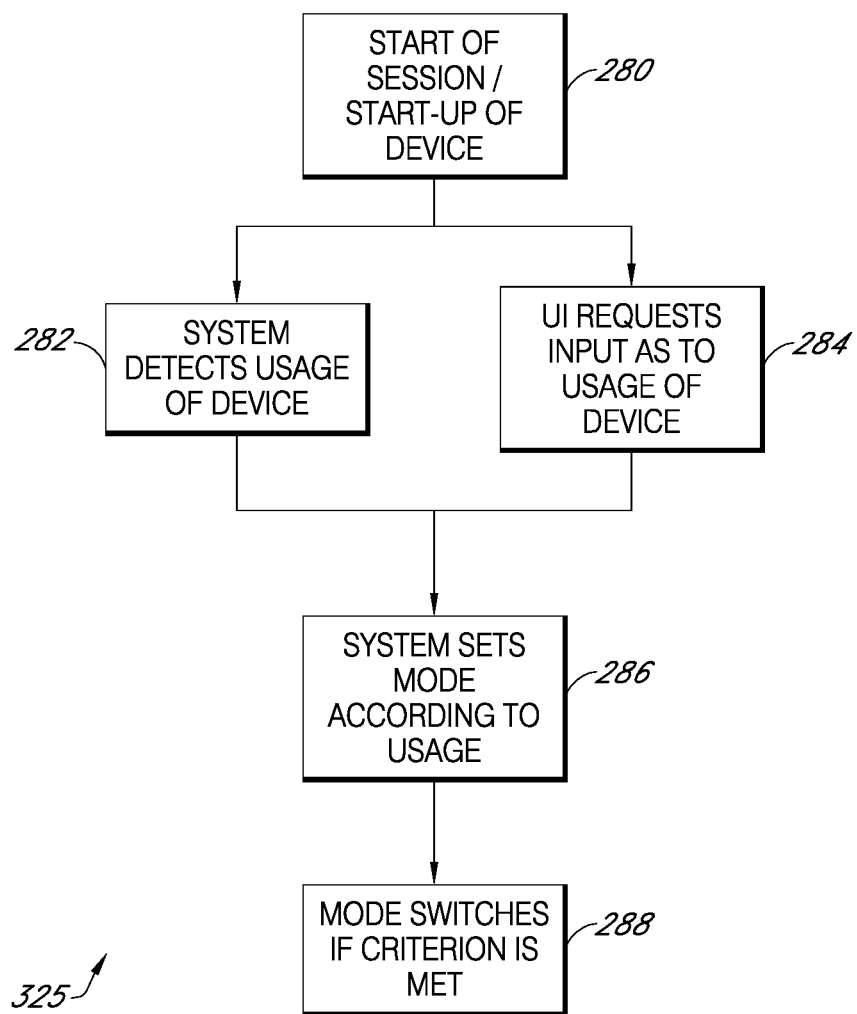
FIG. 10 is a flowchart according to present principles showing another implementation of a method of mode switching, in particular depicting system detection of external devices.

In another implementation, as shown in the flowchart 325 of FIG. 10, the system may be employed to detect usage of the device. In a first step, a session begins and/or the monitoring device starts up (step 280). In some cases the monitoring device starts up in a fully configured mode as enumerated above, e.g., by simply starting up in a last-identified mode. In other implementations the monitoring device powers up and as part of its initial configuration determines what mode to start in. As part of this determination, the monitoring device may detect the usage of the device (step 282). For example, the monitoring device may detect that it is signally coupled to a medicament delivery device such as an insulin pump. In this case, the monitoring device may start up in a therapeutic mode, subject to, e.g., optional patient confirmation. The user interface of the monitoring device may also request input as to the usage of the device (step 284). The system detected usage and the user-entered information may be employed in a final determination of what mode the monitoring device is set to (step 286). In other words, the system-detected usage and the user-entered usage data may not by themselves uniquely determine the most appropriate mode, but the two may act as data inputs and which together (and optionally with other data) determine the device mode. Moreover, in some cases it may not be desired to have a user enter a particular mode per se, but rather to have the user enter more user-friendly information that is in turn converted to a determined mode. For example, it may be more understandable to a user to indicate that their CGM is driving their pump then to necessarily have the user indicate the more technical distinction that the device is in a therapeutic mode rather than an adjunctive one.

In any case, once the mode is set (step 286), the mode may be switched according to methods above if determined data meets transition criteria (step 288). Specific examples of mode switching are described below.

User-Dependent Calibration Versus Device Self-Calibration

One exemplary type of mode switching is between user-dependent calibration and device self-calibration, e.g., switching between using no blood glucose meter readings (e.g., using a priori, internal (e.g., using impedance), prior derived values, or device self-calibration only) and using blood glucose meter calibration, or vice versa. User-dependent calibration generally requires ongoing input of external reference data, e.g., glucose concentration meter values, to maintain calibration, although a priori information may be included as a part of the algorithm.

Additional details of systems and methods for user-dependent calibration are disclosed in U.S. Pat. Nos. 7,778, 680; and 7,920,906, which are owned by the assignee of the present application and herein incorporated by reference in their entireties.

Device self-calibration mode does not require ongoing input of external reference data from the patient, although previously entered external reference data may be used to influence the calibration. While it is desirable to ensure the reliability or stability of device self-calibration, one problem that has been encountered is that the usability of device self-calibration may be influenced by a number of variables, including: stability of the calibration factors over time in vivo; in vitro to in vivo predictability of calibration factors (which may be influenced by shelf-life); and patient-to-patient variability of the calibration factors, as examples.

Additional details of systems and methods for device self-calibration are disclosed in U.S. patent application Ser. No. 13/827,119, which is owned by the assignee of the present application and herein incorporated by reference in its entirety.

Similarly, the usability of user-dependent calibration has challenges as well, as the same may be influenced by a number of variables, including the frequency and reliability of the user's blood glucose calibration entries. Accordingly, one mode or another may be preferred at a given time. In certain systems and methods according to present principles, the mode switching between these two modes occurs to preferentially select the mode with the most preferred data usability, with the mode switching occurring adaptively and dynamically, in real time, based on the evaluation of transition criteria.

Figure 11:
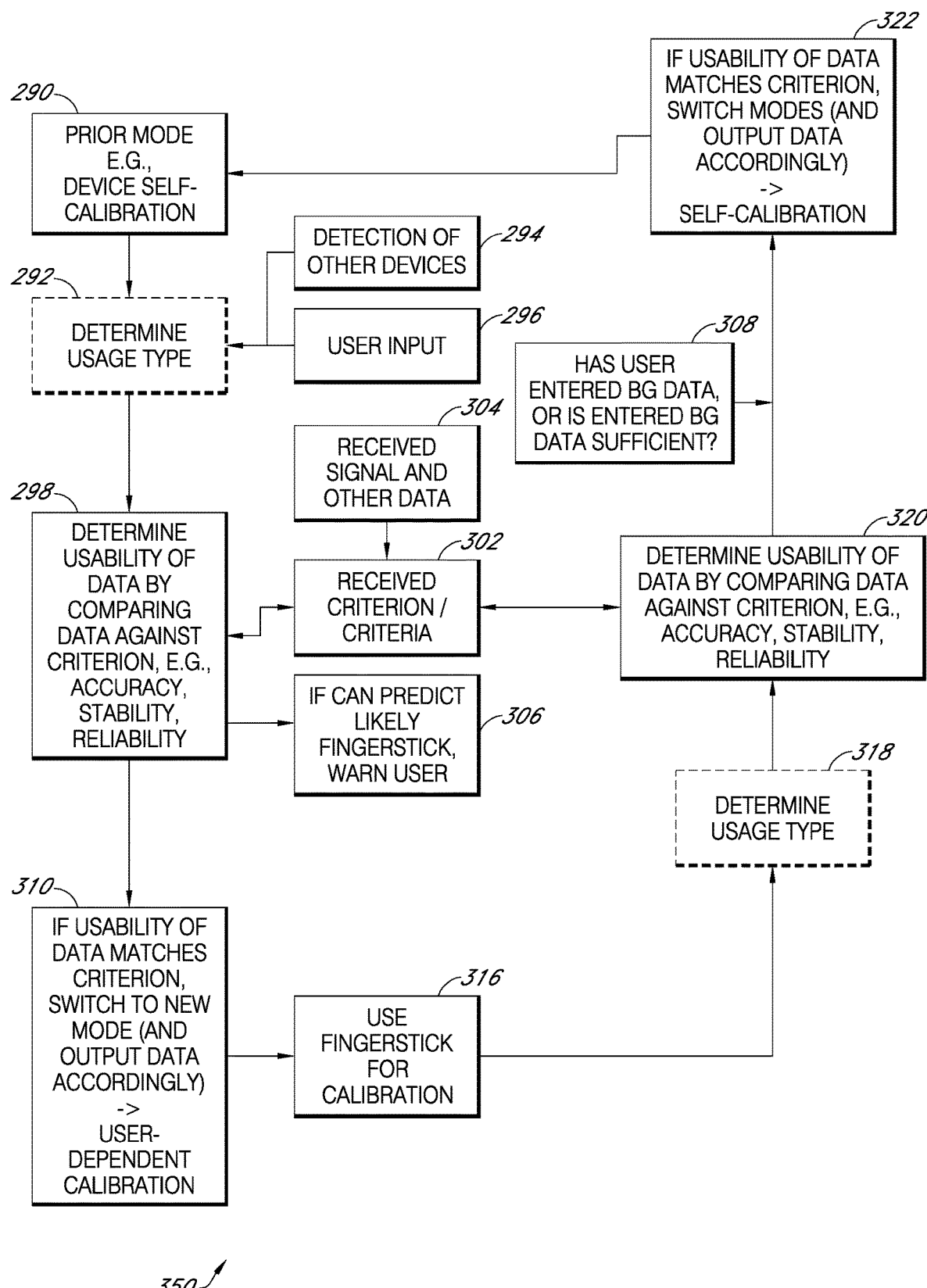
FIG. 11 is a flowchart according to present principles showing another implementation of a method of mode switching, in particular depicting transitions between calibration modes.

FIG. 11 shows a flowchart 350 for accomplishing calibration mode switching. Several transition criteria that are particularly useful in calibration mode switching are described in the figure, but it will be understood that any of the transition criteria described in FIGS. 5-9 may also be employed. Moreover, while FIG. 11 details transitions between calibration modes, it will be understood that other types of modes may be running in parallel or concurrently, e.g., decision support modes, data transmission modes, and the like.

In a first step, a monitoring device is presumed to be in a prior, original, first, or initial mode (step 290). For purposes of discussion this mode is shown as a self-calibration mode. In this mode, sensor data is transformed using calibration factors determined by the device itself, without recourse to external values.

An optional next step is to determine a usage type (step 292). The usage type may pertain to a decision-support mode, a user intention, a user goal, or other aspects as described above. Such data may also pertain to other patient characteristics which require increased safety requirements versus convenience, and may thus change the evaluated transition criteria. Such patient characteristics may include data about gastroparesis, hypoglycemia awareness, etc.

The usage type determined may be assisted by the detection 294 of other coupled devices, as well as by user input 296. In this regard it is noted that the safety requirements for a therapeutic mode (e.g., of whatever phase) are generally higher than the safety requirements for an adjunctive mode, while the convenience requirements may be higher for an adjunctive mode as compared to a therapeutic mode. Accordingly, the criteria for switching modes may be weighted more for safety if in a therapeutic mode and may be weighted more for convenience in the adjunctive mode. Accordingly, the optional step 292 of requesting usage type information is included in the flowchart 350, either as the same is automatically detected (step 294), e.g., when the sensor is connected to an insulin pump, or prompted as input by the user (step 296). For example, one or a series of questions could be asked of the user at the start of a session or when setting up the device that determines how the user intends to use the sensor data. For example, a user could select a use case for the data, e.g., therapeutic versus adjunctive, or, e.g., educational e.g., just watching trends, versus decision-support based. Such data may even be used to determine or modify aspects within a mode. For example, within a user-dependent calibration mode, a monitoring device algorithm may adjust to more or less external blood glucose meter prompts, as some users would rather calibrate more often and achieve greater accuracy, e.g., traditionally-treated type I diabetes patients, while other patients would rather not calibrate and do not require a high-resolution of accuracy, e.g., type II diabetics on oral medications. This determination of accuracy can further be used in the startup mode to drive which mode the monitoring device is initially configured to, e.g., user-dependent calibration versus device self-calibration.

As another example of where the usage type is determined in part by detection of other devices (step 294), the monitoring device may detect that it is connected to a medicament delivery pump and may further detect a setting that indicates its use in a closed-loop-decision support configuration for the pump. The monitoring device may then adjust criteria for calibration modes based thereon, e.g., increasing the calibration requirements based thereon.

In any case, a next step is to determine the usability of the current calibration mode by comparison to one or more criteria (step 298). In particular, a data signal, e.g., from the sensor, or other determined data, is received (step 304), and one or more criteria are received or retrieved (step 302). For example, the criteria may be received from memory or other local or online storage.

The criteria used may be one or more from the group described with respect to FIGS. 5-9, but certain exemplary criteria will be described and/or reiterated here.

One criterion which may be employed includes data that is internally detected by the monitoring device and which indicates sensitivity. For example, as shown in FIG. 6, self-diagnostics which measure impedance can be employed to detect shifts in sensitivity. Such self-diagnostics may be performed on a regular basis or whenever errors are perceived. Where a shift in sensitivity is detected, the same may be employed to inform the device self-calibration or the same may be employed to cause a transition to a new mode, e.g., user-dependent calibration, if the shift in sensitivity is greater than a predetermined criterion.

Another criterion which may be employed is based on data from other connected devices (see FIG. 8). This "machine-to-machine" checking can be employed to, e.g., check CGM values against a connected blood glucose meter. The connection between such devices may be peer-to-peer or over a network. In this example, if a blood glucose meter does not match the CGM value, a query may be initiated to either perform diagnostics without user input or to prompt the user to perform a step to assist in the reconciliation of such values.

Referring in addition to FIG. 7, the evaluation of determined data against a criteria may include evaluation of current data against historic values of, e.g., glucose ranges, mean values, patient specific profiles, patterns, or the like. If the determined data does not follow a patient's individual normal glucose profile within certain criteria, e.g., within 25%, 10%, or the like, a patient may be prompted to input whether the patient believes the data to be unusually high or low, or whether the patient perceives an inaccuracy. The patient may further be prompted as to potential reasons for abnormal glucose readings. The comparison may be made more granular by comparing based on time of day, day of week, the context of the glucose, e.g., whether the same pertains to nighttime hypoglycemia, a post-meal high, and so on. The comparison may further employ statistical factors such as variance, mean, rate of change, the variability of glucose concentration values, or the like.

Other criteria which may be employed include any of those described above in connection with FIGS. 5-9, including without limitation, e.g., user responsive actions to alerts and alarms (e.g., amount of time between alert and user acknowledgement), user feedback on alerts (e.g., levels of perceived accuracy), the entry by the user of outlier data and false alarms (e.g., as determined by outlier detection and/or measures of alarm fatigue), the glucose values resulting from confirmatory external meter readings, which may be prompted for by the monitoring device or otherwise provided by the user, meal and insulin data entered and glucose value responses, as well as comparisons to prior meal and insulin data, whether sensor trajectory matches that of previously installed sensors (e.g., profiles associated with break-in, changes in sensitivity, etc.), other concurrent operating modes, and so on. Other criteria may include, if multiple sensors are present, whether one or a "main" sensor reading is consistent with others of the multiple sensors, including situations in which the main sensor tracks the same hormone or biological analyte as the other sensors as well as situations in which the main sensor tracks other hormones or other biological analytes, particularly where such hormones and other biological analytes are known to bear a relationship with the hormone or other biological analyte tracked by the one or main sensor.

In any case, if the usability of the data matches the one or more transition criteria, a transition may occur to the new mode, e.g., a user-dependent calibration mode (step 310). In this mode, data is calibrated based on an external meter, e.g., using finger sticks for calibration (step 316).

In some cases, where a transition to a user-dependent calibration mode is not immediately performed, but where it can be determined that such a transition will likely be necessary, the monitoring device may render a display indicating that an external meter reading is likely to be necessary. In this way, a user can be prepared to carry the necessary meter on their person.

In some implementations, a transition to a new mode may be postponed by the performance of one or more steps. For example, in the above example where a transition to a user-dependent mode is contemplated, an external meter reading may be requested of the user to provide confirmation of the device self-calibration (see, e.g., user confirmatory blood glucose data 228 in FIG. 8). Depending on the results of the external meter reading, the device self-calibration may be confirmed, the device self-calibration may be modified or adjusted, or the monitoring device may determine that a mode switch is necessary.

Data may then be output accordingly, pursuant to the new mode. For example, the monitoring device may show different types of displays based on the mode or based on a setting within the mode. In a particular implementation, for data with high usability, numerical values of blood glucose measurements may be displayed. For data with lower usability, ranges of data values may be displayed, or the data may appear in a selected color based on the range. Additional details of systems and methods for displaying data in different formats are disclosed in U.S. Provisional Patent Application Ser. No. 61/978,151, which is owned by the assignee of the present application and herein incorporated by reference in its entirety. Further details are described below with respect to FIGS. 18A-18D, which are in the context of displays for different decision-support modes, but which can be extended to different calibration modes, data transmission modes, as well as other modes.

Similar consideration pertain to the reverse transition, e.g., from user-dependent calibration to device self-calibration. A usage type may be determined (step 318) as in step 292, particularly if the usage type has changed since the occurrence of step 292. Usability of data is determined by comparing determined data against one or more criteria (step 320), and if the usability of the data matches one or more criteria, a transition may be caused (step 322), e.g., back to the device self-calibration mode (or to another mode).

In general, if calibration parameters evaluated meet certain criteria indicative of necessary external reference data for calibration, the user-dependent calibration mode may be entered. On the other hand, if calibration parameters meet other criteria indicative of sufficiency of device self-calibration going forward, the device self-calibration mode may be entered. In some cases a user may be prompted before switching to device self-calibration, and the prompt could be informational or require confirmation by the user prior to the mode switching.

Figure 12:
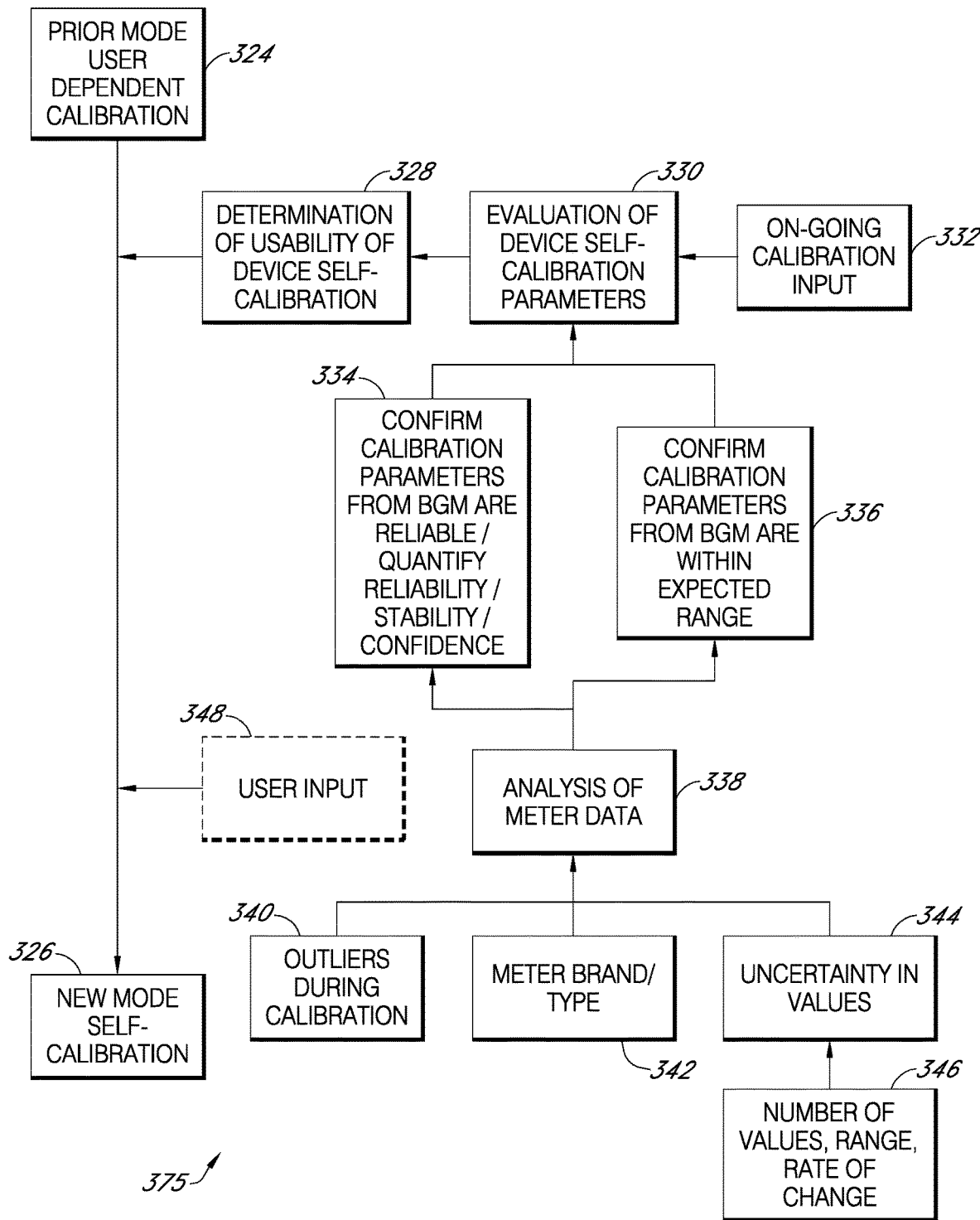
FIG. 12 is a flowchart according to present principles showing another implementation of a method of mode switching, again depicting transitions between calibration modes.

A more detailed flowchart 375 is depicted in FIG. 12 for this aspect. In addition, specific switching criteria from user-dependent calibration to device self-calibration are also shown and described.

In this particular scenario of the reverse transition from an initial user-dependent calibration mode 324 to a new device self-calibration mode 326, one criterion which may be employed is whether or not the user has entered external meter values, or a sufficient number thereof. If the user has not, then the monitoring device may transition to a self-calibration mode until an external meter value, or a sufficient number of the same, are entered, which may then trigger user-dependent calibration.

Other criteria which may be employed include any described above in connection with FIGS. 5-9, as well as other variables and parameters, particularly those related to a determination (step 328) of the usability of the device self-calibration over time, e.g., error at calibration, an individual user profile, and the like. One way to determine the usability of the device self-calibration is by the evaluation (step 330) of device self-calibration parameters, which are subject to ongoing calibration input (step 332). A general goal in certain implementations is to ensure the reliability, accuracy, and/or stability of the device self-calibration for an individual patient, especially the first time a patient uses the device, so that the same may be safely transitioned into from a user-dependent calibration mode. Once sensor usability properties have been determined, e.g., stability, accuracy, reliability, confidence, or the like, the same may be seeded into internal calibration parameters for the remainder of the session and even in some cases for future sessions.

Accordingly, one transition criteria which may be employed includes data about whether calibration parameters from external meter readings are within a particular confidence interval or otherwise reliable or stable (step 334), e.g., no more than a certain percentage change, e.g., 5, 4, 3, 2, or 1% over one day, two days, or the like, and whether the same match those determined by the device self-calibration. A related transition criteria include whether calibration parameters are within an expected range (step 336) based on a priori or predetermined internal measures, e.g., within the same range as a set of previous patient-specific calibration parameters, within expected factory determined ranges, and/or within expected internal testing ranges, e.g., as determined by impedance measurements. Other transition criteria include confidence in the user's external blood glucose meter used for calibration, as well as the user ability to enter a correct reading from the meter. Such can be determined by analyzing meter data (step 338) based on analysis of a number of outliers detected during a calibration routine (step 340), analysis of data about the meter brand and type (step 342), or the like. In this example, the criteria for mode switching may be at least in part dependent upon a number or type of outliers detected (e.g., number of BG reference values that appear in accurate based on outlier detection criteria). Yet additional related meter related data include the uncertainty of the blood glucose meter values (step 344) entered for calibration based on analysis of a number of factors (step 346) including the number of values available, e.g., as more values means a more accurate regression; glucose range, as more data points spread across a full glucose range again allows a more accurate regression and subsequent linearity across the range; and/or rate of change, because time lag between interstitial glucose and capillary glucose are more noticeable when glucose is rising or falling. In these examples, the criteria for mode switching may be at least in part dependent upon a certainty level threshold of such data.

In some cases, the determination of whether glucose values and calibration parameters are within expected ranges may be determined probabilistically, and details about such methods are provided in WO 2014/158327A2, owned by the assignee of the present application and herein incorporated by reference in its entirety.

Yet another related transition criteria may relate to the calibration or confirmation external meter reading value itself, particularly where the value is the same as a default reading. For example, in some implementations, a monitoring device may default to 120 mg/dL for manual entry of blood glucose concentration values. The monitoring device may be configured to question or to give a lower confidence in default values that are regularly accepted, particularly where such are found to be outliers.

Other transition criteria may include decision-support mode, e.g., whether the use is adjunctive or therapeutic, or the like. Yet other transition criteria may be as described above, including those employing user input (step 348).

In a particular example of mode switching between user-dependent calibration and device self-calibration, a user may start with user-dependent calibration for a first sensor in a four pack of sensors, where the four pack of sensors are all from the same manufacturing lot. Once calibration is established for the first sensor using user-dependent calibration, the next three sensors in the pack/kit could switch to device self-calibration based on the calibration of the first sensor in the pack. This ability is predicated on the likelihood that different sensors within the same lot have similar or the same specific characteristics that when used by the same host, will perform in a similar manner (similar correlations could be made for different hosts using the sensors from the same lot). As noted, such lot data may be determined using analysis of metadata.

As noted above, while mode switching may occur to user-dependent calibration or to device self-calibration, generally the latter is preferred if possible due to increased user convenience. FIG. 13 illustrates a logical diagram and accompanying chart which show how present principles may be employed to gain confidence in device self-calibration. In the solution of FIG. 13, both user-dependent calibration (mode 354) and device self-calibration (mode 356) are run in parallel. Upon receipt of inputs or information, when confidence in the device self-calibration satisfies certain criteria, e.g., exceeds a predetermined threshold, then no additional external meter readings may be required for calibration. In this case, the output is entirely based on the device self-calibration. In other implementations, the outputs of both algorithms may be combined and weighted accordingly to arrive at a displayed output.

In such a parallel system, the output of each calibration mode algorithm is evaluated against criteria 360, and the accuracy, reliability, stability, and/or confidence in the different calibration parameters resulting from each of the two modes running in parallel is compared, or alternatively, the usability of the signal from each of the two calibration mode algorithms is compared, particularly over an optional transition region 358.

For example, one or both outputs may be compared to incoming blood glucose concentration values. To ensure accuracy over a range, the compared blood glucose (external meter) values may be provided and compared at extreme high and low values 352.

Other determined signals and transition criteria include any of the transition criteria described above, but certain types will be described below as particularly useful in certain implementations. Such may include internal inputs, such as the effectiveness of self-diagnostics or internal calibration information, e.g., impedance. Yet other signal analysis criteria include comparisons of slope and baseline from user-dependent calibrations versus slope and baseline from device self-calibration algorithms. Such may be particularly employed to examine correlations to a prior session. Such exemplary implementations are particularly useful in that some patients have certain physiological differences, such as a typically high baseline, as compared to patients with, e.g., a low baseline, and such comparisons may thus be useful in cases where baseline estimates are made.

Yet other sorts of signals and transition criteria include those related to fault discrimination, which may be employed to determine a type of artifact or the like. During such times of artifact presence, the user-dependent calibration may not be relied upon, or its influence may be lowered in the weighting. For example, if compression artifacts are discriminated, and a blood glucose meter value is entered into the system at about the same time, and the device self-calibration mode should be relied upon more heavily.

Figure 13A:
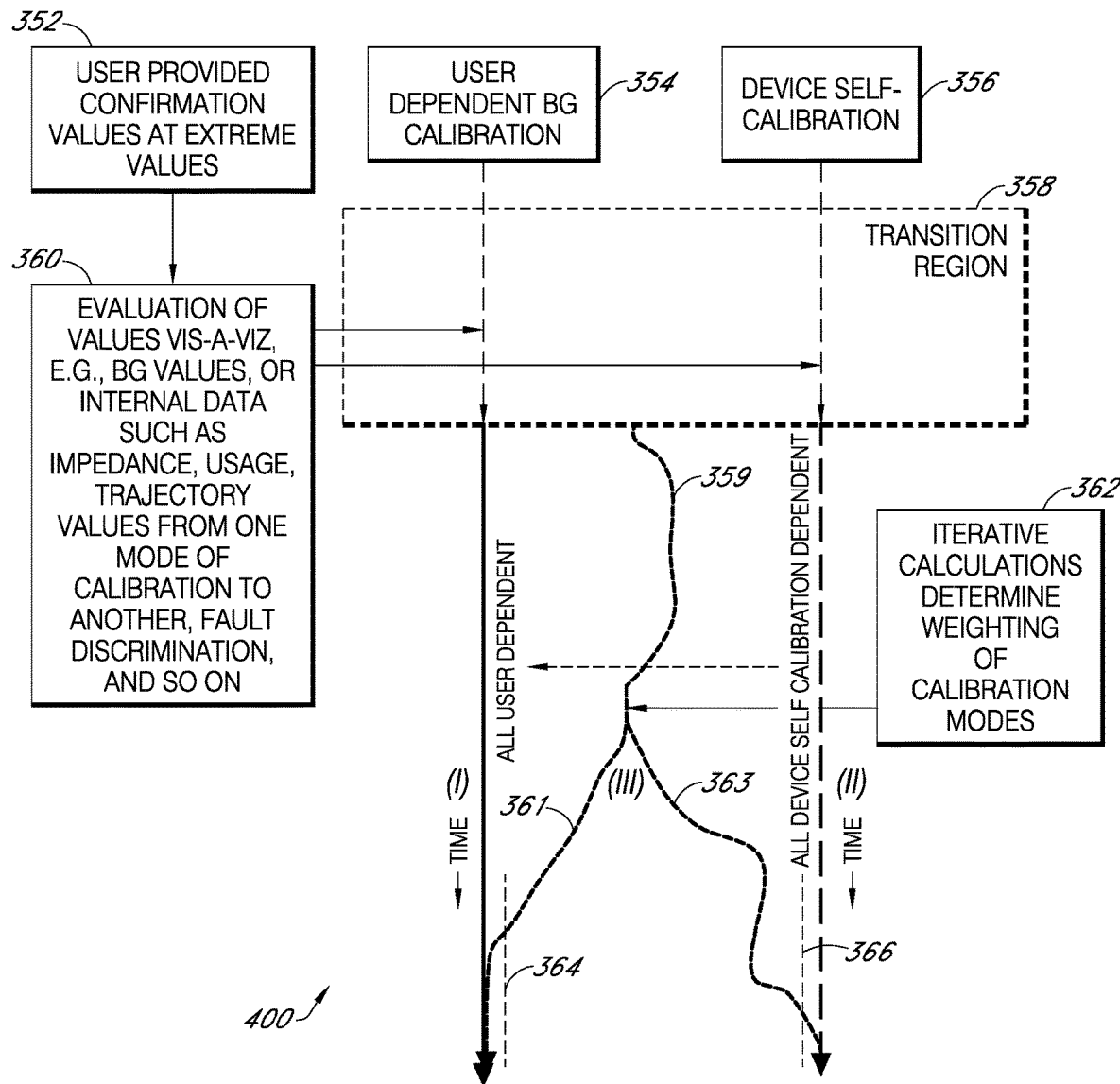
FIG. 13A is a flowchart according to present principles showing another implementation of a method of mode switching, in particular depicting multiple modes operating concurrently.
Figure 13B:
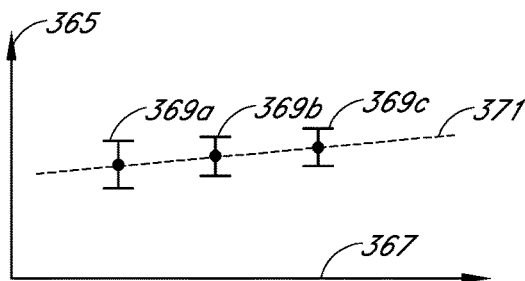
FIG. 13B is a chart illustrating matching of calibration parameters to allow switching.

Yet another sort of signal and transition criteria relates to values and estimated errors in values of calibration parameters, including calibrated slopes, baselines, and/or drift values for each algorithm individually (as opposed to the values themselves noted above). In this implementation, wherein the device self-calibrated values and user-dependent calibrated values are roughly equivalent statistically, e.g., such agree within +/−10%, then it may be considered safe to switch modes, e.g., to drop user-dependent calibration and only operate the device in a self-calibration mode. An example of such equivalency is shown in FIG. 13B, in which axis 365 represents sensor readings and axis 367 represents glucose values. Error bars 369a, 369b, 369c, and generally 369i represent a range of readings for different glucose values for which, if a reading falls within the error bars, the device self-calibration may be said to be valid. The points shown represent matched data pairs from external measurements, e.g., for a user-dependent calibration, these points falling along a line 371. As the user-dependent calibration values are within the error bars of the device self-calibration, the accuracy of each may be considered equivalent by the system, and consequently the user-dependent calibration may be dropped in favor of only device self-calibration for future calibrations during the session (until and unless a subsequent determination of device or data usability indicates that user-dependent calibration should once again be initiated).

Additional details of such aspects may be found in the WO 2014/158327A2 publication incorporated by reference above.

As noted above, the signal and transition criteria may be dependent on other modes, which may dictate that one or another mode is switched to, or may also indicate that the two modes may and should continue to run in parallel.

A weighting may be applied to one or both of the values from the respective mode algorithms, and weighting of one output may be greater than that of the other due to confidence in data from the respective mode. For example, if parameters in the device self-calibration suggests the same has an 80% confidence level, the output from the device self-calibration mode may be assigned an 80% weighting, leading to the value from the user-dependent calibration being assigned a 20% weighting. This type of weighting scheme 362 could occur iteratively and dynamically over time until one of the algorithms outweighs the other by so much, e.g., 95% to 5%, that the weighting itself is a criterion that allows for the triggering of the new mode. This is seen in FIG. 13A where a user-dependent calibration mode I is indicated on the left side of the diagram, a device self-calibration mode II is indicated on the right side of the diagram, and a transition region III is indicated which is an average or a weighted average of the outputs of the two algorithms. The portion of the curve 359 indicates a weighted average, while the portion of the curve 361 indicates a section in which the weighting has become heavily towards the user-dependent calibration mode, and upon meeting certain criteria, e.g., passing a threshold transition level 364, the monitoring device is caused to completely enter the user-dependent calibration mode. Similarly, the portion of the curve 363 indicates a section in which the weighting has become heavily towards the device self-calibration mode, and upon passing a threshold transition level 366, the monitoring device is caused to completely enter the device self-calibration mode.

Whether a single mode or a combination of modes is employed, calibration may be performed and sensor data may be output and displayed based on the calibration mode determined.

In a variation that combine concepts according to present principles, a hybrid mode may be entered in which the device operates under device self-calibration until such time as a user indicates via an appropriate entry on a user interface that the user believes the shown value, according to device self-calibration, is incorrect or off. In this hybrid mode, the user may enter a fingerstick SMBG value as a check on the operation of the device under device self-calibration. The value measured and entered in the CGM may be used as part of the calibration of the device, and the weighting of the value may decrease as time passes. Such a value may be used to adjust the factory calibration. In some implementations, no additional SMBG values need be entered. In other implementations, subsequent SMBG values may be entered, e.g., every 12 hours, every 24 hours, and so on. Such calibrations may serve as an iterative update calibration, increasing the accuracy of the CGM reading.

Scheduled and Unscheduled Modes of Data Transmission and Display

Figure 14:
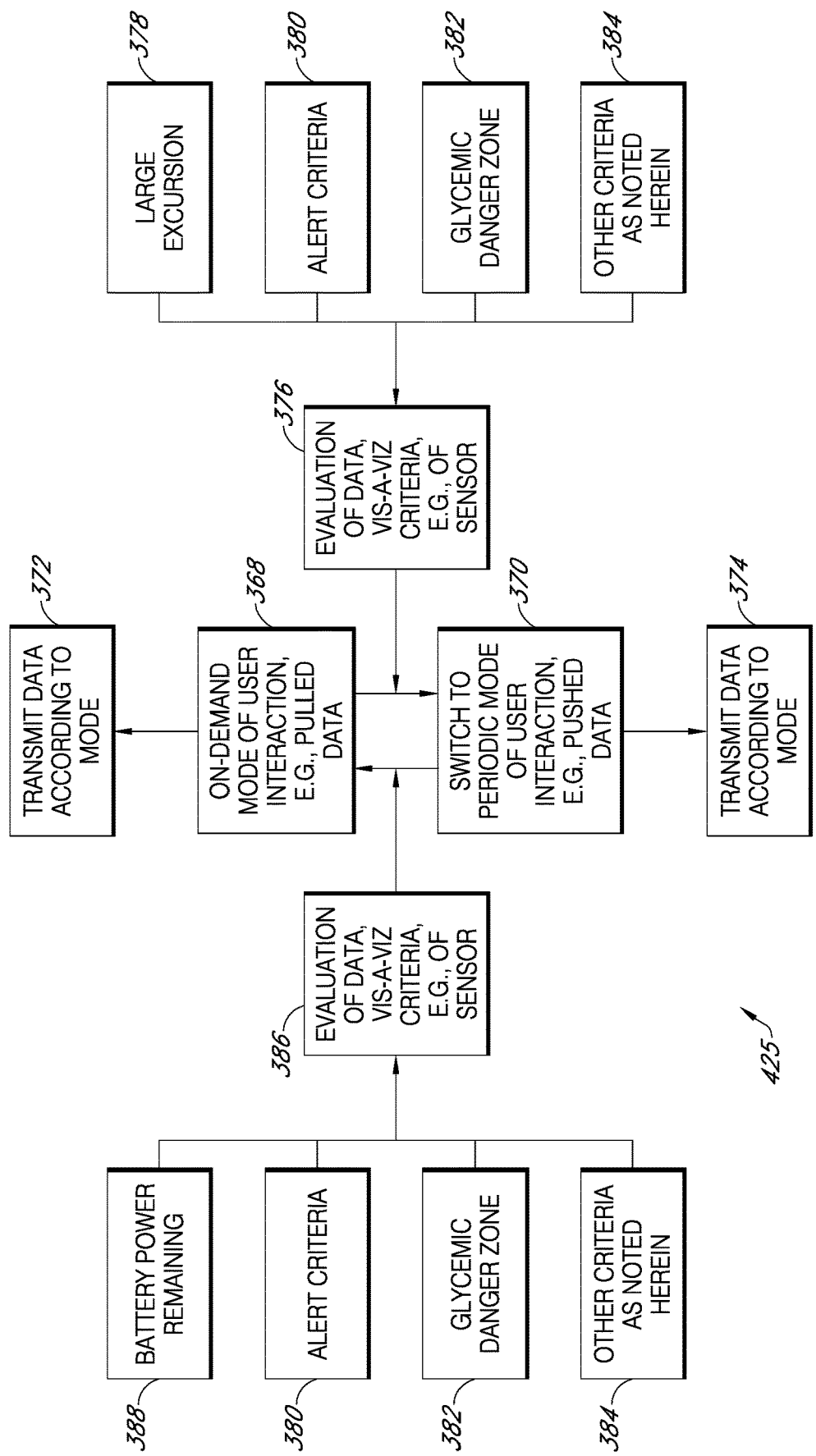
FIG. 14 is a flowchart according to present principles showing another implementation of a method of mode switching, in particular depicting transitions between data transmission modes.

Referring to the flowchart 425 of FIG. 14, another exemplary type of mode switch involves switching between different data transmission modes. In one implementation according to present principles, one data transmission mode is termed "unscheduled" and another is termed "scheduled". Scheduled transmission of a sensor transmitter to a receiver or smart phone (or, e.g., a wearable device such as a watch) generally correspond to regular periodic transmissions of data for display and analysis, though the same encompass non-periodic transmissions as well. Unscheduled transmissions may be broken down into event-driven unscheduled transmissions and user-driven unscheduled transmissions. Event-driven unscheduled transmissions may occur when the device notices a trend for which the user should be made aware, e.g., an impending hypoglycemic or hyperglycemic event. User-driven unscheduled transmissions may correspond to "on demand" types of transmissions, e.g., where the user pulls data from the sensor and transmitter (or receiver/smart phone) because they wish to view their current status. In some cases pulled data is desirable because it minimizes battery drain. However, such modes do not give the user the most information, unless even driven unscheduled transmissions are also enabled.

While automatic transmission of periodic data may provide more timely data to a user without required action by the user, it can significantly drain the battery power of on-skin sensor electronics connected to the on-skin device (as well as the receiver), which may create difficulty in miniaturizing the electronics sufficiently for comfortable wear and inexpensive manufacture. On the other hand, on-demand transmission glucose sensor data may also be employed, e.g., responsive to user requests, e.g., using near field communication. Unfortunately, on-demand transmission does not allow for timely alerts and/or alarms to be presented to the user if they do not request data at the appropriate time.

One solution is disclosed below is to provide dynamic switching between on-demand and automatic transmission modes of operation. In this way, both of the requirements noted above can be satisfied. In particular, switching occurs between a data transmission mode that stores or buffers data for on-demand transmission triggered by user request and a mode of automatic transmission of data triggered by a condition, e.g., a large excursion, the meeting of alert criteria, a glucose concentration value within a glycemic danger zone, or data delivered at a predetermined or user set frequency, e.g., once every 5 minutes, once every 15 minutes, once every half-hour, once every hour, or the like.

The mode switching may occur either at the monitoring device or at the sensor electronics. In the first case, the monitoring device can send a signal to the sensor electronics to indicate, prompt, or cause the mode switch. The data generally requires presence at the monitoring device for such a determination to be made. However, the determination to switch modes may also occur at the sensor electronics, i.e., where the signal is initially received from the in vivo sensor.

In a first step of the method, the monitoring device starts in a first or initial mode of data transmission, which may be the mode the device initializes in, a mode the device has switched to in a prior step, or the like. In FIG. 14, an exemplary initial mode of on-demand data transmission is shown (step 368). Data is transmitted according to this mode (step 372) from the sensor electronics operably connected to the on-skin sensor device, and the same is rendered on the monitoring device display. In on-demand data transmission, sensor data is generated responsive to a request by the monitoring device, e.g., a user-prompted request.

In a next step, data is evaluated against one or more criteria (step 376), and if the criteria, or, e.g., threshold associated with the same, is met, a mode switch occurs (step 370), in this example to a periodic or automatic mode of user interaction. Data may then be transmitted according to the new mode (step 374).

The reverse mode transition or switch can also occur, where in the periodic or automatic transmission mode, data is evaluated against one or more criteria (step 386), and if the requisite criteria is met or matched, a transition may be made to the on-demand mode of user interaction. Hybrid modes are also envisioned.

The criteria applied may be any of those noted above with respect to FIGS. 5-9, and certain exemplary such criteria are noted below.

One transition criteria of particular use in data transmission mode switching includes analysis of large excursions (step 378), which may be point-to-point changes in glucose concentration values above a certain change threshold, or similarly large excursions in rate of change or glucose acceleration as compared to thresholds. Predictions about such values may also be used in these calculations. Determining that a glucose concentration value is in a glycemic danger zone (step 382) may also be employed, where upon a user's glucose concentration value entering such a danger zone (where the edge of the danger zone represents a criterion such as a threshold), a mode switch may be caused to happen. Similar criteria may be defined for GUI thresholds or other glucose-related values. Notably, the device initiated transmission may be to a dedicated receiver/phone and/or to the "Internet of Things" depending on user preferences.

Another transition criteria of particular use in data transmission mode switching includes the amount of time since a user last requested a value. For example, a determined criterion may be the amount of time since a last user request for data, and a transition criteria may be a threshold duration such as eight hours. If the determined data is greater than the threshold criterion, e.g., if it has been more than eight hours since the last user request for data, a mode switch may occur, e.g., to an automatic data transmission mode.

Another transition criteria which may be applicable to transmission mode switching involves an analysis of alert criteria (step 380), e.g., user's responses to alerts or prompts provided on the user interface of the monitoring device. For example, where a mode switch may be potentially indicated, a user could be asked to confirm data on which the mode switch was predicated. A lack of such confirmation, or a contrary indication, may lead to the potential mode switch being suppressed or otherwise not performed.

Other transition criteria 384, as noted herein, may also be employed. In particular, data about other concurrent or parallel modes may be employed to inform data transmission mode switching. For example, whether the user is in a therapeutic mode versus an adjunctive mode, or whether a monitoring device is calibrated on the basis of device self-calibration versus user-dependent calibration. The decision-support mode may be particularly useful criteria to evaluate for mode switching in data transmission. For example, the system may detect that it is being relied upon for a portion of a closed-loop algorithm. In such a mode, automatic transmission may be a default setting, so that the monitoring device receives information needed to drive medicament delivery pumps. On the other hand, in an adjunctive mode, different transmission criteria may apply. For example, where the monitoring device is only being employed for educational purposes, an on-demand transmission mode may be sufficient. Transmission criteria may also be based on phase or mode where such are provided as different phases of control of an artificial pancreas system as illustrated in FIG. 15A.

Yet another transition criteria which may be employed, particularly in a transition or mode switch from an automatic data transmission mode to an on-demand mode, relates to analysis of data (step 388) about remaining battery power. For example, if sensor electronics are running low on battery power, so long as the system can determine the user is protected and otherwise within a safe glycemic state (and appears likely to remain so), an on-demand mode of user interaction may be entered in order to conserve remaining battery power.

Specific examples are now provided.

In one example, the device may start in an on-demand mode, but if the user's glucose is in a dangerous zone for a predetermined period of time, then the device may switch to an automatic transmission mode. Such a mode may be maintained until, e.g., a user acknowledges an alert or actively requests to switch back to on-demand mode. In another example, the device may start in an automatic mode, but if the user's glucose stays within a desired range for at least, e.g., four hours, then the device may switch to on-demand mode. The on-demand mode may be maintained until the user's glucose concentration value travels out of range, is predicted to go out of range, or otherwise enters an undesirable state.

In another example, mode switching may occur based on the use to which the user desires to put the data. In this regard it is noted that certain analyte monitors employ 'beacon' signals which emanate from the transmitter and which a receiver device, e.g., a dedicated device, smart phone, or the like, may then engage. Such beacon signals are disclosed in, e.g., US PGP 2013/0078912 and US PGP 2015/0123810, owned by the assignee of the present application and herein incorporated by reference in their entireties.

For simplicity the case of a smart phone will be discussed, but the situation for a dedicated receiver is similar. The smart phone may choose to engage the transmitter upon receipt or detection of a beacon signal, and following a handshaking step data may be transferred. In some cases, a mode may be entered in which communications do not occur with every beacon signal. For example, in the case of a user employing the CGM monitoring for purposes of health or fitness optimization, or weight loss, it may not be desired to receive data with every beacon signal. A benefit to not receiving transferred data with every beacon signal includes battery life, but other benefits will also be understood.

To enable the above, the system may be configured such that the smart phone does not even poll for beacon signals for a certain period of time, e.g., over the period of several beacon signals. Alternatively, the transmitter may enter a mode where it does not emit a beacon signal for a period of time. For example, instead of emitting a beacon signal every 5 minutes, it may emit one only every 15, 30, or 60 minutes. Such data will generally have less resolution and less actionable, but depending on the use to which the data is put, such resolution may be sufficient.

In another example, in an on-demand mode, if the user desired to base therapy on the data, and if the user was employing a communications scheme such as NFC, the user may perform a device 'swipe' which would be itself begin to enable the user to receive higher resolution data. First, the swipe would result in an initial higher resolution of data. Second, the swipe may in some implementations be used to indicate to the system that higher resolution data should be obtained.

Decision-Support Modes, e.g., Therapeutic (Non-Adjunctive) Versus Adjunctive (Non-Therapeutic) Mode Switching and Mode Switching Between Phases Therein Yet another exemplary type of mode switching involves switching between different decision-support modes, e.g., therapeutic, adjunctive and/or phases of control of an artificial pancreas system as described with reference to FIG. 15A. In more detail, currently all commercial CGM devices in the US are used adjunctively, which means that the device does not replace the information obtained from a standard home blood glucose meter but rather is used to complement the information obtained from the blood glucose meter. Patients are instructed to make therapy decisions, e.g., insulin dosing, based on the meter value, rather than the CGM value. For patients, it would be preferable for a device to be used therapeutically, which means the information obtained from the CGM can be used to determine therapy decisions, e.g., insulin dosing, for the patient with diabetes.

One issue with providing varying levels of control based on CGM usage is that the performance of the device, and the use of the information from the device, may differ from patient to patient. Even in a device specifically intended for therapeutic use, it would be advantageous to detect and trigger an adjunctive mode if the usability of the data for a particular patient does not meet certain standards, e.g., where the usability relates to factors noted above, e.g., accuracy, stability, reliability, or confidence in the data. A solution is to evaluate the usability of the sensor data and to switch between therapeutic and adjunctive modes in real time accordingly. As described in greater detail below, the system may be further extended to include levels of therapeutic control, e.g., as described by phases in an artificial pancreas system as described in connection with FIG. 15A.

More generally, the therapeutic/adjunctive paradigm may be broadened to a spectrum of levels of control of pump function, from an adjunctive mode where the CGM does not control the pump in any way, up to a point where analyte monitors control all medicament delivery, e.g., insulin as well as others, and no patient involvement is needed. In one exemplary implementation, the spectrum of levels of pump control may be the phases shown in diagram 445 of FIG. 15A. In this diagram, the phases progress from the system exerting no control to the system exerting the most control.

Figure 15B:
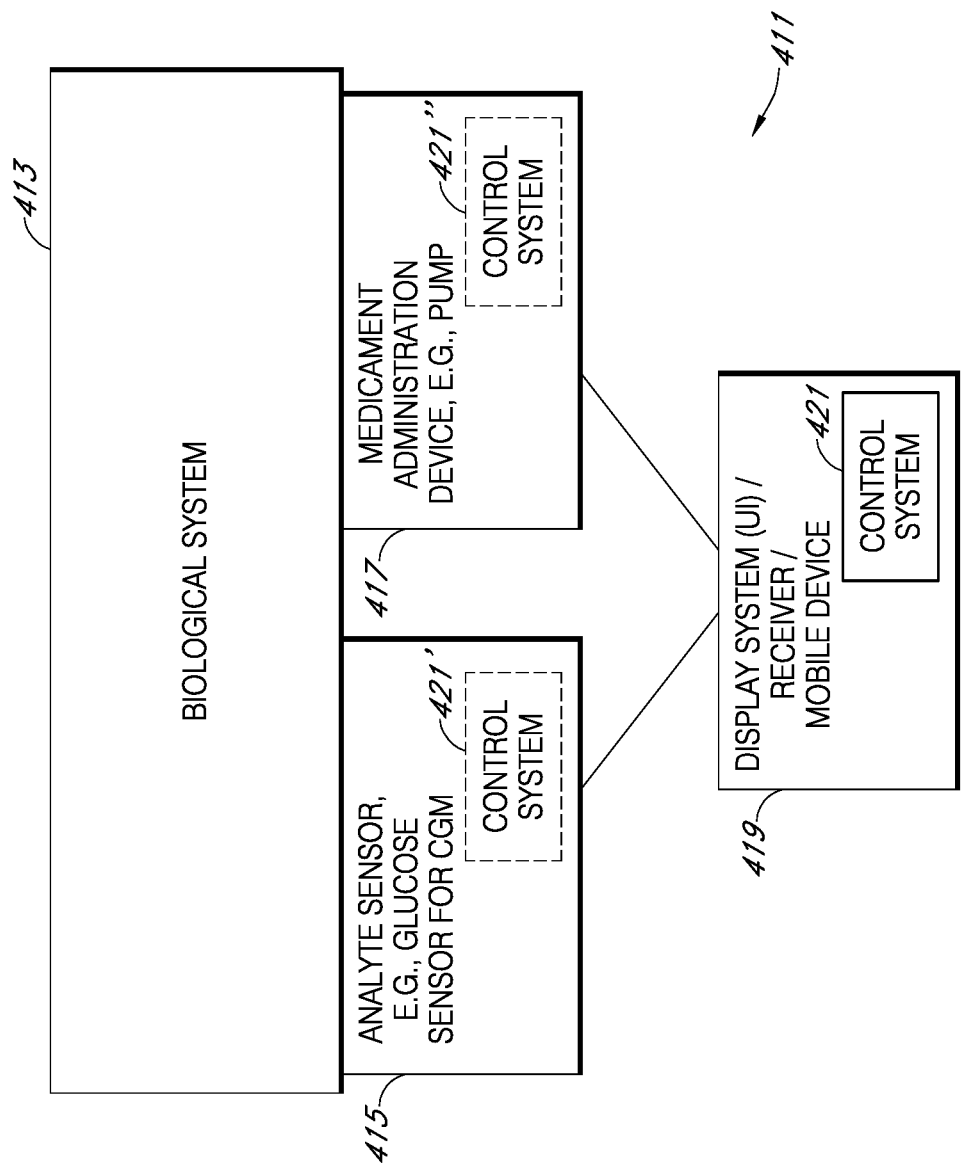
FIG. 15B illustrates a schematic diagram of an artificial pancreas system.

FIG. 15B illustrates schematically an exemplary such artificial pancreas system 411. In this system, control is exerted to various extents in respective various phases (in the implementation of FIG. 15A, for phases above and including phase 1). Generally, a control system 421 receives a signal from an analyte sensor 415 in a biological system 413 and exerts control over the analyte concentration in the biological system by controlling intake of one or more substances into the biological system using, e.g., a medicament administration device 417. The medicament administration device 417 may include, e.g., a pump, an IV, and/or one or more other devices which can controllably administer a substance into a body. In an artificial pancreas system, the analyte sensor may be that associated with a continuous glucose monitor, and the one or more substances may include insulin administered by pumps or injections. In a more advanced system, other analytes may be monitored including insulin, and the one or more substances may include, e.g., glucagon. Extending beyond the artificial pancreas, control may be extended in this way to other hormones besides insulin. While the control system 421 is illustrated in FIG. 15B as being situated within a display system 419, the same may also be situated as part of the sensor and more particularly as part of sensor electronics (see control system 421' within analyte sensor block 415) or as part of the medicament administration device 417 (see control system 421"). Alternatively, control system modules within two or more of these blocks may work together to accomplish both the control required of the phase and the potential mode switching according to implementations described here.

The use of an artificial pancreas system according to FIGS. 15A and 15B in the context of the described mode switching implementations can include the use of the mode switching implementations to drive, base, or inform switching between the various described phases of FIG. 15A (or other phases which may be developed). The use can also include use of the operating mode or phase to drive, base, or inform display on a user interface of the display system 419. In particular, the display on the user interface may include an indication of the monitored analyte, as well as in some implementations an indication of the mode or phase in which the system is operating, i.e., the mode of user interaction. For example, the user interface may display the glucose concentration as well as an indication that the artificial pancreas system is controlling for hypoglycemia but not hyperglycemia. In another example, the user interface may provide an indication that the user is, e.g., in "Phase 6" and that all control is currently being provided by the system. Numerous variations will be understood given this teaching and the examples provided below.

The display system 419 is described in greater detail below with respect to FIG. 18 and FIG. 24, but here it is noted the same may constitute a dedicated receiver or a general purpose device such as a mobile device, e.g., a smart phone.

Referring back to FIG. 15A, in an initial phase, i.e., Phase 0, shown by reference numeral 449, the use may be adjunctive only. In other words, the CGM is not used for any sort of pump control. Significant levels of information may still be provided in this phase, as well as in the other phases. However, such information may be indicated on a user interface so as to be only for tracking purposes, determining trends, or for educational purposes. For a user who is pre-diabetic, phase 0 may be the only phase needed.

In a next phase, i.e., phase 1, shown by reference numeral 451, an insulin pump may be controlled so as to turn off at times when the user is encountering low glucose levels. In phase 1 and subsequent phases, it will be understood that while pump actions are disclosed, the same may be accomplished by an indication on a user interface of the monitoring device directly employable by a user for dosing, e.g., by injection, ingestion, or the like.

In a subsequent phase, i.e., phase 2, shown by reference numeral 453, phase 1 may be enhanced, e.g., by allowing hypoglycemia predictions to occur, and causing alarms when such conditions are present or likely to occur. If such alarms go unheeded, a phase 2 system may cause a reduction or cessation of insulin if the user's glucose level is below a threshold.

In a next phase, i.e., phase 3, shown by reference numeral 455, phase 2 may be enhanced, e.g., by including a step of insulin dosing when the user's glucose level passes above another threshold, i.e., a high threshold. In a subsequent phase, i.e., phase 4, shown by reference numeral 457, the system may be essentially closed loop, except for mealtime manual assist bolusing. In particular, the system may cause insulin reduction or cessation at low glucose levels, and insulin dosing at high glucose levels. However, due to glucose variability at meal times, bolusing at such times may be performed manually.

In a next phase, i.e., phase 5, shown by reference numeral 459, such mealtime manual assist bolusing may be removed, and the system may be closed loop for insulin. In a final phase, i.e., phase 6, shown by reference numeral 461, the closed loop system may be extended from just insulin to contemplate and control other hormones as well, for a closed loop multi-hormone system.

In one implementation, therefore, the above mode phases may be employed in a control scheme, and mode switching may occur between the various phases. While the modes or phases or have been described in the order of least control to most control, there is no requirement that the system proceed in such an order (in either direction) in the control of a therapy. Each mode or phase is stand-alone, and may be entered or exited independently according to the determined data and mode switching criteria. For example, the system may transition from phase six to phase zero, and more generally from phase i to phase j, where i and j are any of the phases zero to six.

Figure 15C:
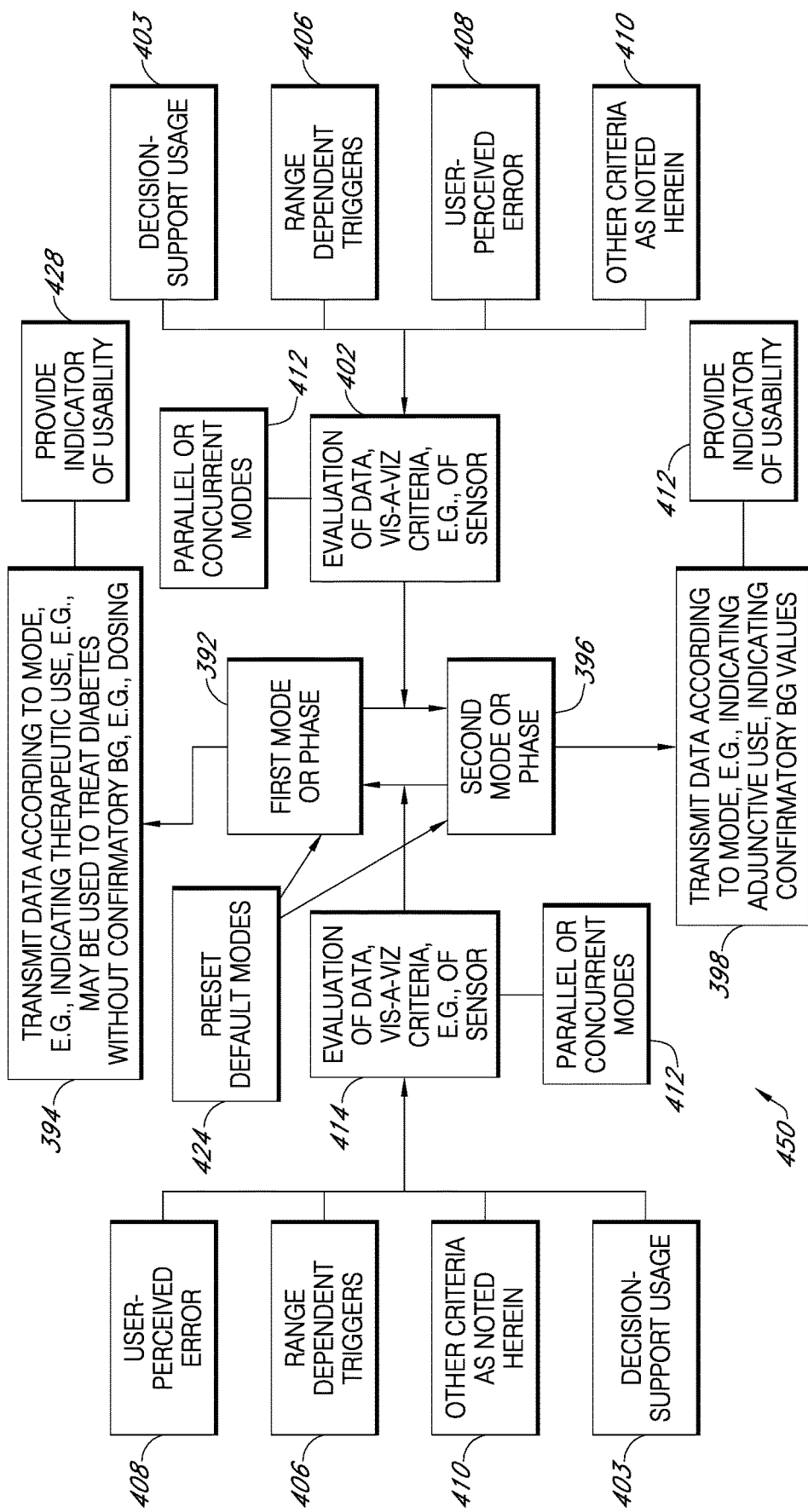
FIG. 15C is a flowchart according to present principles showing another implementation of a method of mode switching, in particular depicting transitions between control modes, e.g., various therapeutic and adjunctive (non-therapeutic) modes, and which may be applicable to the modes shown in FIG. 15A.

Mode switching between phases is illustrated in greater detail by the flowchart 450 of FIG. 15C. An exemplary initial mode or phase is posited (step 392). Data is transmitted according to this mode (step 394), and such may indicate (step 428) the use of the data. If the phase has a therapeutic component, the display may so indicate. For example, the UI may indicate that the data determined may be used to treat diabetes without confirmatory external meter values for, e.g., insulin dosing. In so doing, the data may be employed by the user to determine insulin dosing in the context of a bolus calculator or the data may be directly transmitted to an integrated pump controller. In the language of artificial pancreas phases, the UI may indicate the current phase, e.g., "Phase 1—System Will Stop Insulin at Low Glucose".

In a next step, data is evaluated against one or more criteria (step 402), and if the criteria, or a threshold associated with the same, is met, a mode switch occurs (step 396), in this example to a second mode, e.g., a different phase. For example, the mode may switch to Phase 0, and the UI may so indicate by a displayed notation such as "Phase 0—Readings are for Adjunctive Use Only". Data may then be transmitted according to the new mode (step 398). Such may include displaying the data to a user in such a way to indicate its usability according to this second mode or phase (step 412), e.g., in the above example where Phase 0 was switched to, the display may indicate that other information such as external meter values should be used to make actual treatment decisions for the user's diabetes. In this specific example, the data displayed may also provide an indication of user interaction, e.g., that CGM data may not be relied on fully for calculating insulin dosing, whether used in a bolus calculator or in an integrated pump controller.

The reverse mode transition or switch can also occur, where in the second mode or phase, data is evaluated against one or more criteria (step 414), and if the requisite criteria is met or matched, a transition may be made back to the first mode or phase or to a third mode or phase.

The criteria applied may be any of those noted above with respect to FIGS. 5-9 (step 410), including data usability, and certain such criteria are described in greater detail below.

For example, therapeutic use for a pre-diabetic user or patient may only require relative confidence that the display is providing an accurate zone of glycemia and/or an accurate post-meal rate of change. So long as these are believed to be accurate to a predetermined criterion, e.g., a threshold level, then the device may be essentially therapeutic in nature. In contrast, for an intensively-managed insulin-dependent type I (or II) diabetic, the therapeutic mode may have criteria that requires a certain level of accuracy or confidence in the full range of glycemia (40-400 mg/dl) and at all physiological rates of change.

As a particular example, in a therapeutic mode, a user may be instructed to examine the display device, e.g., receiver or smart phone, and verify that at least three acceptable data points in a row have been received immediately prior to the time period in which the therapeutic decision is to be made, e.g., dosing. Instead of user examination, the system may automatically only make a decision recommendation if the three immediately prior consecutive values exist, have been reported, or are "good" or "satisfactory" according to a predetermined criteria. For example, the previous values may be prior "five-minute" values, where values are transmitted from the sensor and received in the receiver every 5 minutes. Additionally, based on prior sensor data values, a trend of the glucose value may be determined and displayed, e.g., a trend arrow may be displayed indicative of whether the glucose value is rising or falling (and may also indicate a rate of change). Such aspects are important in the determination of a therapeutic recommendation, and thus by requiring the same an additional level of safety is achieved. In one specific implementation, three immediately prior trend points are required, along with a trend arrow and a sensor glucose reading, before therapeutic decision support is allowed based on the CGM data. In some cases, in the absence of such, the adjunctive or non-therapeutic mode may be entered. In other cases, again in the absence of such data, the therapeutic mode may be maintained, but with an appropriate warning to the user, or alternatively an indication as to how clinically actionable the data is, e.g., whether dosing may be based on the same or not.

While three immediately prior consecutive values have been disclosed above, it will be understood that the number of values, their timing, and whether they are consecutive may vary, and in general the prior values may be such that a trend can be determined.

The trend or data points discussed above are generally displayed on a graph, and user examination can reveal if the immediately prior three data points appear and are consistent with other trend data or user expectations. Such examination and determination are easily performed on a receiver or smart phone or other such device with a similar form factor. However, if the device is smaller, such as the user interface on a smart watch, screen real estate may be insufficient for display of a trend graph. In this case, trend arrows may be displayed, along with the current glucose value, and the same employed by the user for therapeutic decision support. The slope of the arrow may indicate the velocity of the analyte concentration value trajectory, or the same may be indicated with multiple arrows, e.g., one up arrow for a slow rise, two up arrows for a moderate rise, and three arrows for a rapid rise (with corresponding down arrows for decreasing analyte concentration values). In another variation, the user interface of the wearable device, e.g., smart watch, may directly indicate the clinical or therapeutic actionable nature of the data. For example, the user interface itself may indicate whether it has received immediately prior data values, particularly of sufficient quantity to indicate a trend, e.g., by comparing the number of values it has received with the number of values it should have received given the known transmission rate of the data from the sensor.

In light of the above, one transition criteria of particular use in mode switching between therapeutic and adjunctive modes, or between phases of control as in FIG. 15A, includes a step of determining decision-support use (step 403), which may in turn control the criteria for determining usability of data (step 402).

Another type of data and accompanying transition criteria which may be advantageously employed in certain implementations of such mode switching include those related to detected faults, e.g., the likelihood of an "end-of-life" or other failure mode. Such faults may be detected by comparing current data to known failure modes as identified by signatures or patterns in trace data. Additional aspects are described elsewhere and in U.S. Provisional Patent Application Ser. No. 62/009,065, incorporated by reference above.

Another aspect which may bear on criteria employed includes use (step 424) of preset default modes. That is, modes may default to predefined ones based on factors such as, e.g., time of day, glucose level, or the like. As one example, a user may desire that their device be used adjunctively during the day and therapeutically at night, e.g., with varying levels of control and more granularly as the phases shown in FIG. 15A, e.g., to warn and control against low glucose at night (phase 2), but to give the user more control during the day (only phase 1).

Yet another type of data and accompanying transition criteria include those relating to glucose context, e.g., whether the glucose context is nighttime hypoglycemia, adjusting insulin dosing, or other such contexts. For example, for the same patient, a therapeutic mode, e.g., phase 1 control, may be used during nighttime hypoglycemia whereas an adjunctive mode may be used when determining insulin dosing so as to treat hyperglycemia.

The evaluation against transition criteria could further employ internally detected parameters to detect shifts in sensitivity including those from self-diagnostic routines, e.g., using impedance to detect shifts in sensitivity as discussed above and further in the applications incorporated by reference above. The same may be performed on a regular basis or when an error is perceived.

Another type of data and accompanying transition criteria which may be employed involves the use of user-perceived error (step 408). As described above in the context of other types of mode switching, if a user specifically indicates an error or provides a greater than average number of external meter values, or provides external meter values without prompting, a user-perceived error may be inferred. Accordingly data usability may be decreased and/or the user may be prompted to enter one or more reasons as to the perceived errors.

The evaluation may include a comparison of current or recent data to historic glucose concentration values, e.g., ranges, means, patient specific profiles, or the like. If the data does not follow the patient's individual normal glucose profile according to the criteria, e.g., within a threshold, the patient may be prompted as to whether they believe the data to be unusually high or low, whether the patient otherwise perceives an inaccuracy, e.g., feels that an alert or alarm constitutes a false alarm, or whether the patient has a reason explaining an unusually high or low or abnormal reading. Similarly, an option may be provided on the user interface for the user to flag outlier data.

In the same way, the user interface could provide an option for the patient to state whether they feel they have high blood sugar or low blood sugar, and the monitoring device may perform a system check to determine whether the determined glucose concentration value is consistent with the feeling. Such an option may also be employed to identify hypoglycemia unawareness in a patient, e.g., by asking whether the patient feels low when CGM data shows that the patient has entered a hypoglycemic range.

In a similar way, the monitoring device could identify an event, e.g., such as high or low glucose, and ask the user to identify feelings associated with the current event, or potential causes for the event. In both cases, the user may select from a list of potential feelings or causes.

In some cases, the monitoring device could prompt for a confirmatory blood glucose meter reading. Such a meter reading would not necessarily be used for calibration, but as confirmation of a reading from the CGM. The value may be used to adjust calibration parameters or just for information.

The evaluation may depend on other parallel or concurrently running modes (step 412). In particular, transition criteria or triggers may be modified depending on such other modes. In one case, a data transmission mode may be used in the determination of decision-support mode switching. In another case, a calibration mode may be used in the same determination.

User-selected responsiveness may also be employed as described above. In particular, users may select whether they prefer smooth data with a time lag or noisy data that is more responsive to actual glucose changes.

Whatever the criterion or criteria used, if determined data satisfies the criteria or criterion, e.g., meets, matches, or exceeds a threshold level, or in another way satisfies the criteria or criterion, mode switching may occur. In some cases, the subject mode switching, e.g., therapeutic versus adjunctive, or from one phase to another, may be accompanied by other mode switching, e.g., device self-calibration versus user-dependent calibration.

Whether to switch modes, or what mode to switch to, may also be based on a glucose range the patient is currently in. Put another way, range-dependent triggers may be employed (step 406) to inform mode switching. For example, a first mode may be triggered only for hypoglycemia, while a second mode is triggered if the patient is hyperglycemic.

Figure 16A:
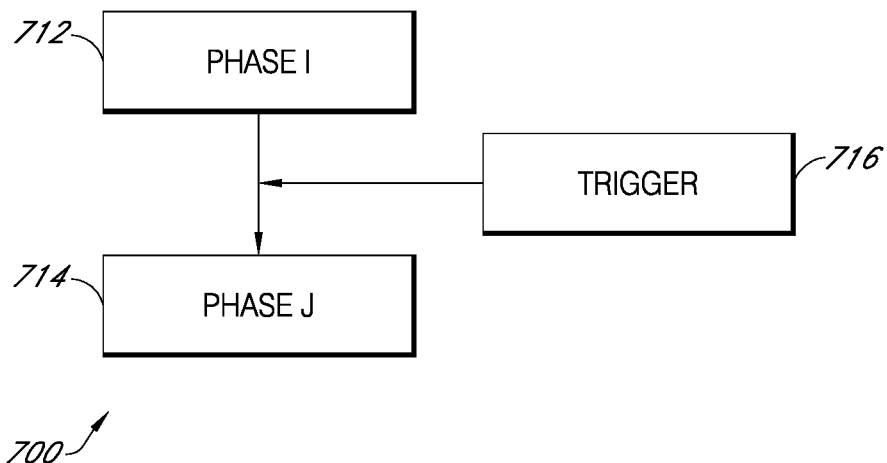
FIG. 16A is a flowchart showing mode switching between phases described in an artificial pancreas system.

FIG. 16A is a flowchart 700 illustrating a particular implementation of mode switching between different phases of an artificial pancreas system as described in connection with FIG. 15A. In this figure, an initial phase (I) 712 is illustrated which upon occurrence of a trigger 716 transitions the operating mode to phase (J) 714, generally with a new mode of operation and a new mode of user interaction, particularly as displayed on a user interface of the monitoring device.

Figure 16B:
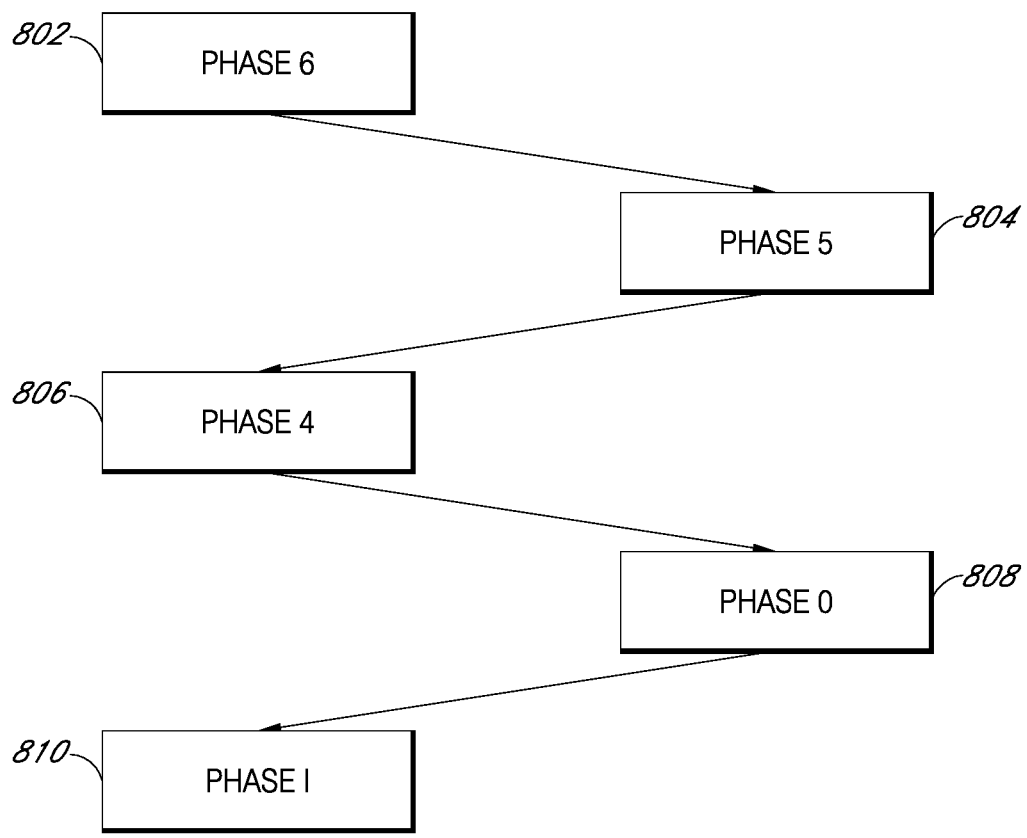
FIG. 16B is a diagram showing mode switching between phases described in an artificial pancreas system.

FIG. 16B illustrates a particular set of transitions between phases. For example, a system in phase 6 (802) may be caused to transition to phase 5 (804) upon the occurrence of a particular hormone's sensor failing. A system in phase 5 (804) may be caused to transition to phase 4 (806) upon the occurrence of an event such as user detection of perceived errors, especially ones that relate to the accuracy of mealtime highs. A system in phase 4 (806) may be caused to transition to phase 0 (808) upon the occurrence of a lowering of signal usability, because the lowered signal usability may cause an accurate prediction to no longer be possible. As another example, a system in phase 0 (808) may be caused to transition to phase 1 (810) upon the obtaining of a signal of greater data usability, allowing the system to obtain accurate readings again.

Numerous other types of transitions will similarly be understood given these teachings, and a non-exhaustive set of such transitions are shown below in Table I.

TABLE I

| ORIGINAL MODE | TRIGGER(S) (exemplary and non-exhaustive) | NEW MODE |
|---|---|---|
| First level of user interaction | Change in usability of data | Second level of user interaction |
| User-dependent calibration | Increasing usability of self-calibration | Device self-calibration (factory) |
| Device self-calibration (factory) | Fault detected in calibration | User-dependent calibration |
| On-demand information | Gui increased, entry into glycemic danger zone, entry into hypo/hyper states | Regular or periodic pushed information |
| Regular or periodic pushed information | Gui decreased, exit from glycemic danger zone, exit from hypo/hyper states | On-demand information |
| Adjunctive | Increasing Usability Of Data, Increasing Confidence In Data, User Desire For Therapeutic Support | Therapeutic |
| Therapeutic | Decreased Signal Usability, Fault Detected, User Choice | Adjunctive |
| Adjunctive & user-dependent calibration modes | Increased signal usability & increased confidence in calibration | Therapeutic mode, device self-calibration mode, or both |
| On-demand information & device self-calibration | Fault, decrease in signal usability, entry into glycemic danger zone, increased gui, entry into hypo/hyper states | Pushed information, user-dependent calibration, or both |
| Phase 6 | Analyte sensor (not insulin) fail | Phase 5 |
| Phase 6 | All analyte sensors decrease in signal or data usability | Phase 0 |
| Phase 5, 4, 3, 2, 1 | Glucose sensor decreases in signal or data usability | Phase 0 |
| Phase 5 | User detection of perceived errors | Phase 4 |
| Phase 4 | Decrease in signal usability | Phase 3, 2, 1, or 0 (depending on signal usability) |
| Phase 0 | Increase in signal usability to point where analyte concentration value is trusted but not predictive value | Phase 1 |

This process responsiveness (of mode or phase to criteria such as signal usability) may be implemented in some cases by causing different commands to be sent to an insulin pump controller. For example, and referring to the flowchart 475 of FIG. 16C, in a mode or phase that is at least partially therapeutic (step 430), pump control may be exerted at least partially under control of the monitoring device (step 436). And as noted if data usability becomes very low, the monitoring device may be caused to transition to an adjunctive mode (step 432) where the monitoring device does not control the pump.

According to, e.g., the sequence of FIG. 15A, various levels of pump control may be exerted short of full pump control. Alternatively, even if data usability is high, a user or clinician may choose to exert, or the monitoring device may be configured to switch to a mode exerting, a varying or reduced level of pump control.

The levels of pump control exerted in step 436 may be considered to select an aggressiveness of the pump control. Specific examples of such aggressiveness levels are now described.

Figure 16C:
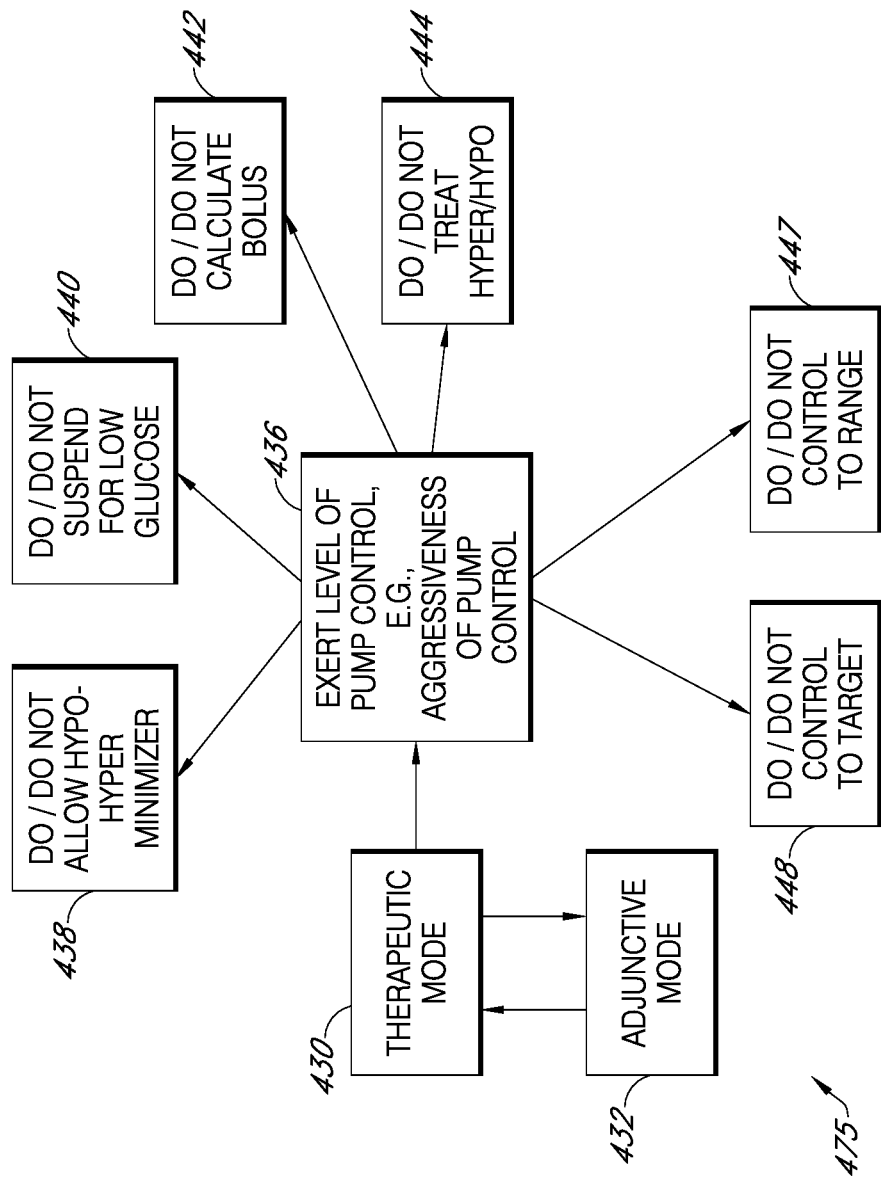
FIG. 16C is a flowchart according to present principles showing another implementation of a method of mode switching, in particular depicting exertion of varying levels of pump control within therapeutic modes or phases.

A number of actions are described within FIG. 16C, and many of these are described as "do or do not" perform a given step, e.g., treat hypoglycemia, control to target, calculate bolus, etc. As part of a procedure within phase 0, the "do not" portions of these steps may be generally employed, e.g., do not allow hypo/hyper minimizer (step 438), do not suspend for low glucose (step 440), do not calculate bolus (step 442), do not treat hyperglycemia/hypoglycemia (step 444), do not control to range (step 447), and do not control to target (step 448).

The "do" portions of the steps may then be enabled to perform one or more functions within a system for phased therapeutic control, e.g., as noted with regard to FIG. 15A. For example, to accomplish phase 1, the system may be configured to suspend pump actions for low glucose concentration values (step 440). To accomplish phase 2, a level of prediction may be enabled, and alarms may be caused if hypoglycemia is predicted. The same may be accompanied by a reduction or cessation of insulin below a predetermined threshold.

To accomplish phase 3, the system may be configured to allow a "hypo-hyper minimizer" (step 438), where the same is a closed-loop system that only controls insulin using sensor data at low and high glucose levels, rather than using the same also within target ranges. To accomplish phase 4, the system may be configured to calculate a bolus (step 442) during mealtime. In this way the system acts in many ways closed loop but allows additional user control during particularly uncontrolled times, e.g., meal times area To accomplish phase 5, the system made more generally be configured within to treat hyperglycemia and hypoglycemia, e.g., by dosing insulin and, e.g., glucagon, as appropriate. Finally, to accomplish phase 6, other hormones may be employed to provide even greater balance and stability to the patient's biochemistry. In so doing, the system may control to a target value of the hormone (step 448), or alternatively to a target range (step 447).

Within these phases, it will be understood that the exerted level of pump control may vary. For example, closed-loop control such as available in phases 4-6 may in certain implementations be used only within certain glucose ranges, e.g., 20-70 mg/dL. Ranges may be individually-controlled based on certain criteria and whether the mode is adjunctive or therapeutic or based on the phase. For example, depending on the evaluation step, there could be different criteria in adjunctive mode for treating hyperglycemia versus hypoglycemia.

Figure 17:
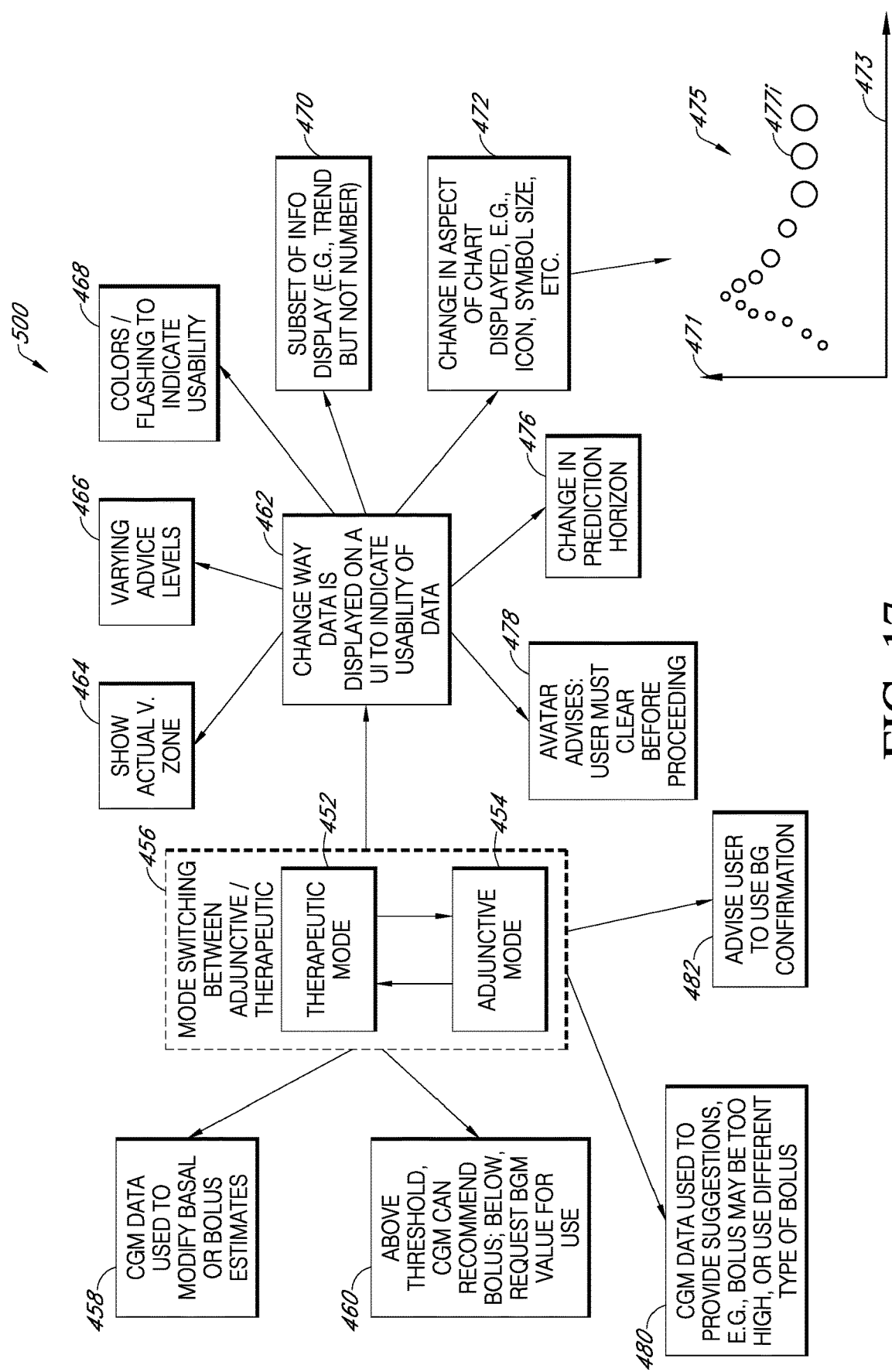
FIG. 17 is a flowchart according to present principles showing another implementation of a method of mode switching, in particular depicting responsive processing and display of data according to mode switching between therapeutic and adjunctive (non-therapeutic) modes.

FIG. 17 is a flowchart 500 illustrating processing and display changes which may be caused or performed when mode switching (step 456) occurs between modes. For simplicity, FIG. 17 contemplates a therapeutic mode 452 and an adjunctive mode 454, although similar UI aspects can be extended to other types of mode switching as well as switching between phases as described above. Generally, the way in which data is displayed on the user interface may be changed to indicate at least in part the usability of the data (step 462).

Figure 18A:
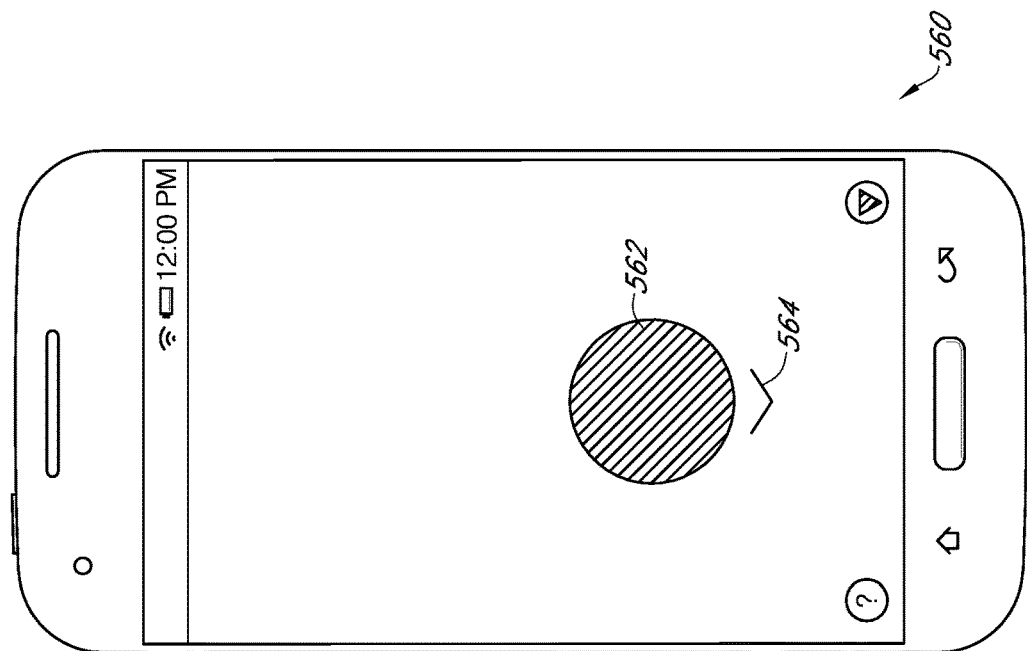
FIG. 18A-18D illustrate exemplary user interfaces which may be employed according to present principles.
Figure 18B:
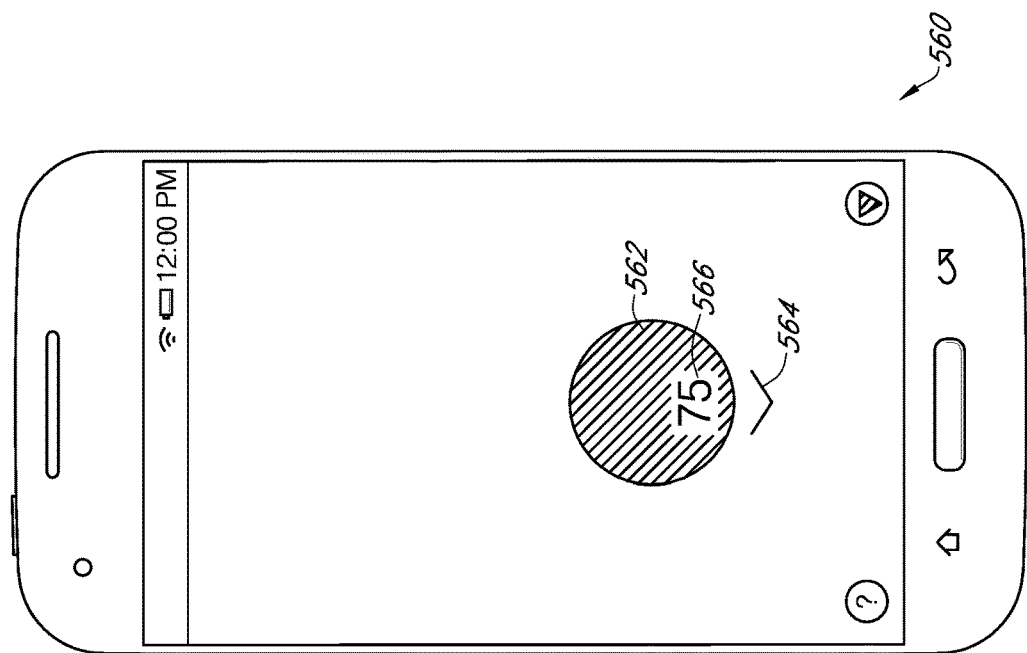

In one example, an actual glucose concentration value may be selected to be shown versus a zone of glucose concentration values (step 464). This situation is also illustrated in FIGS. 18A and 18B, where the figures show a monitoring device 560 having a glycemic range 562 illustrated by a color indication, as well as an indicator 564 of a trend, in FIG. 18, a downward trend. In FIG. 18A, a numerical value 566 is illustrated, showing a glucose concentration value of 75 mg/dL, while in FIG. 18B, no such value is displayed. In the former, the confidence level or usability of the data satisfies a criterion, e.g., is greater than a threshold level, allowing the data to be illustrated. In the latter, the confidence level or usability has not met the criterion, e.g., is below the threshold, and thus display of the numerical value is suppressed. In both cases, the confidence level or usability of the data about the glycemic range, as well as the rate of change, satisfies the criterion, e.g., is higher than the threshold, and thus this data is present on both exemplary user interfaces.

Referring back to FIG. 17, in another implementation, different levels of advice or help, e.g., such as displayed help from an avatar or other on-screen display, may be provided to a user (step 466). For example, in a therapeutic mode in which a bolus may be enabled to be calculated, an avatar may inform the user about an amount of insulin directed to be pumped. In a mode employed for educational purposes, an avatar may provide not only glucose data, but a significant level of suggestion and information about a current glycemic range, or other data which may be useful to a user in developing a knowledge of CGM operation and disease management.

Additional details of systems and methods for use of avatars are disclosed in US Patent Publication No. 2010/0261987-A1; and US Patent Publication No. 2014/0184422-A1, both of which are owned by the assignee of the present application and herein incorporated by reference in their entireties.

In yet another implementation, an avatar may be employed to appear and inform the user about how they should be using their device (step 478). In an implementation, a user may be required to acknowledge receipt of such data before viewing glucose data again. Such an implementation may be particularly advantageous where it can be deduced that a user is not using their device correctly or is not consulting the same frequently enough.

Figure 18D:
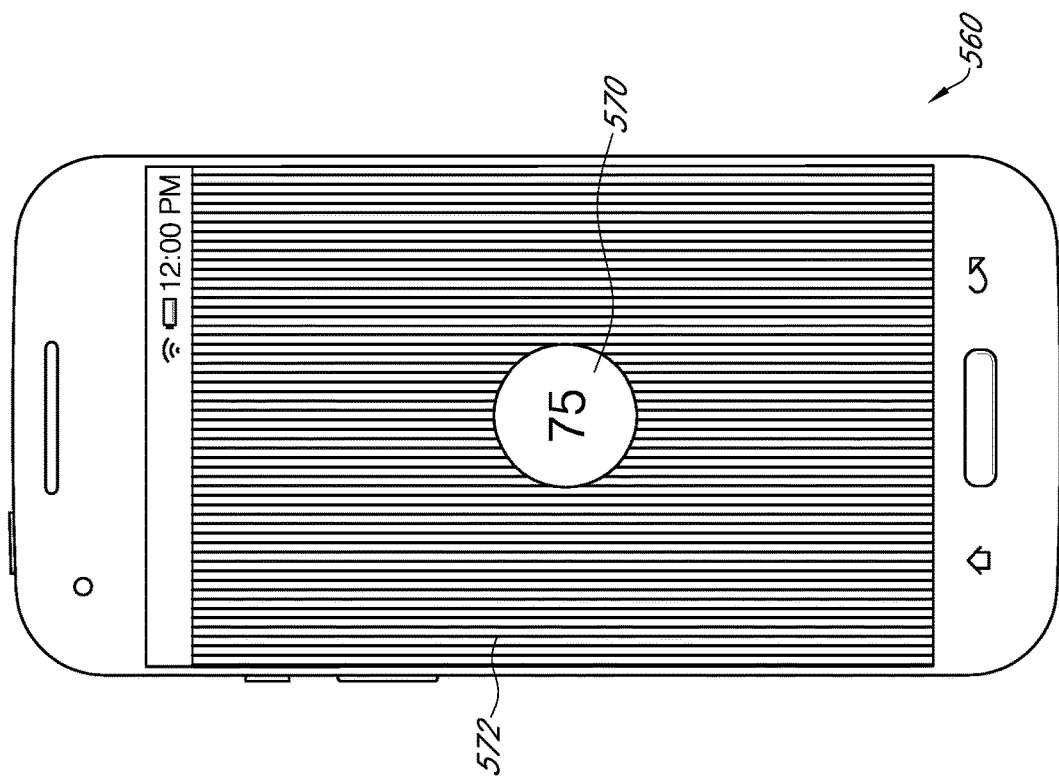
Figure 18C:
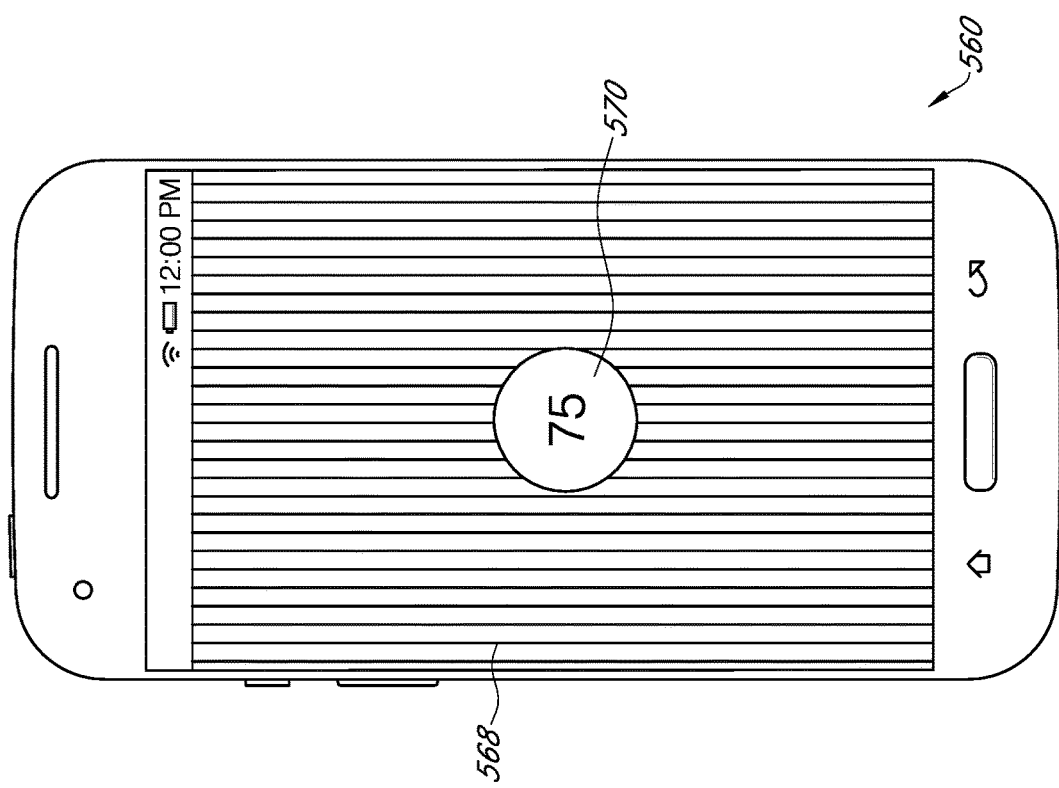

In another implementation, colors or other visual effects may be employed to indicate mode and/or usability of determined data (step 468). For example, and referring to FIGS. 18C and 18D, FIG. 18C shows a monitoring device 560 in which one mode is indicated by a widely spaced vertical line pattern 568. FIG. 18D shows the same monitoring device 560 in which a different mode has been entered, and the same indicated by a different (more narrowly spaced) vertical line pattern 572. In both cases, a common glucose reading 570 is displayed on the background pattern. Using this implementation, a user can quickly and visually identify the mode their device is in. Patterns may be implemented which represent multiple modes as well. For example, a pattern may represent a therapeutic mode in which user-dependent calibration is performed while another pattern may represent that an adjunctive mode is operating in which device self-calibration is employed. Other combinations and implementations will also be understood given this teaching, as is described above and in applications incorporated by reference.

The level of data usability may be indicated in other ways as well, e.g., by the altering of a data indicator on a user interface to indicate a level of data usability. In one example, the displayed glucose concentration values themselves may be caused to flash or be steady to indicate usability, e.g., flashing data may be associated with a lower usability, e.g., may have less reliability or a lower confidence level, than steadily-rendered data. Another way to indicate usability by altering a data indicator includes altering another aspect of a chart display (step 472), as shown in the inset chart 475 in FIG. 17, in which points 477i represent glucose concentration values on an axis 471 and which are plotted against time on axis 473. The size of a dot representing glucose on the trend graph may be made larger when its usability is less, e.g., where its corresponding data is of a lower confidence. In this way the dot size indicates range information, i.e., the size of the dot can represent the range. Such may then show a difference between more usable (in this case reliable) data having a value of, e.g., 78 mg/dL, versus less usable data, having a value within a range of 60-90 mg/dL. Other variations will also be understood, including the use of large dots to indicate greater data usability.

Figure 19:
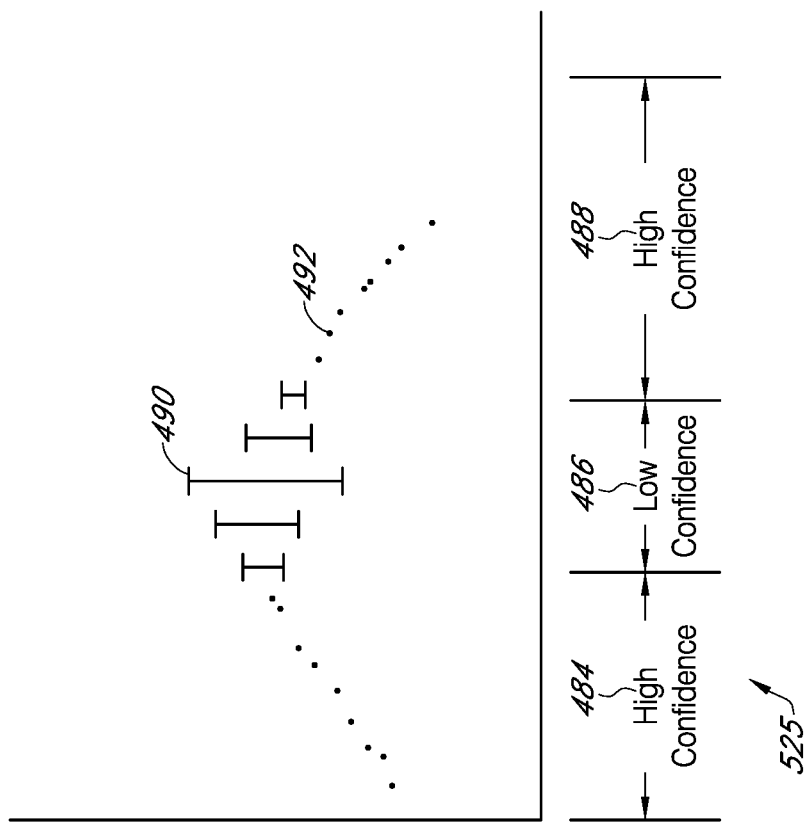
FIG. 19 is a chart showing ways to depict data of various confidence levels.

Another method to indicate data usability on a user interface is to show ranges versus numbers in a selective fashion as shown by the chart 525 of FIG. 19. In this chart, certain data 492 are illustrated by dots while other data 490 are illustrated by ranges of values in a way similar to error bars. The ranges and dots are indicated on the x-axis as being of high data usability, e.g., in a high confidence range 484 and 488 (the dots 492), or as being of low data usability, e.g., in a low confidence range 486 (the range bars 490).

In another implementation, a subset of data may be displayed (step 470) in order to indicate, e.g., a lack of confidence in certain un-displayed information. In other words, a restricted information display may be used to show, e.g., a rate of change arrow, but not an actual glucose concentration value. In this way, data is not displayed unless it satisfies a criterion for usability. Such an implementation may be similar to the information displayed on the monitoring devices of FIGS. 18A and 18B.

Referring back to FIG. 17, in yet another implementation, a change in the prediction horizon may be displayed where the same depends on the usability of the signal (step 476). The change in prediction horizon may include whether the device employs a prediction horizon, whether the device displays a prediction, as well as whether alerts or alarms are employed based on such predictions. In particular, the prediction horizon may be varied from 10, 20, or 30 minutes in the future, depending on the confidence of the prediction, which may be affected by usability-related parameters and variables such as signal quality, confidence in a calibration, confidence in resulting data, acceleration, or the like.

In the particular case of the adjunctive mode, the display may continue to show glucose concentration values, but an alert or alarm screen could indicate a warning that external meter values should be used to confirm CGM values prior to dosing (step 482).

In one specific example, an insulin bolus calculator on the monitoring device may run in an adjunctive mode or therapeutic mode based on the relative confidence in the CGM data, which in turn can be part of a transition criterion or criteria. For example, if the confidence is above a threshold, then the bolus calculator can determine a recommended insulin bolus without input from an external meter (step 460). However, if the confidence is below the threshold, then the bolus calculator may request external meter reference values for use in bolus estimation.

In another specific example, an insulin pump may be programmed with basal estimates by the user, while bolus estimates may be entered by the user. In an adjunctive mode, CGM data may be used to make suggestions (step 480), such as "bolus may be too high", or "may need a different type of bolus". In therapeutic mode, which may also depend on phase, CGM data may be employed to modify the basal or bolus estimates, with or without user confirmation (step 458).

Figure 20:
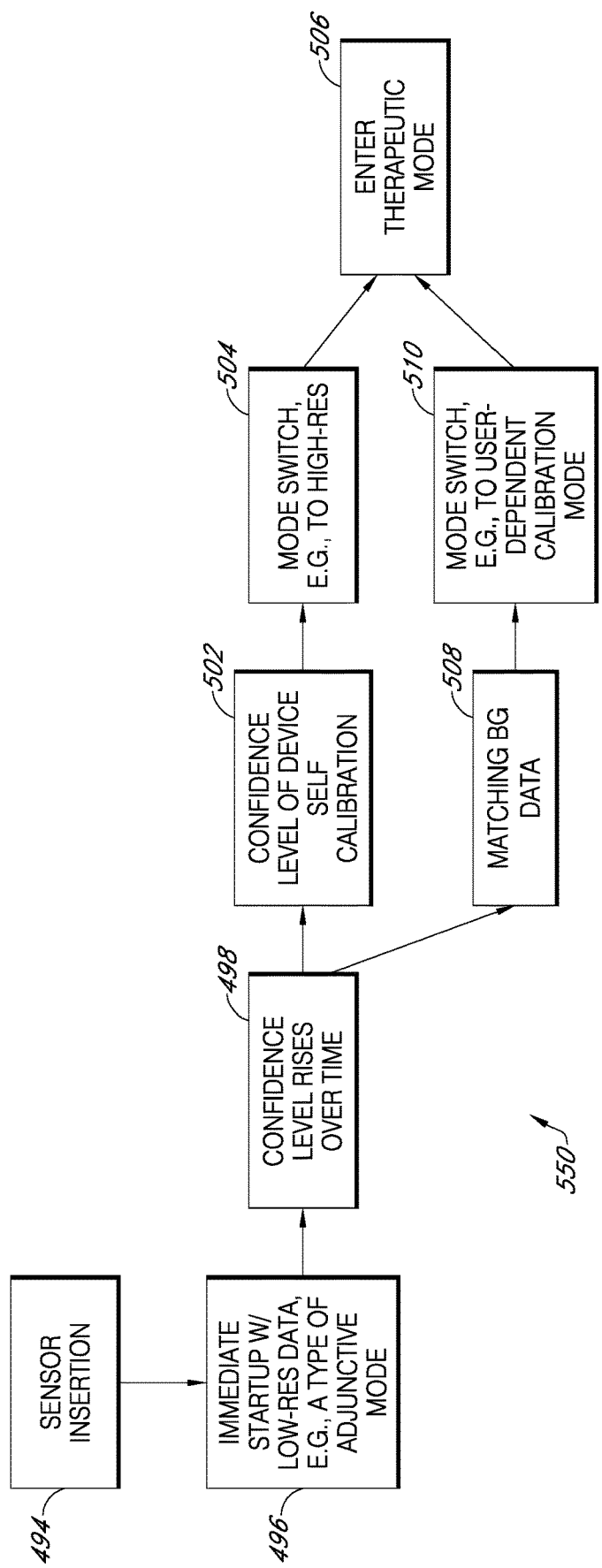
FIG. 20 is a flowchart according to present principles showing another implementation of a method of mode switching, in particular depicting multimodal transitions.

In another specific example, as shown by the flowchart 550 of FIG. 20, startup of the monitoring device may occur immediately after sensor insertion (step 494), e.g., within 15 minutes or the like, and low-resolution data may be immediately displayed (step 496). This is in contrast to many present systems in which sensors do not start up until, e.g., two hours, after insertion. Low-resolution data may be displayed that includes, e.g., a glycemic range the patient is in, glucose range information, or other data which may be considered adjunctive-mode-type data. Over time, a confidence level or other indicator of the usability of the data may rise (step 498). This rise may occur in a number of ways. For example, an external meter value may be provided (step 508) that either correlates to what the CGM estimates the glucose concentration value to be and/or the external meter value entered may trigger a mode switch to a user-dependent calibration mode (step 510), and if the usability is high enough, a therapeutic mode may be entered (step 506). The usability may also dictate the phase in which the device is operating, if such phases are enabled (see FIG. 15A). In another alternative, an increase may occur in a level of certainty in the device self-calibration mode (step 502) sufficiently so as to display glucose concentration values at a higher resolution (step 504), and thus justify a transition if desired by the user into a therapeutic mode or phase (step 506).

In other words, an adjunctive mode is maintained until external meter data indicates a mode switch to user-dependent calibration, at which point sufficient resolution may be achieved to perform a further mode switch of the adjunctive mode to the therapeutic mode. Correspondingly, a criteria for determining the calibration mode, e.g., whether or not to use user-dependent calibration, may be based on whether or not the therapeutic mode versus the adjunctive mode has been triggered. For example, if the therapeutic mode has been triggered, it may be desirable to switch to a user-dependent calibration mode. Similarly, if the adjunctive mode has been triggered, it may be desirable to switch to a device self-calibration mode if calibration parameters allow. In these fashions, FIG. 20 illustrates an interplay between the calibration mode and the therapeutic/adjunctive use modes, as well as their potential effects on each other.

As one example, signal usability of a monitoring device may cause the same to be operating in a user-dependent calibration mode. For example, the monitoring device may be registering a fault in the sensor due to a shower spike. However, if the fault is resolved, and confidence rises in the device self-calibration, at some point the device self-calibration may be allowed to "take over" and reduce the need for user-dependent calibration. At the same time, if confidence also rises in the signal usability, the decision support mode may be caused to transition from an adjunctive one to a therapeutic one, or in the case where phases of control are implemented, to a higher control phase.

Figure 21A:
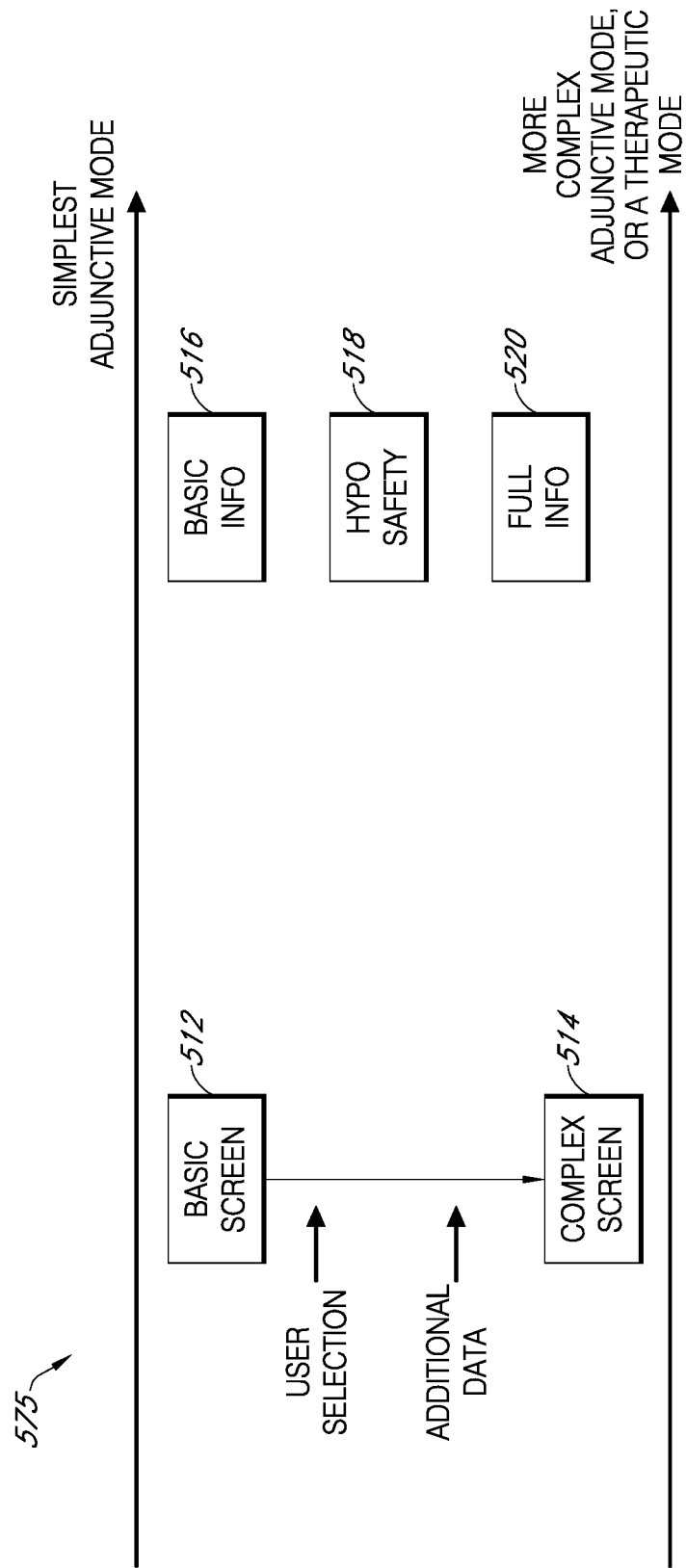
FIG. 21A is a diagram depicting ways to display adjunctive (non-therapeutic) mode data and FIG. 21B is a flowchart according to present principles showing another implementation of a method of mode switching, in particular depicting transitions to higher-calibration-required modes caused by user requests for additional or different data.
Figure 21B:
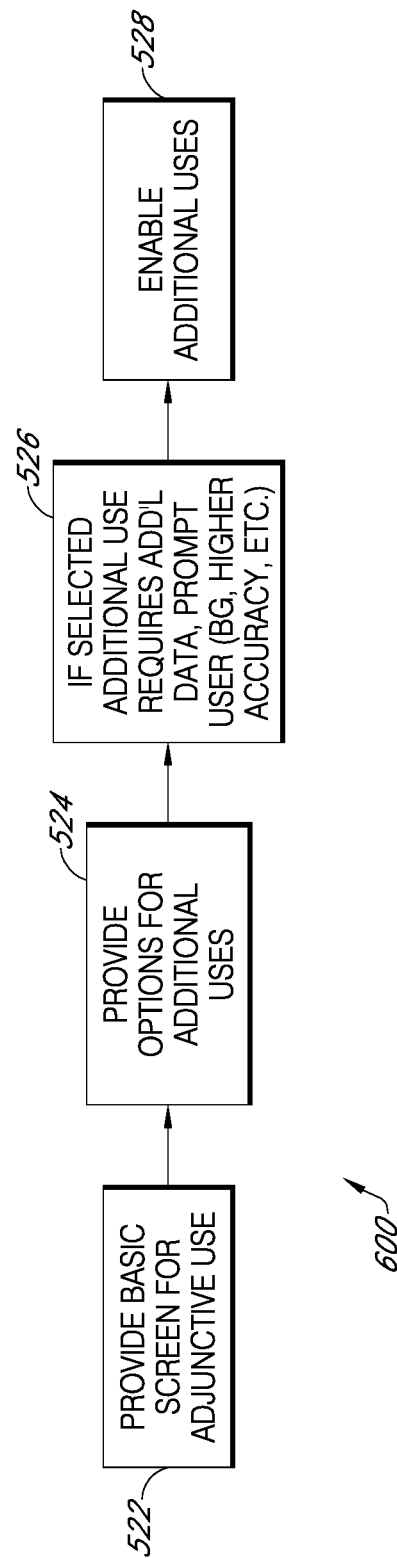

In another specific example, as shown by the diagram 575 of FIG. 21A and the flowchart 600 of FIG. 21B, adjunctive and therapeutic modes may be operated in parallel, simultaneously, or concurrently, where a basic screen 512 is provided that shows low-resolution data, e.g., trends, arrows, and/or ranges. Such data may be sufficient for adjunctive use and require little or no calibration. The user can then select other screens via a menu, and in some cases such other screens such as a complex screen 514 will provide an alert or alarm to the user that additional and higher levels of data usability, e.g., calibration or accuracy, are required, in which case the more complex or therapeutic modes (running in parallel, simultaneously, or concurrently) may be switched to if the usability of the data allows.

There could be different levels of information provided by the screens, which, when selected, would trigger different requirements/criteria in different submodes, based on what the user wants to see or do. For example, a basic information screen 516 may provide a simple arrow indicating rate of change as well as a glycemic range. A hypoglycemia safety screen 518 may be provided that alarms on hypoglycemia only. Such a screen may require some degree of calibration, including potentially user-dependent calibration. A full management information screen 520 may also be provided, which alerts and alarms for high and low values as well as high or low rates of change. This type of screen display may require even more signal usability than the previously described screens (which may require more or greater calibration in some circumstances). If the required levels of data resolution become high enough, the mode may switch to another mode, as noted above, e.g., the mode may switch to the therapeutic mode if the user has indicated a desire for such a switch. This system allows flexibility in mode switching—the user is enabled to view a high resolution mode but is not required to do so and in fact can employ a simple UI even with data that is innately of high resolution. The parallel modes, which as noted may run concurrently or simultaneously, need not run concurrently or simultaneously for an entire duration of a session. But while they are running in parallel, modes may be easily switched from one to another. Of course, when they are not running in parallel, the modes may be switched using any of the other methods described herein, e.g., with respect to FIG. 1, 3A, 3B, 4, 9-15A, 15C, 17, or 20.

As seen in the flowchart 600, in a first step a basic screen may be provided on the user interface of the monitoring device for adjunctive use (step 522). Options may then be provided for additional uses (step 524), where such options are provided on the user interface of the monitoring device.

If the user selects an information screen which requires additional information (step 526), the monitoring device may either automatically switch to a mode in which sufficient calibration or other data are received to enable the additional information, or the user may be prompted before such modes are entered. Once such data is received by the monitoring device, the additional uses may be enabled (step 528), and the screen with additional information displayed.

Figure 22:
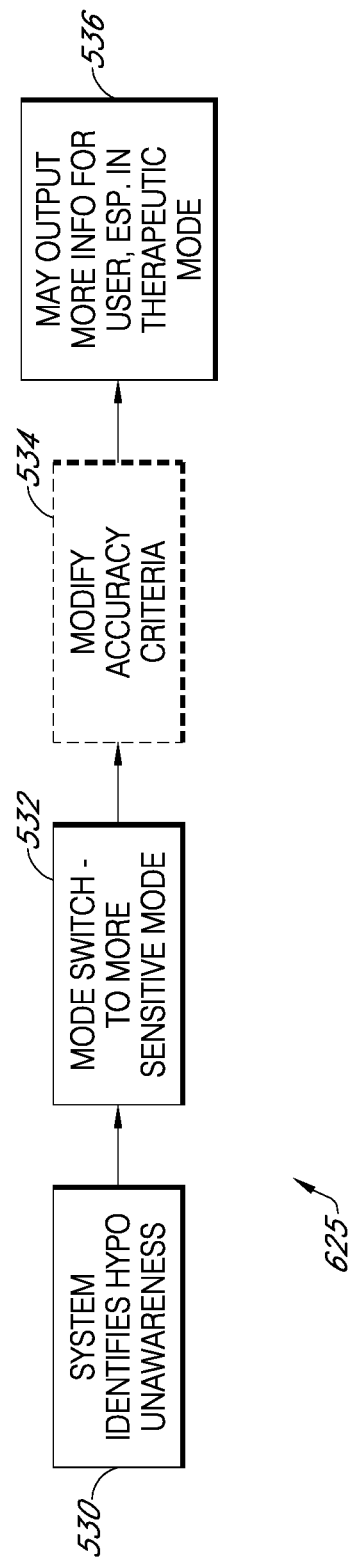
FIG. 22 is a flowchart according to present principles showing another implementation of a method of mode switching, in particular identifying and treating hypoglycemia unawareness.

In another specific example, as shown by the flowchart 625 of FIG. 22, the monitoring device may identify hypoglycemia unawareness in a user (step 530), such as by a lack of correlation between a user feeling low and CGM data actually being low. In this case, a mode switch may occur to a mode that is more sensitive (step 532). In an optional step, accuracy criteria may also be modified (step 534). As a result of the mode switch, the monitoring device may output and display more information for the user (step 536), especially where the device is in therapeutic mode. The additional information may further educate the user as to how to identify hypoglycemia, how to treat the same, and the ramifications of the hypoglycemic state.

Overview/General Description of System

The glucose sensor can use any system or method to provide a data stream indicative of the concentration of glucose in a host. The data stream is typically a raw data signal that is transformed to provide a useful value of glucose to a user, such as a patient or doctor, who may be using the sensor. Faults may occur, however, which may be detectable by analysis of the signal, analysis of the clinical context, or both. Such faults require discrimination to distinguish the same from actual measured signal behavior, as well as for responsive signal processing, which can vary according to the fault. Accordingly, appropriate fault discrimination and responsive processing techniques are employed.

Glucose Sensor

The glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor capable of measuring the concentration of glucose in a host, the systems and methods of embodiments can be applied to any measurable analyte, a non-exhaustive list of appropriate analytes noted above. Some exemplary embodiments described below utilize an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. patent application Ser. No. 11/543,396 filed Oct. 4, 2006, co-pending U.S. patent application Ser. No. 11/691,426 filed on Mar. 26, 2007, and co-pending U.S. patent application Ser. No. 11/675,063 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

Various sensors may be employed. In the case of continuous glucose sensing, it is contemplated that the sensing region may include any of a variety of electrode configurations. For example, in some embodiments, in addition to one or more glucose-measuring working electrodes, the sensing region may also include a reference electrode or other electrodes associated with the working electrode. In these particular embodiments, the sensing region may also include a separate reference or counter electrode associated with one or more optional auxiliary working electrodes. In other embodiments, the sensing region may include a glucose-measuring working electrode, an auxiliary working electrode, two counter electrodes (one for each working electrode), and one shared reference electrode. In yet other embodiments, the sensing region may include a glucose-measuring working electrode, an auxiliary working electrode, two reference electrodes, and one shared counter electrode.

U.S. Patent Publication No. US-2008-0119703-A1 and U.S. Patent Publication No. US-2005-0245799-A1 describe additional configurations for using the continuous sensor in different body locations. In some embodiments, the sensor is configured for transcutaneous implantation in the host. In alternative embodiments, the sensor is configured for insertion into the circulatory system, such as a peripheral vein or artery. However, in other embodiments, the sensor is configured for insertion into the central circulatory system, such as but not limited to the vena cava. In still other embodiments, the sensor can be placed in an extracorporeal circulation system, such as but not limited to an intravascular access device providing extracorporeal access to a blood vessel, an intravenous fluid infusion system, an extracorporeal blood chemistry analysis device, a dialysis machine, a heart-lung machine (i.e., a device used to provide blood circulation and oxygenation while the heart is stopped during heart surgery), etc. In still other embodiments, the sensor can be configured to be wholly implantable, as described in U.S. Pat. No. 6,001,067.

Figure 23:
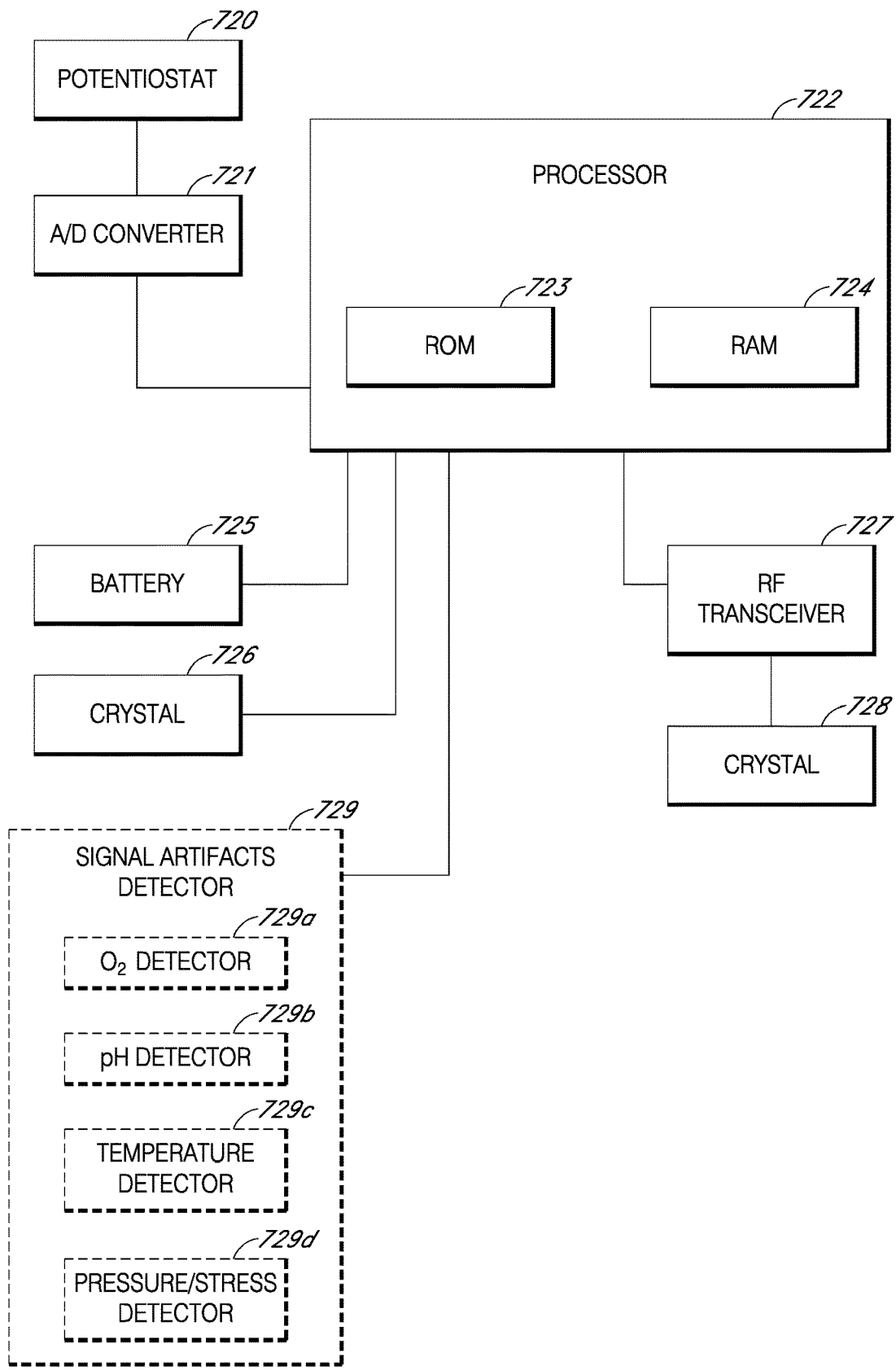
FIG. 23 is a block diagram that illustrates sensor electronics in one embodiment.

FIG. 23 is a block diagram that illustrates one possible configuration of the sensor electronics in one embodiment. In this embodiment, a potentiostat 720 is shown, which is operatively connected to an electrode system and provides a voltage to the electrodes, which biases the sensor to enable measurement of a current value indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device. In the illustrated embodiment, an A/D converter 721 digitizes the analog signal into "counts" for processing. Accordingly, the resulting raw data stream in counts is directly related to the current measured by the potentiostat 720.

A processor module 722 is the central control unit that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in more detail elsewhere herein). The processor additionally can be used for the system's cache memory, for example for temporarily storing recent sensor data. In some embodiments, the processor module comprises memory storage components such as various types of ROM, RAM, flash memory, and the like. In one exemplary embodiment, ROM 723 provides semi-permanent storage of data, for example, storing data such as sensor identifier (ID) and programming to process data streams (e.g., programming for signal artifacts detection and/or replacement such as described elsewhere herein). In one exemplary embodiment, RAM 724 can be used for the system's cache memory, for example for temporarily storing recent sensor data.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor ID code, raw data, filtered data, and/or error detection or correction. The processor module can be configured to transmit any combination of raw and/or filtered data.

A battery 725 is operatively connected to the processor 722 and provides the necessary power for the sensor (e.g., 800). In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. In yet other embodiments, the receiver can be transcutaneously powered via an inductive coupling, for example. A Quartz Crystal 726 is operatively connected to the processor 22 and maintains system time for the computer system as a whole.

An RF module, (e.g., an RF Transceiver) 727 is operably connected to the processor 722 and transmits the sensor data from the sensor (e.g., 800) to a receiver (see FIGS. 27 and 28). Although an RF transceiver is shown here, some other embodiments can include a wired rather than wireless connection to the receiver. A second quartz crystal 728 provides the system time for synchronizing the data transmissions from the RF transceiver. It is noted that the transceiver 727 can be substituted with a transmitter in other embodiments. In some alternative embodiments, however, other mechanisms, such as optical, infrared radiation (IR), ultrasonic, and the like, can be used to transmit and/or receive data.

In some embodiments, a Signal Artifacts Detector 729 is provided that includes one or more of the following: an oxygen detector 729a, a pH detector 729b, a temperature detector 729c, and a pressure/stress detector 729d, which is described in more detail with reference to signal artifacts and faults/errors detection and discrimination. It is noted that in some embodiments the signal artifacts detector 729 is a separate entity (e.g., temperature detector) operatively connected to the processor, while in other embodiments, the signal artifacts detector is a part of the processor and utilizes readings from the electrodes, for example, to detect signal faults and artifacts. Although the above description includes some embodiments in which all discrimination occurs within the sensor, other embodiments provide for systems and methods for detecting signal faults in the sensor and/or receiver electronics (e.g., processor module) as described in more detail elsewhere herein.

Receiver

Figure 24:
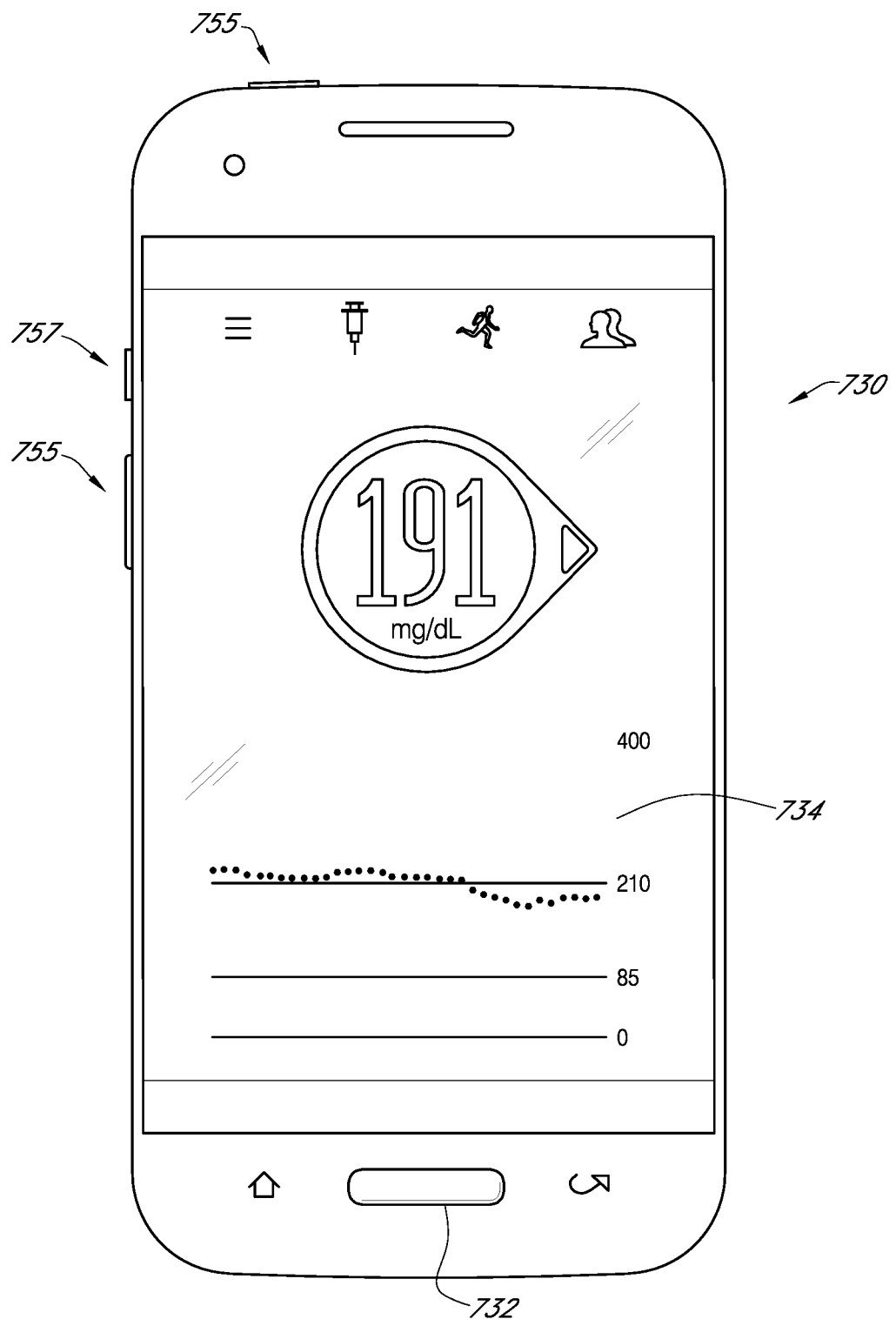
FIG. 24 is a schematic view of a receiver in one implementation.

FIG. 24 is a schematic view of a receiver 730 including a representation of an estimated glucose value on its user interface. The receiver 730 includes systems to receive, process, and display sensor data from the glucose sensor (e.g., 800), such as described herein. Particularly, the receiver 730 can be a mobile phone type device, for example, and comprise a user interface that has a physical button 732 and a display screen 734, as well as one or more input/output (I/O) devices, such as a touch screen, one or more buttons 755 and/or switches 757, which when activated or clicked perform one or more functions. In FIG. 24, the UI also shows historical trend data, as well as a compass-type icon element surrounding the glucose concentration value indicating a rate-of-change trend. Various other features are shown, including UI icons which may be employed to enter medicament information, e.g., insulin boluses, exercise data, and to provide social networking functionality.

In the illustrated embodiment, the electronic device is a smartphone, and the display 734 comprises a touchscreen, which also functions as an I/O device. In some embodiments, the user interface can also include a keyboard, a speaker, and a vibrator. The functions of the receiver or smart phone can also be implemented as functions within an application running on a tablet computer, or like device. In other embodiments, the receiver may comprise a device or devices other than a smartphone, such as a smartwatch, a tablet computer, a mini-tablet computer, a handheld personal digital assistant (PDA), a game console, a multimedia player, a wearable device, such as those described above, a screen in an automobile or other vehicle, a dedicated receiver device, etc. The receiver may also be a medicament administration device such as an insulin pump.

In some embodiments, the user will be able to interactively select the type of output displayed on their user interface. In other embodiments, the sensor output can have alternative configurations. In yet other embodiments, the type of output displayed on the user interface will display on the mode switched to, e.g., indicating an operating mode, a type of user interaction, data appropriate thereto, and/or the like.

Figure 25:
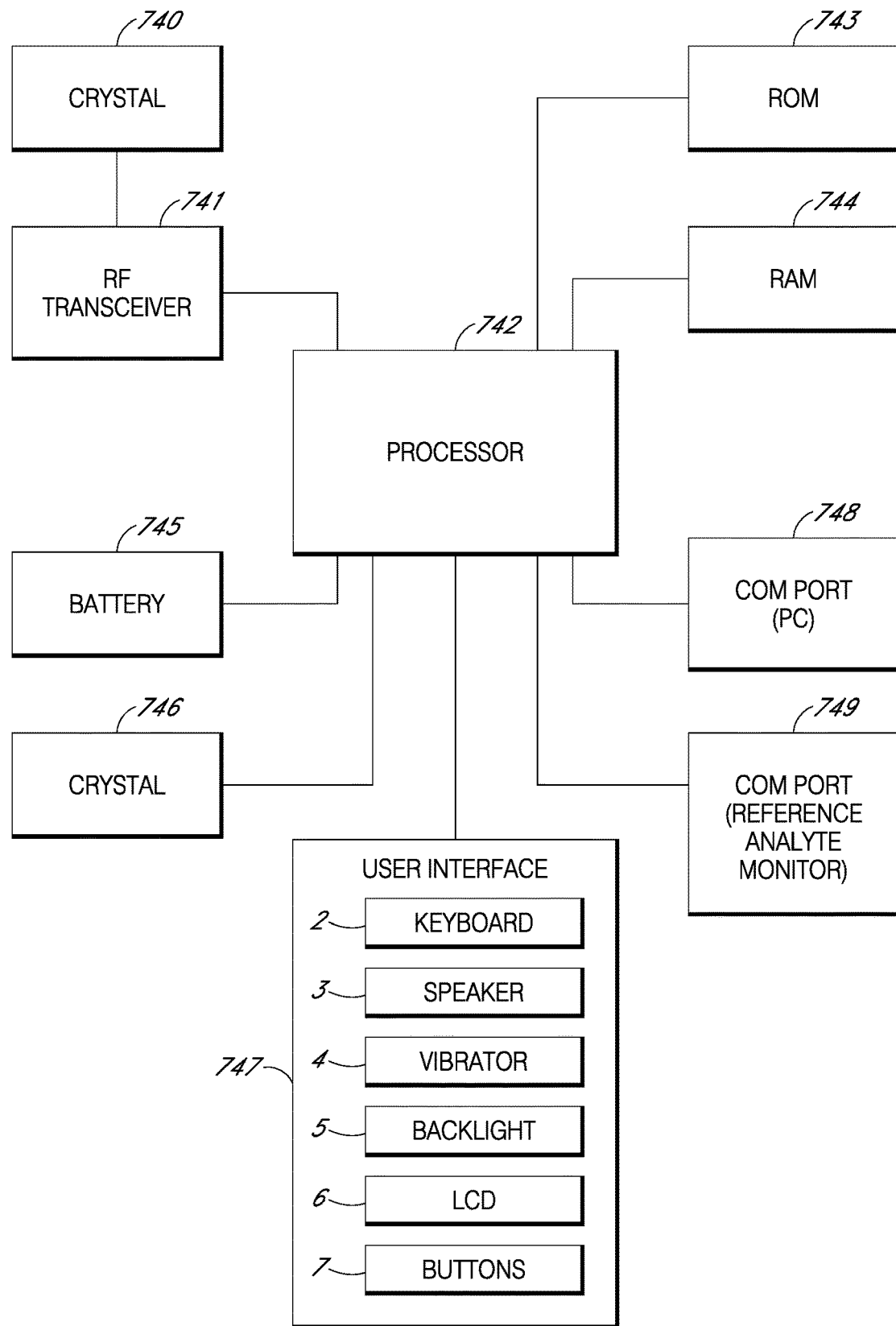
FIG. 25 is a block diagram of receiver electronics in one embodiment.

FIG. 25 is a block diagram that illustrates one possible configuration of the receiver, e.g., a smart phone, electronics. It is noted that the receiver can comprise a configuration such as described with reference to FIG. 24, above. Alternatively, the receiver can comprise other configurations, including a desktop computer, laptop computer, a personal digital assistant (PDA), a server (local or remote to the receiver), and the like. In some embodiments, the receiver can be adapted to connect (via wired or wireless connection) to a desktop computer, laptop computer, PDA, server (local or remote to the receiver), and the like, in order to download data from the receiver. In some alternative embodiments, the receiver and/or receiver electronics can be housed within or directly connected to the sensor (e.g., 800) in a manner that allows sensor and receiver electronics to work directly together and/or share data processing resources. Accordingly, the receiver's electronics (or any combination of sensor and/or receiver electronics) can be generally referred to as a "computer system."

A quartz crystal 740 is operatively connected to an RF transceiver 741 that together function to receive and synchronize data streams (e.g., raw data streams transmitted from the RF transceiver). Once received, a processor 742 processes the signals, such as described below.

The processor 742, also referred to as the processor module, is the central control unit that performs the processing, such as comparing determined data against criteria to determine if mode switching should occur, storing data, analyzing data streams, calibrating analyte sensor data, predicting analyte values, comparing predicted analyte values with corresponding measured analyte values, analyzing a variation of predicted analyte values, downloading data, and controlling the user interface by providing analyte values, prompts, messages, warnings, alarms, and the like. The processor includes hardware and software that performs the processing described herein, for example flash memory provides permanent or semi-permanent storage of data, storing data such as sensor ID, receiver ID, and programming to process data streams (for example, programming for performing prediction and other algorithms described elsewhere herein) and random access memory (RAM) stores the system's cache memory and is helpful in data processing.

In one exemplary embodiment, the processor is a microprocessor that provides the processing, such as calibration algorithms stored within a ROM 743. The ROM 743 is operatively connected to the processor 742 and provides semi-permanent storage of data, storing data such as receiver ID and programming to process data streams (e.g., programming for performing calibration and other algorithms described elsewhere herein). In this exemplary embodiment, a RAM 744 is used for the system's cache memory and is helpful in data processing.

A battery 745 is operatively connected to the processor 742 and provides power for the receiver. In one embodiment, the battery is a standard AAA alkaline battery, however any appropriately sized and powered battery can be used. In some embodiments, a plurality of batteries can be used to power the system. A quartz crystal 746 is operatively connected to the processor 742 and maintains system time for the computer system as a whole.

A user interface 747 comprises a keyboard 2, speaker 3, vibrator 4, backlight 5, liquid crystal display (LCD 6), and one or more buttons 7, which may be implemented as physical buttons or buttons on a touchscreen interface. The components that comprise the user interface 47 provide controls to interact with the user. The keyboard 2 can allow, for example, input of user information about himself/herself, such as mealtime, exercise, insulin administration, and reference glucose values. The speaker 3 can provide, for example, audible signals or alerts for conditions such as present and/or predicted hyper- and hypoglycemic conditions. The vibrator 4 can provide, for example, tactile signals or alerts for reasons such as described with reference to the speaker, above. The backlight 5 can be provided, for example, to aid the user in reading the LCD in low light conditions. The LCD 6 can be provided, for example, to provide the user with visual data output such as is illustrated in FIG. 24. The buttons 7 can provide for toggle, menu selection, option selection, mode selection, and reset, for example.

In some embodiments, prompts or messages can be displayed on the user interface to convey information to the user, such as requests for reference analyte values, therapy recommendations, deviation of the measured analyte values from the predicted analyte values, and the like. Additionally, prompts can be displayed to guide the user through calibration or trouble-shooting of the calibration.

In some implementations, the continuous analyte sensor system includes a Dexcom G4® Platinum glucose sensor and transmitter commercially available from Dexcom, Inc., for continuously monitoring a host's glucose levels.

In some embodiments, the system may execute various applications, for example, a CGM application, which may be downloaded to the receiver or other electronic device over the Internet and/or a cellular network, and the like. Data for various applications may be shared between the device and one or more other devices/systems, and stored by cloud or network storage and/or on one or more other devices/systems.

What has been disclosed are systems and methods for dynamically and iteratively changing or switching modes and/or submodes of a monitoring device based on determined data, generally compared against a trigger such as one or more transition criteria. A variety of methods have been disclosed for determining when and how to switch modes, as well as a number of potential types of data and criteria.

Variations will be understood to one of ordinary skill in the art given this teaching. For example, while multimodal transitions have been described, it will be understood that such may include multiple transition criteria from one category or multiple transition criteria drawn from multiple categories, e.g., from multiple of flowcharts from FIGS. 5-9.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer-readable medium may comprise non-transitory computer-readable medium (e.g., tangible media). In addition, in some aspects a computer-readable medium may comprise transitory computer-readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained. For example, a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

The system and method may be fully implemented in any number of computing devices. Typically, instructions are laid out on computer-readable media, generally non-transitory, and these instructions are sufficient to allow a processor in the computing device to implement the method of the invention. The computer-readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file-storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi-connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where mode switching is contemplated, the plural inputs may allow plural users or devices to input relevant data and criteria at the same time.

Various methods and devices are provided.

In Method 1, provided is a method of operating a continuous glucose monitoring device, the continuous glucose monitoring device coupled to a glucose sensor and operating in an initial mode of operation, comprising: measuring a signal indicative of glucose concentration data; displaying the glucose concentration data on a user interface of the continuous glucose monitoring device, the user interface in the initial mode of operation having an initial mode of user interaction; determining data indicative of a usability of the continuous glucose monitoring device; comparing the determined data to one or more transition criteria; if the comparing indicates the determined data has met or will meet the transition criteria, causing the continuous glucose monitoring device to transition to a new mode of operation; and displaying the glucose concentration data on the user interface of the continuous glucose monitoring device, the user interface in the new mode of operation having a different mode of user interaction than the initial mode, such that the continuous glucose monitoring device operates in a mode of user interaction according to the device usability.

In Method 2, which is a variant of Method 1, the displaying is based at least in part on the mode of operation.

In Method 3, which is a variant of Method 1 or 2, the determining data includes receiving data from the sensor.

In Method 4, which is a variant of Method 3, the receiving data from the sensor includes receiving data from a sensor electronics module coupled to the sensor.

In Method 5, which is a variant of any one of the above Methods, the sensor is configured for in vivo insertion into the patient.

In Method 6, which is a variant of any one of the above Methods, a first output of the monitoring device in the initial mode of operation represents the initial mode of user interaction and a second output of the monitoring device in the new mode of operation represents the new mode of user interaction, and wherein the first and second outputs are different.

In Method 7, which is a variant of Method 6, the initial and new modes of user interaction are configured such that the new mode of user interaction requires less user interaction than the initial mode of user interaction.

In Method 8, which is a variant of Method 8, the initial and new modes of user interaction are selected from the group consisting of: user-dependent calibration and device self-calibration.

In Method 9, which is a variant of Method 8, the analyte is glucose and wherein the user-dependent calibration corresponds to entry of a calibration value from an external blood glucose meter.

In Method 10, which is a variant of Method 6, the initial and new modes of user interaction include levels of confirmation interactions.

In Method 11, which is a variant of Method 6, the analyte is glucose and wherein the initial and new modes of user interaction include different levels of control in an artificial pancreas system.

In Method 12, which is a variant of Method 6, the analyte is glucose and wherein the initial and new modes of user interaction are data transmission modes selected from the group consisting of: on-demand data transmission and device-initiated data transmission.

In Method 13, which is a variant of Method 6, the initial and new modes of user interaction are selected from the group consisting of: pushed data or pulled data.

In Method 14, which is a variant of Method 4, which is a variant of any one of the above Methods, the determined data includes an analyte concentration value and/or a time rate of change thereof.

In Method 15, which is a variant of any one of the above Methods, the determined data indicative of the usability of the device and the transition criteria include one or more parameters indicative of the usability of a signal from the sensor.

In Method 16, which is a variant of Method 15, the one or more parameters related to the usability of the signal corresponds to one or more parameters selected from the group consisting of: accuracy, reliability, stability, confidence, and/or glycemic urgency index.

In Method 17, which is a variant of Method 15 or 16, the one or more parameters related to the usability of the signal correspond to a level of noise or to one or more faults detected in the signal, and wherein the transition criteria is a threshold level of noise or a predetermined type or level of fault.

In Method 18, which is a variant of Method 17, the level of noise or the one or more faults detected in the signal are determined based on a long-term trend of the signal, a short-term trend of the signal, or on a history of a user's previous sensor session.

In Method 19, which is a variant of Method 15 or 16, the one or more parameters related to the usability of the signal correspond to one or more of the group consisting of: signal value, a range of signal values, or a time rate of change thereof; analyte concentration value or range of values; calibration data; a measured error at calibration; data from self-diagnostics or calibration diagnostics; metadata about sensor identity; environmental data corresponding to a sensor; historical pattern data; external data; data about frequency of calibration; biological data about sensor placement; a time duration since sensor implantation; an impedance associated with the signal; a received user response to a prompt displayed on a user interface; a decision support mode; a data transmission mode; data about a selected use of the monitoring device; data about clinical or user goals; or combinations of the above.

In Method 20, which is a variant of Method 19, the environmental data corresponds to altitude or temperature data about a sensor environment.

In Method 21, which is a variant of Method 19, the calibration data is selected from the group consisting of: calibration values, confidence in calibration values, uncertainty in calibration values, range of calibration values, rate of change of calibration values, current calibration values compared to historical calibration values, stability in calibration values, whether calibration values match expected or predicted values, confidence in a user's ability to accurately enter calibration values from a meter, whether entered calibration data corresponds to a default or pre-entered value, or combinations of the above.

In Method 22, which is a variant of Method 19, the historical pattern data includes data about rebound variability.

In Method 23, which is a variant of Method 19, the external data is from an activity monitor, a sleep monitor, a medicament pump, GPS device, a redundant analyte sensor, or a smart pen, or combinations of the above.

In Method 24, which is a variant of Method 19, the biological data about sensor placement corresponds to data about: tissue type, wound response, diffusion distance, or combinations of the above.

In Method 25, which is a variant of Method 24, the diffusion distance is proportional to one or more selected from the group consisting of: impedance, thickness of membrane over electrode array, oxygen depletion rate, or diffusion of specific species between electrodes, or combinations of the above.

In Method 26, which is a variant of Method 19, the decision support mode is selected from different levels of control of an artificial pancreas system.

In Method 27, which is a variant of Method 19, the data about a selected use of the monitoring device includes data about uses selected from the group consisting of: weight loss monitoring, monitoring exercise or activity impact on glucose, post-meal glucose summary, food selection, effect of the monitored analyte on illness or menstrual cycle or pregnancy, user preference or convenience, or combinations of the above.

In Method 28, which is a variant of Method 19, the data about clinical or user goals includes: data about user knowledge of device, desired accuracy of device, desired convenience of device, use of device for hypoglycemic avoidance, use of device for nighttime control, use of device for postprandial control, qualitative or quantitative desired duration of sensor session, or combinations of the above.

In Method 29, which is a variant of Method 28, the desired convenience of the device corresponds to a number of required external meter calibration values.

In Method 30, which is a variant of Method 4, which is a variant of any one of the above Methods, the initial mode is user-dependent calibration, and before the causing step, causing the device to periodically and temporarily enter a self-calibration mode, to interrogate the sensor and to examine a transient response, followed by a re-entering of the user-dependent calibration initial mode.

The method of any one of the above claims, the Method further comprises displaying output data based on the new mode.

In Method 32, which is a variant of Method 31, the Method further comprises displaying an indication of an expected duration of the new mode.

In Method 33, which is a variant of Method 31, the Method further comprises displaying an indication of sensor performance.

In Method 34, which is a variant of Method 1-9, the initial mode is user-dependent calibration and the new mode is device self-calibration; or wherein the initial mode is device self-calibration and the new mode is user-dependent calibration.

In Method 35, which is a variant of Method 34, the determined data is sensor signal or data usability and the transition criteria is a threshold level of sensor signal or data usability.

In Method 36, which is a variant of Method 35, the transition criteria is further dependent on a decision support mode, wherein the decision support mode is selected from the group consisting of adjunctive, therapeutic, or a phase or mode of control in an artificial pancreas system.

In Method 37, which is a variant of Method 35, the transition criteria is further dependent on data entered or received about a user or clinician use of information displayed by the monitoring device.

In Method 38, which is a variant of Method 36, a decision support mode associated with the initial mode is therapeutic and a decision support mode associated with the new mode is adjunctive, and wherein the determined data is such that the sensor signal usability decreased below the threshold level of sensor signal usability associated with the transition criterion.

In Method 39, which is a variant of Method 38, comprising: prompting a user on a periodic basis to enter a calibration value from an external meter for blood glucose; and receiving the calibration value for blood glucose.

In Method 40, which is a variant of Method 39, the periodicity is less in the new mode than in the initial mode.

In Method 41, which is a variant of Method 36, a decision support mode associated with the initial mode is adjunctive and a decision support mode associated with the new mode is therapeutic, and wherein the determined data is such that the sensor signal usability increased above the threshold level of sensor signal usability associated with the transition criterion.

In Method 42, which is a variant of Method 41, the Method further comprises prompting a user on a periodic basis to enter a calibration value for blood glucose; and receiving the calibration value for blood glucose.

In Method 43, which is a variant of Method 42, the periodicity is greater in the new mode than in the initial mode.

In Method 44, which is a variant of Method 1-9, the Method further comprises determining an intended mode of the monitoring device.

In Method 45, which is a variant of Method 44, the determining includes detecting whether a medicament delivery device is coupled to the monitoring device, and if so, configuring the monitoring device to a mode that is therapeutic.

In Method 46, which is a variant of Method 44, the determining includes: prompting a user to indicate an intended use of the monitoring device; receiving the indication; and configuring the monitoring device to a mode associated with the received indication.

In Method 47, which is a variant of Method 46, a number of blood glucose calibration readings required of the user is based on the configured mode.

In Method 48, which is a variant of Method 46, the intended use is therapeutic, and configuring the monitoring device to a user-dependent calibration mode.

In Method 49, which is a variant of Method 46, the intended use is adjunctive, and configuring the monitoring device to a device self-calibration mode.

In Method 50, which is a variant of Method 1-9, the initial mode is device self-calibration and the new mode is user-dependent calibration, and further comprising: prompting a user to enter a calibration value for blood glucose; receiving the calibration value for blood glucose; and using the received calibration value to inform the device self-calibration.

In Method 51, which is a variant of Method 50, the received calibration value informs the device self-calibration by modifying the device self-calibration.

In Method 52, which is a variant of Method 1-9, the initial mode is device self-calibration and the new mode is user-dependent calibration, and wherein the determined data and the transition criteria include one or more parameters related to the usability of a signal from the sensor, and wherein the one or more parameters are selected from the group consisting of: data from diagnostic routines indicating a shift in sensitivity; data entered by a user about a perceived error; data from a connected device; data from historic analyte values; time of day; day of week; whether a glucose value is high or low as compared to respective thresholds; glucose urgency index; data about glucose concentration value variability; data about a level of user responsiveness; sensor signal value trajectory pre- and post-insertion of a new sensor; redundant or overlapping sensor data; user feedback on alerts and alarms; meal or exercise data as compared to predicted signal responses to meal or exercise data; data about a decision support mode configured for the monitoring device; or combinations of the above.

In Method 53, which is a variant of Method 52, the data from diagnostic routines includes impedance data detecting shifts in sensitivity.

In Method 54, which is a variant of Method 52, the diagnostic routines are performed on a periodic basis or upon detection of an error.

In Method 55, which is a variant of Method 52, the data entered by a user about a perceived error includes a blood glucose calibration value entered by a user in the absence of a prompt from the monitoring device, or a detection of a greater than average number of blood glucose calibration values entered by a user.

In Method 56, which is a variant of Method 52, the data from a connected device includes data from an external blood glucose meter.

In Method 57, which is a variant of Method 1-9, the initial mode is device self-calibration and the new mode is user-dependent calibration, and further comprising: if the comparing indicates the determined data has met or will meet the transition criteria, then before the causing step, prompting a user to enter a reason for the determined data; receiving the reason for the determined data; and based on the received reason, causing the monitoring device to maintain the initial mode of operation.

In Method 58, which is a variant of Method 57, the reason is a user-perceived outlier, a user-perceived false alarm, or meal or exercise data.

In Method 59, which is a variant of Method 58, the Method further comprises comparing the entered meal or exercise data to prior user-entered meal or exercise data, and comparing a current signal to a signal associated with the prior user-entered meal or exercise data, and determining if the current signal and entered meal or exercise data are consistent with the prior signal and prior meal or exercise data.

In Method 60, which is a variant of Method 1-9, the initial mode is device self-calibration and the new mode is user-dependent calibration, and further comprising: determining if a number of blood glucose measurements taken and entered into the monitoring device as calibration values exceed a predetermined threshold over a predetermined period of time; and if so, causing the monitoring device to transition to a user-dependent calibration mode.

In Method 61, which is a variant of Method 1-9, the initial mode is user-dependent and the new mode is device self-calibration, and wherein the transition criteria corresponds to a level of confidence in the device self-calibration, and further comprising: prompting a user to enter a calibration value for blood glucose, and using the entered value as the determined data; and if the comparing indicates the determined data meets the transition criteria, then performing the causing step.

In Method 62, which is a variant of Method 1-9, the initial mode is user-dependent calibration and the new mode is device self-calibration, and wherein the determined data and the transition criteria correspond to usability of entered blood glucose data.

In Method 63, which is a variant of Method 62, the usability of entered blood glucose data corresponds to an accuracy, reliability, stability, or confidence in the blood glucose data.

In Method 64, which is a variant of Method 63, the Method further comprises confirming that entered blood glucose data is within a particular confidence interval or stability criterion, and if it is not, then performing the causing step.

In Method 65, which is a variant of Method 63, the Method further comprises confirming that entered blood glucose data is within an expected range based on an a priori or internal calibration, and if it is not, then performing the causing step.

In Method 66, which is a variant of Method 62, the transition criteria is based at least in part on a decision support mode in which the device is configured.

In Method 67, which is a variant of Method 62, the determined data and the transition criteria indicate that the device continues to require external reference data for calibration, and further comprising maintaining the initial mode.

In Method 68, which is a variant of Method 62, the determined data and the transition criteria indicate that the device no longer requires external reference data for calibration, and further comprising performing the causing step.

In Method 69, which is a variant of Method 62, the Method further comprises a package of sensors manufactured from the same lot, and wherein the sensor is a first of a plurality of sensors in the pack, and wherein the determined data and the transition criteria indicate that the device no longer requires external reference data for calibration, and further comprising: performing the causing step of causing the monitoring device to transition to a new mode of operation; and for subsequent sensors in the pack, initializing the device in device self-calibration mode, using one or more calibration settings associated with the first sensor.

In Method 70, which is a variant of Method 1-9, the Method further comprises initializing the monitoring device in two modes simultaneously, a first mode being user-dependent calibration and a second mode being device self-calibration; receiving and comparing two glucose concentration values, one glucose concentration value from the first mode and another glucose concentration value from the second mode; determining and displaying a glucose concentration value based on the two glucose concentration values; determining a level of confidence in the glucose concentration value from the second mode, using at least the two glucose concentration values; and once the determined level of confidence in the glucose concentration value from the second mode reaches a predetermined threshold, then only displaying the glucose concentration value from the second mode.

In Method 71, which is a variant of Method 70, the determining a level of confidence in the glucose concentration value from the second mode includes comparing at least the glucose concentration value from the second mode to a calibration value from an external meter.

In Method 72, which is a variant of Method 70, the Method further comprises detecting a fault, and upon detection of the fault, displaying the glucose concentration value according to the first mode.

In Method 73, which is a variant of Method 70, the comparing includes comparing results of diagnostic tests or internal calibration information.

In Method 74, which is a variant of Method 73, the internal calibration information is based on an impedance measurement.

In Method 75, which is a variant of Method 70, the predetermined threshold is based at least in part on a decision support mode in which the device is configured.

In Method 76, which is a variant of Method 70, the comparing includes comparing slope and baseline information for the two modes.

In Method 77, which is a variant of Method 76, the comparing further comprises: comparing errors in slope and baseline data for each of the two modes; and once the error in the slope or baseline for the second mode is equivalent to that in the first mode, then only displaying the glucose concentration value from the second mode.

In Method 78, which is a variant of Method 70, the comparing further comprises determining slope and baseline information for each of the two modes with respective slope and baseline information for each of the two modes from a prior session.

In Method 79, which is a variant of Method 70, the Method further comprises displaying an indication of when a calibration value from an external meter is required.

In Method 80, which is a variant of Method 1-7 or 9, the Method further comprises initializing the monitoring device in two parallel modes, a first mode being user-dependent calibration and a second mode being device self-calibration; receiving and comparing two glucose concentration values, one glucose concentration value from the first mode and another glucose concentration value from the second mode; providing a weighting of the two glucose concentration values; and displaying a glucose concentration value according to the weighted glucose concentration values.

In Method 81, which is a variant of Method 80, the weighting is proportional to the usability of the data determined by each of the modes.

In Method 82, which is a variant of Method 81, once the weighting for a given mode reaches a predetermined threshold, the glucose concentration value displayed is determined based on only the given mode.

In Method 83, which is a variant of Method 1-7 or 11, the determined data corresponds to a sensor signal, and wherein the transition criteria corresponds at least to a usability of the sensor signal.

In Method 84, which is a variant of Method 83, the transition criteria is at least in part based on the initial mode of operation.

In Method 85, which is a variant of Method 1-7 or 11, the initial mode is a therapeutic mode, and the new mode is an adjunctive mode.

In Method 86, which is a variant of Method 85, the displaying in the new mode of operation further comprises, while in the adjunctive mode, displaying data to a user in such a way as to indicate its usability adjunctively.

In Method 87, which is a variant of Method 86, the displaying in the new mode of operation further comprises indicating the usability of the data by displaying a zone or range of glycemic data instead of a single value.

In Method 88, which is a variant of Method 86, the displaying in the new mode of operation further comprises requiring the user to clear a prompt before displaying a subsequent glucose concentration value or range of glucose concentration values.

In Method 89, which is a variant of Method 86, the usability is indicated by colors and/or flashing numerals and/or a dot size on a trend graph.

In Method 90, which is a variant of Method 86, the displaying in the new mode of operation further comprises restricting displayed data to only a rate of change arrow and not a glucose concentration value.

In Method 91, which is a variant of Method 86, the usability is indicated by a displayed change in a prediction horizon.

In Method 92, which is a variant of Method 85, the displaying in the new mode of operation further comprises, while in the therapeutic mode, displaying data to a user in such a way as to indicate its usability therapeutically.

In Method 93, which is a variant of Method 92, the displaying in the new mode of operation further comprises indicating the usability of the data by displaying a determined single value of glucose concentration.

In Method 94, which is a variant of Method 92, the usability is indicated by a displayed change in a prediction horizon.

In Method 95, which is a variant of Method 92, the usability is indicated by colors and/or flashing numerals and/or a dot size on a trend graph.

In Method 96, which is a variant of Method 1-7 or 11, the transition criteria is further at least partially based on time of day or day of week.

In Method 97, which is a variant of Method 83, the usability of the sensor signal is based on one or more parameters according to one or more of Methods 16, 17, 19, 21, 28, or 52.

In Method 98, which is a variant of Method 83, the usability of the sensor signal is based on one or more parameters selected from the group consisting of: a user response to a query about a perceived accuracy or perceived user glucose range; data about likelihood of a potential fault or failure mode; data about glucose context; a user response to a query about a glycemic event; a user response to a query about a potential false alarm; a confirmatory meter reading requested of a user via a displayed prompt; a calibration mode; a data transmission mode; a user indication of desired monitoring device responsiveness; or combinations of the above.

In Method 99, which is a variant of Method 83, the Method further comprises changing a calibration mode along with the change from the initial to the new mode of operation.

In Method 100, which is a variant of Method 83, the Method further comprises transmitting a signal to a medicament delivery pump.

In Method 101, which is a variant of Method 100, the new mode is therapeutic, and the signal instructs the pump to receive and follow signals from the monitoring device.

In Method 102, which is a variant of Method 100, the new mode is adjunctive, and the signal instructs the pump to disregard received signals from the monitoring device.

In Method 103, which is a variant of Method 100, the new mode is therapeutic, and the signal instructs the pump to receive and follow signals from the monitoring device to control the user glucose concentration value to a target value.

In Method 104, which is a variant of Method 100, the new mode is therapeutic, and the signal instructs the pump to receive and follow signals from the monitoring device to control the user glucose concentration value to a target range of values.

In Method 105, which is a variant of Method 100, the new mode is therapeutic, and the signal instructs the pump to receive and follow signals from the monitoring device to control the user glucose concentration value only when the glucose concentration value is below a predetermined value, above a predetermined value, or within a predetermined range of values.

In Method 106, which is a variant of Method 1-7 or 11, the initial mode is adjunctive and the new mode is therapeutic, and wherein in the new mode the monitoring device is configured to calculate a recommended insulin bolus and wherein the displaying on the user interface further comprises displaying the calculated recommended insulin bolus without a calibration meter reading, and wherein in the initial mode the monitoring device is configured to not calculate and display a recommended insulin bolus without a calibration meter reading.

In Method 107, which is a variant of Method 1-7 or 11, upon a step of sensor start up, the initial mode is adjunctive, and wherein the displaying indicating the new mode of operation further comprises displaying low-resolution data.

In Method 108, which is a variant of Method 107, the Method further comprises determining a level of confidence in the sensor over a period of time, and once the measured level of confidence has reached a predetermined threshold, the step of displaying further comprises displaying high-resolution data and causing a transition to a therapeutic mode.

In Method 109, which is a variant of Method 108, the determining a level of confidence includes receiving an external blood glucose meter reading.

In Method 110, which is a variant of Method 109, the external blood glucose meter reading correlates to what the monitoring device estimates the glucose concentration value to be or is used to calibrate the monitoring device.

In Method 111, which is a variant of Method 109, the Method further comprises configuring the monitoring device to enter a user-dependent calibration mode of operation.

In Method 112, which is a variant of Method 107, the Method further comprises receiving an external blood glucose meter reading, developing a level of confidence in the sensor over a period of time, and once the level of confidence has reached a predetermined threshold, causing the monitoring device to enter a user-dependent calibration mode of operation.

In Method 113, which is a variant of Method 1-7 or 11, the monitoring device operates in two modes of operation concurrently, one adjunctive and one therapeutic, and wherein the displaying further comprises displaying an initial splash screen with data displayed in the adjunctive mode of operation.

In Method 114, which is a variant of Method 113, upon receiving a selection from a user interface for data requiring a new mode of operation, causing a transition to the new mode of operation, receiving one or more data values required by the new mode of operation, and displaying the data using the new mode of operation.

In Method 115, which is a variant of Method 114, the selected data includes a hypoglycemic safety alarm, and wherein the new mode of operation is user-dependent calibration.

In Method 116, which is a variant of Method 1-7 or 12, the determined data includes data based on a glucose concentration value, and wherein the transition criteria is selected from the group consisting of: a glycemic state threshold, a GUI threshold, a glucose threshold, a glucose rate of change threshold, a glucose acceleration threshold, a predicted value of glucose or any of its rates of change, an excursion beyond a predetermined threshold, an alert criteria, a criteria for a glycemic danger zone, or a combination of the above.

In Method 117, which is a variant of Method 1-7 or 12, the transition criteria is selected from the group consisting of: a duration of time since a user last requested a glucose concentration value, a decision support mode, a user response to a query, a calibration mode of the monitoring device, or a combination of the above.

In Method 118, which is a variant of Method 1-7 or 12, the determining data includes transmitting a signal to cause a sensor to send a glucose concentration value.

In Method 119, which is a variant of Method 1-7 or 12, the determining data includes receiving a signal from a sensor corresponding to a glucose concentration value.

In Method 120, which is a variant of Method 1-7 or 12, the initial mode is on-demand transmission, the new mode is device-initiated transmission, the determined data is a glucose concentration value, and the transition criteria is the glucose concentration value being in a dangerous range for a period exceeding a first predetermined duration of time.

In Method 121, which is a variant of Method 120, the Method further comprises displaying an alert to the user on a user interface of the monitoring device until the user performs an action of responding to the alert.

In Method 122, which is a variant of Method 1-7 or 12, the initial mode is device-initiated transmission, the new mode is on-demand transmission, the determined data is a glucose concentration value, and the transition criteria is the glucose concentration value being in a dangerous range for a period exceeding a second predetermined duration of time.

System 123 is a system for performing any one of Methods 1-122.

Device 124 is substantially as shown and/or described in the specification and/or drawings.

System 125 is substantially as shown and/or described in the specification and/or drawings.

Method 126 is substantially as shown and/or described in the specification and/or drawings.

Electronic Device 127 is provided, for monitoring data associated with a physiological condition, comprising: a continuous analyte sensor, wherein the continuous analyte sensor is configured to substantially continuously measure the concentration of analyte in the host, and to provide continuous sensor data indicative of the analyte concentration in the host; and a processor module configured to perform any one of Methods 1-122.

In Electronic Device 128, which is a variant of Electronic Device 127, the analyte is glucose.

Electronic Device 129 is provided, for delivering a medicament to a host, the device comprising: a medicament delivery device configured to deliver medicament to the host, wherein the medicament delivery device is operably connected to a continuous analyte sensor, wherein the continuous analyte sensor is configured to substantially continuously measure the concentration of analyte in the host, and to provide continuous sensor data indicative of the analyte concentration in the host; and a processor module configured to perform any one of Methods 1-122.

In Electronic Device 130, which is a variant of Electronic Device 129, the analyte is glucose and the medicament is insulin.

What is claimed is:

1. A method of operating an artificial pancreas system, the method comprising:
    initiating the artificial pancreas system in a first decision support mode of a plurality of decision support modes of the artificial pancreas system, the artificial pancreas system including a glucose monitoring system that is configured to measure glucose concentration data of a host, a display device configured to display the glucose concentration data of the host measured by the glucose monitoring system, and an insulin pump that is configured to administer insulin to the host based on the glucose concentration data of the host measured by the glucose monitoring system, the plurality of decision support modes of the artificial pancreas system including at least an adjunctive phase during which the artificial pancreas system is used to provide information based on the glucose concentration of the host measured by the glucose monitoring system and/or a recommendation based on the glucose concentration of the host measured by the glucose monitoring system and during which the artificial pancreas system is not being used with the insulin pump, a low glucose phase during which the insulin pump is disabled if low glucose levels are detected for the host by the glucose monitoring system, an alarm phase during which an alarm is generated if low glucose levels are detected for the host by the glucose monitoring system prior to disabling the insulin pump, and a closed-loop phase during which the insulin pump is controlled to dose insulin to the host;
    receiving or determining data usability data concerning the glucose concentration data, wherein the data usability data is based on at least one of accuracy, reliability, stability or confidence in the glucose concentration data; and
    transitioning the artificial pancreas system to a second decision support mode of the plurality of decision support modes of the artificial pancreas system based on a comparison of the received or determined data usability data to one or more decision support criteria, wherein the second decision support mode comprises a different one of the plurality of decision support modes of the artificial pancreas system, and wherein each of the plurality of decision support modes of the artificial pancreas system are configured to display the glucose concentration data of the host via the display device.

2. A method of operating an artificial pancreas system, the method comprising:
    initiating the artificial pancreas system in a first decision support mode of a plurality of decision support modes of the artificial pancreas system, the artificial pancreas system including a glucose monitoring system that is configured to measure glucose concentration data of a host, a display device configured to display the glucose concentration data of the host measured by the glucose monitoring system, and an insulin pump that is configured to administer insulin to the host based on the glucose concentration data of the host measured by the glucose monitoring system,
    wherein the first decision support mode comprises one of a low glucose phase during which the insulin pump is disabled if low glucose levels are detected for the host by the glucose monitoring system or an alarm phase during which an alarm is generated if low glucose levels are detected for the host by the glucose monitoring system prior to disabling the insulin pump;
    receiving or determining data usability data concerning the glucose concentration data; and
    transitioning the artificial pancreas system to a second decision support mode of the plurality of decision support modes based on a comparison of the received or determined data usability data to one or more decision support criteria, wherein the second decision support mode comprises one of a closed-loop phase during which the insulin pump is controlled to dose insulin to the host or an adjunctive phase during which the artificial pancreas system is used to provide information based on the glucose concentration of the host measured by the glucose monitoring system and/or a recommendation based on the glucose concentration of the host measured by the glucose monitoring system and during which the artificial pancreas system is not being used with the insulin pump, and wherein each of the plurality of decision support modes are configured to display the glucose concentration data of the host via the display device.

3. A method of operating an artificial pancreas system, the method comprising:
    initiating the artificial pancreas system in a first decision support mode of a plurality of decision support modes of the artificial pancreas system, the artificial pancreas system including a glucose monitoring system that is configured to measure glucose concentration data of a host, a display device configured to display the glucose concentration data of the host measured by the glucose monitoring system, and an insulin pump that is configured to administer insulin to the host based on the glucose concentration data of the host measured by the glucose monitoring system, wherein the first decision support mode comprises one of a closed-loop phase during which the insulin pump is controlled to dose insulin to the host or an adjunctive phase during which the artificial pancreas system is used to provide information based on the glucose concentration of the host measured by the glucose monitoring system and/or a recommendation based on the glucose concentration of the host measured by the glucose monitoring system and during which the artificial pancreas system is not being used with the insulin pump;

receiving or determining data usability data concerning the glucose concentration data; and transitioning the artificial pancreas system to a second decision support mode of the plurality of decision support modes based on a comparison of the received or determined data usability data to one or more decision support criteria, wherein the second decision support mode comprises one of a low glucose phase during which an insulin pump is disabled if low glucose levels are detected for the host by the glucose monitoring system or an alarm phase during which an alarm is generated if low glucose levels are detected for the host by the glucose monitoring system prior to disabling the insulin pump, and wherein each of the plurality of decision support modes are configured to display the glucose concentration data of the host via the display device.

4. A method of operating an artificial pancreas system, the method comprising:

initiating the artificial pancreas system in a first decision support mode of a plurality of decision support modes of the artificial pancreas system, the artificial pancreas system including a glucose monitoring system that is configured to measure glucose concentration data of a host, a display device configured to display the glucose concentration data of the host measured by the glucose monitoring system, and an insulin pump that is configured to administer insulin to the host based on the glucose concentration data of the host measured by the glucose monitoring system, wherein the first decision support mode comprises one of an adjunctive phase during which the the artificial pancreas system is used to provide information based on the glucose concentration of the host measured by the glucose monitoring system and/or a recommendation based on the glucose concentration of the host measured by the glucose monitoring system and during which the artificial pancreas system is not being used with the insulin pump, a low glucose phase during which the insulin pump is disabled if low glucose levels are detected for the host by the glucose monitoring system, or an alarm phase during which an alarm is generated if low glucose levels are detected for the host by the glucose monitoring system prior to disabling the insulin pump;

receiving or determining data usability data concerning the glucose concentration data; and transitioning the artificial pancreas system to a second decision support mode of the plurality of decision support modes based on a comparison of the received or determined data usability data to one or more decision support criteria, wherein the second decision support mode is different than the first decision support mode and comprises a different one of the adjunctive phase, the low glucose phase, or the alarm phase, and wherein each of the plurality of decision support modes are configured to display the glucose concentration data of the host via the display device.

5. A method of operating an artificial pancreas system, the method comprising:

initiating the artificial pancreas system in a first decision support mode of a plurality of decision support modes of the artificial pancreas system, the artificial pancreas system including a glucose monitoring system that is configured to measure glucose concentration data of a host, a display device configured to display the glucose concentration data of the host measured by the glucose monitoring system, and an insulin pump that is configured to administer insulin to the host based on the glucose concentration data of the host measured by the glucose monitoring system, wherein the first decision support mode comprises one of an adjunctive phase during which the artificial pancreas system is used to provide information based on the glucose concentration of the host measured by the glucose monitoring system and/or a recommendation based on the glucose concentration of the host measured by the glucose monitoring system and during which the artificial pancreas system is not being used with the insulin pump, a low glucose phase during which the insulin pump is disabled if low glucose levels are detected for the host by the glucose monitoring system, or an alarm phase during which an alarm is generated if low glucose levels are detected for the host by the glucose monitoring system prior to disabling the insulin pump;

receiving or determining data usability data concerning the glucose concentration data; and transitioning the artificial pancreas system to a second decision support mode of the plurality of decision support modes based on a comparison of the received or determined data usability data to one or more decision support criteria, wherein the second decision support comprises one of a closed-loop phase during which the insulin pump is controlled to dose insulin to the host or a partial closed-loop phase during which the insulin pump is controlled to dose insulin except for meal time manual assist bolusing, and wherein each of the plurality of decision support modes are configured to display the glucose concentration data of the host via the display device.

6. The method of claim 1, wherein the first decision support mode comprises one of the adjunctive phase, the low glucose phase, or the alarm phase, and wherein the second decision support mode comprises a different one of the adjunctive phase, the low glucose phase, or the alarm phase.

7. The method of claim 1, wherein the first decision support mode comprises one of the adjunctive phase, the low glucose phase, or the alarm phase, and wherein the second decision support mode comprises the closed-loop phase.

8. The method of claim 1, wherein the first decision support mode comprises the closed-loop phase, and wherein the second decision support mode comprises one of the adjunctive phase, the low glucose phase, or the alarm phase.

9. The method of claim 1, wherein the first decision support mode comprises the low glucose phase, and wherein the second decision support mode comprises the alarm phase.

10. The method of claim 1, wherein the first decision support mode comprises the alarm phase, and wherein the second decision support mode comprises the low glucose phase.

11. The method of claim 2, wherein the first decision support mode comprises the low glucose phase, and wherein the second decision support mode comprises the closed-loop phase.

12. The method of claim 2, wherein the first decision support mode comprises the low glucose phase, and wherein the second decision support mode comprises the adjunctive phase.

13. The method of claim 2, wherein the first decision support mode comprises the alarm phase, and wherein the second decision support mode comprises the closed-loop phase.

14. The method of claim 2, wherein the first decision support mode comprises the alarm phase, and wherein the second decision support mode comprises the adjunctive phase.

15. The method of claim 3, wherein the first decision support mode comprises the closed-loop phase, and wherein the second decision support mode comprises the low glucose phase.

16. The method of claim 3, wherein the first decision support mode comprises the closed-loop phase, and wherein the second decision support mode comprises the adjunctive phase.

17. The method of claim 3, wherein the first decision support mode comprises the adjunctive phase, and wherein the second decision support mode comprises the low glucose phase.

18. The method of claim 3, wherein the first decision support mode comprises the adjunctive phase, and wherein the second decision support mode comprises the closed-loop phase.

19. The method of claim 4, wherein the first decision support mode comprises the adjunctive phase, and wherein the second decision support mode comprises the alarm phase.

20. The method of claim 4, wherein the first decision support mode comprises the low glucose phase, and wherein the second decision support mode comprises the alarm phase.

* * * * *